US006573431B1

(12) United States Patent
Lenee et al.

(10) Patent No.: US 6,573,431 B1
(45) Date of Patent: Jun. 3, 2003

(54) RECOMBINANT PREDUODENAL LIPASES AND POLYPEPTIDES DERIVATIVES PRODUCED BY PLANTS, PROCESSES FOR OBTAINING THEM AND THEIR USES

(75) Inventors: Philippe Lenee, Nouméa (FR); Véronique Gruber, Chamalières (FR); Sylvie Baudino, Orcines (FR); Bertrand Merot, Volvic (FR); Claude Benicourt, Houilles (FR); Claire Cudrey, Gières (FR)

(73) Assignees: Biochem S.A., Aubiere (FR); Jouveinal S.A., Paris (FR)

( * ) Notice: Subject to any disclaimer, the term of this patent is extended or adjusted under 35 U.S.C. 154(b) by 0 days.

(21) Appl. No.: 09/348,930

(22) Filed: Jul. 2, 1999

Related U.S. Application Data

(63) Continuation of application No. 08/945,321, filed as application No. PCT/FR96/00606 on Apr. 19, 1996, now abandoned.

(30) Foreign Application Priority Data

Apr. 20, 1995 (FR) .............................................. 95/04754

(51) Int. Cl.[7] .......................... A01H 5/00; C12N 15/85; C07H 21/04
(52) U.S. Cl. ...................... 800/295; 800/278; 800/288; 800/298; 800/305; 800/306; 800/312; 800/317.2; 800/317; 800/317.3; 800/320; 800/320.1; 800/320.2; 800/320.3; 800/317.4; 800/322; 435/320.1; 435/410; 435/411; 435/412; 435/414; 435/415; 435/416; 435/417; 536/23.1; 536/23.5
(58) Field of Search .............................. 435/320.1, 410, 435/411, 412, 414, 415, 416, 417; 536/23.5, 23.1; 800/278, 288, 295, 298, 317.3, 320, 305, 320.1, 306, 320.2, 312, 320.3, 317.2, 317.4, 317, 322

(56) References Cited

U.S. PATENT DOCUMENTS 5,807,726 A * 9/1998 Blanchard et al. .......... 435/198
5,858,734 A * 1/1999 Horn et al. ................. 435/91.2

FOREIGN PATENT DOCUMENTS

| EP | 0261016 | 9/1987 |
|---|---|---|
| EP | 0449376 | 3/1991 |
| EP | 0542629 | 11/1992 |
| GB | 2090613 | 12/1980 |
| GB | 2188057 | 2/1986 |
| WO | 86/01532 | 3/1986 |
| WO | 91/06661 | 5/1991 |
| WO | 92/01042 | 1/1992 |
| WO | 93/03161 | 2/1993 |
| WO | 94//13816 | 6/1994 |
| WO | 94/20610 | 9/1994 |
| WO | 96/03511 | 2/1996 |

OTHER PUBLICATIONS

Bruggemann et al. Biotechniques. vol. 10, No. 2 (1991) pp. 202–4, 206, 208–9.*
Pen, J., Biotechnology, "Production of Active Bacillus Licheniformis Alpha–Amylase in Tobacco and its Application in Starch Liquefaction", 1992, vol. 10, pp 292–296, XP002013284.
Benicourt, C., et al., *Elsevier Science Pub.,, Clinical Ecology of Cystic Fibrosis*, "Potential Use of a Recombinant Dog Gastric Lipase as an Enzymatic Supplement to Pancreatic Extracts in Cystic Fibrosis", 1993, pp 291–295.
Gilbert, E.J., *Enzyme Microb. Technol.*, "Pseudomonas Lipases: Biochemical Properties and Molecular Cloning". 1993, vol. 15, pp 634–645.
Anderson, R.A., *J. Biol. Chemistry*, Cloning and Expression of cDNA encoding Human Lysosomal Acid Lipase/Cholestery Ester Hydrolase, 1991, vol. 226, pp 22479–22484.

* cited by examiner

*Primary Examiner*—Jeffrey Fredman
*Assistant Examiner*—Juliet C. Einsmann
(74) *Attorney, Agent, or Firm*—Kathleen M. Williams; Palmer & Dodge LLP

(57) ABSTRACT

The invention concerns the use of recombinant nucleotides sequences containing cDNA coding for a preduodenal lipase, or any sequence derived from this cDNA, for transforming plant cells in order to obtain recombinant preduodenal lipase or polypeptide derivatives.

Figure 6:
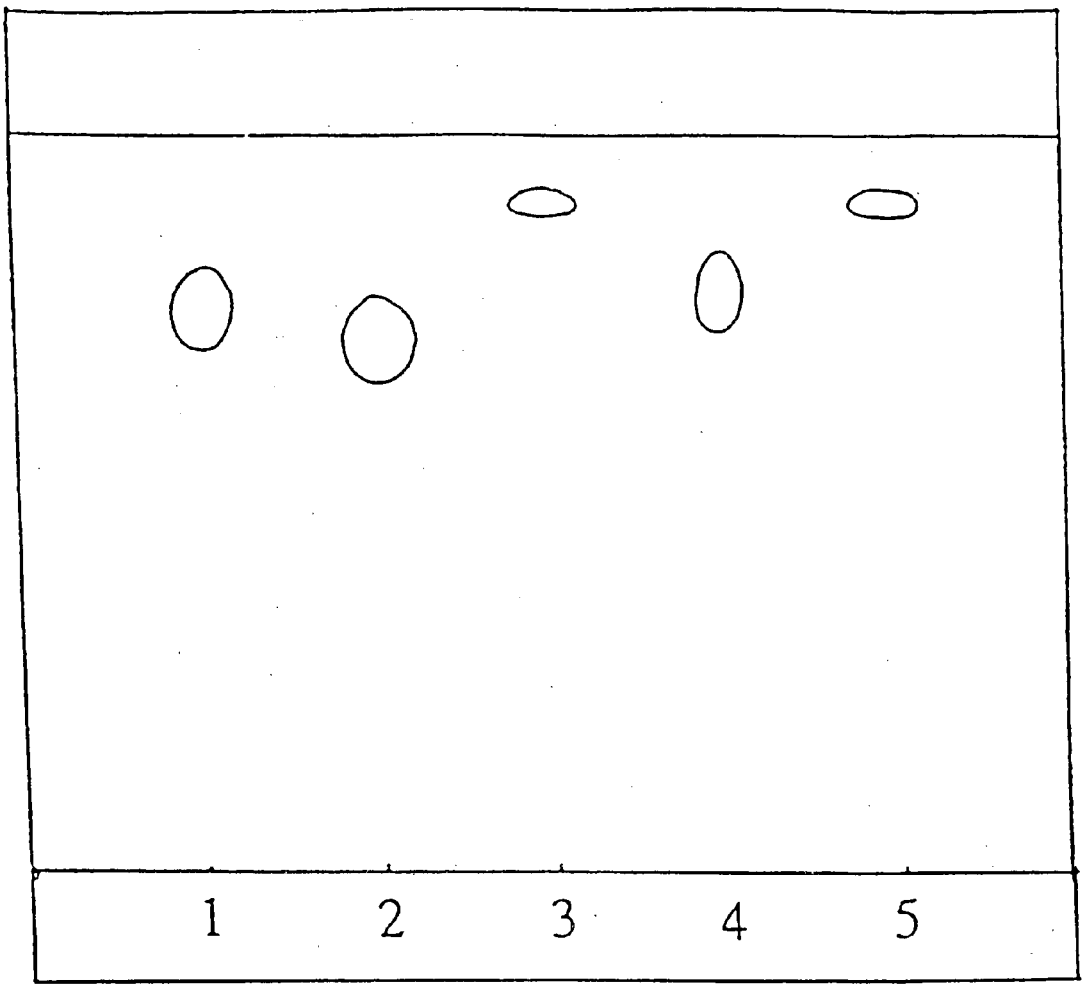

The invention also concerns the use of genetically modified plants or parts thereof, or extracts of these plants or the use of recombinant preduodenal lipase or résultant polypeptide derivatives in the field of foodstuffs, or for producing medicaments, or in industry.

11 Claims, 8 Drawing Sheets

```
TTGTTTGGAA AATTACATCC CACAAACCCT GAAGTGACCA TGAATATAAG TCAGATGATC    60
ACCTACTGGG GATACCCAGC TGAGGAATAT GAAGTTGTGA CCGAAGACGG TTATATCCTT   120
GGGATCGACA GAATTCCTTA TGGGAGGAAA AATTCAGAGA ATATAGGCCG GAGACCTGTT   180
GCATTTTTGC AACACGGTTT GCTCGCATCA GCCACAAACT GGATCTCCAA CCTGCCCAAC   240
AACAGCCTGG CCTTCATCCT GGCCGACGCC GGGTACGACG TGTGGCTGGG GAACAGCAGG   300
GGCAACACCT GGGCCAGGAG GAATCTGTAC TACTCGCCCG ACTCCGTCGA ATTCTGGGCT   360
TTCAGCTTTG ACGAGATGGC TAAATATGAC CTTCCCGCCA CCATTGACTT CATCTTGAAG   420
AAAACGGGAC AGGACAAGCT ACACTACGTT GGCCATTCCC AGGGCACCAC CATTGGTTTC   480
ATCGCCTTTT CCACCAATCC CAAGCTGGCG AAACGGATCA AAACCTTCTA TGCATTAGCT   540
CCCGTTGCCA CCGTGAAGTA CACCGAAACC CTGTTAAACA AACTCATGCT CGTCCCTTCG   600
TTCCTCTTCA AGCTTATATT TGGAAACAAA ATATTCTACC CACACCACTT CTTTGATCAA   660
TTTCTCGCCA CCGAGGTATG CTCCCGCGAG ACGGTGGATC TCCTCTGCAG CAACGCCCTG   720
TTTATCATTT GTGGATTTGA CACTATGAAC TTGAACATGA GTCGCTTGGA TGTGTATCTG   780
TCACATAATC CAGCAGGAAC ATCGGTTCAG AACGTGCTCC ACTGGTCCCA GGCTGTTAAG   840
TCTGGGAAGT TCCAAGCTTT TGACTGGGGA AGCCCAGTTC AGAACATGAT GCACTATCAT   900
CAGAGCATGC CTCCCTACTA CAACCTGACA GACATGCATG TGCCAATCGC AGTGTGGAAC   960
GGTGGCAACG ACTTGCTGGC CGACCCTCAC GATGTTGACC TTTTGCTTTC CAAGCTCCCC  1020
AATCTCATTT ACCACAGGAA GATTCCTCCT TACAATCACT TGGACTTTAT CTGGGCCATG  1080
GATGCCCCTC AAGCGGTTTA CAATGAAATT GTTTCCATGA TGGGAACAGA TAATAAGTAG  1140
TTCTAGATTT AAGGAATTAT TCTTTTATTG TTCCAAAATA CGTTCTTCTC TCACACGTGG  1200
TTTTCTATCA TGTTTGAGAC ACGGTGATTG TTCCCATGGT TTTGATTTCA GAAATGTGTT  1260
AGCATCAACA ATCTTTCCAT TGGTAATTTT TGAATTTAAA ATGATTTTTA AATTTGGGGC  1320
ATCTGGGTGG CTCAGTTGGC TAAGTCGTCT GCCTTGGCTT AAGTCATGAT CTCGGGGTCC  1380
TAGGATGGAG CCTTGTGTCT GGGCTCCTGC CGGGGCGGGG GTCTGCTTCT CCTCCTGCTG  1440
CTCCCCCCTG CTGCTGTGTG CACACACGCT CTCTCTCTCT CAAATAAATA AATAAATAAA  1500
TACTTAATAA AATAAAAAAA AAAAAAA                                      1528
```

Figure 1

```
Leu Phe Gly Lys Leu His Pro Thr Asn Pro Glu Val Thr Met Asn Ile
1               5                   10                  15
Ser Gln Met Ile Thr Tyr Trp Gly Tyr Pro Ala Glu Glu Tyr Glu Val
                20                  25                  30
Val Thr Glu Asp Gly Tyr Ile Leu Gly Ile Asp Arg Ile Pro Tyr Gly
            35                  40                  45
Arg Lys Asn Ser Glu Asn Ile Gly Arg Arg Pro Val Ala Phe Leu Gln
        50                  55                  60
His Gly Leu Leu Ala Ser Ala Thr Asn Trp Ile Ser Asn Leu Pro Asn
65                  70                  75                  80
Asn Ser Leu Ala Phe Ile Leu Ala Asp Ala Gly Tyr Asp Val Trp Leu
                85                  90                  95
Gly Asn Ser Arg Gly Asn Thr Trp Ala Arg Arg Asn Leu Tyr Tyr Ser
            100                 105                 110
Pro Asp Ser Val Glu Phe Trp Ala Phe Ser Phe Asp Glu Met Ala Lys
        115                 120                 125
Tyr Asp Leu Pro Ala Thr Ile Asp Phe Ile Leu Lys Lys Thr Gly Gln
130                 135                 140
Asp Lys Leu His Tyr Val Gly His Ser Gln Gly Thr Thr Ile Gly Phe
145                 150                 155                 160
Ile Ala Phe Ser Thr Asn Pro Lys Leu Ala Lys Arg Ile Lys Thr Phe
                165                 170                 175
Tyr Ala Leu Ala Pro Val Ala Thr Val Lys Tyr Thr Glu Thr Leu Leu
            180                 185                 190
Asn Lys Leu Met Leu Val Pro Ser Phe Leu Phe Lys Leu Ile Phe Gly
        195                 200                 205
Asn Lys Ile Phe Tyr Pro His His Phe Phe Asp Gln Phe Leu Ala Thr
    210                 215                 220
Glu Val Cys Ser Arg Glu Thr Val Asp Leu Leu Cys Ser Asn Ala Leu
225                 230                 235                 240
Phe Ile Ile Cys Gly Phe Asp Thr Met Asn Leu Asn Met Ser Arg Leu
                245                 250                 255
Asp Val Tyr Leu Ser His Asn Pro Ala Gly Thr Ser Val Gln Asn Val
            260                 265                 270
Leu His Trp Ser Gln Ala Val Lys Ser Gly Lys Phe Gln Ala Phe Asp
        275                 280                 285
Trp Gly Ser Pro Val Gln Asn Met Met His Tyr His Gln Ser Met Pro
    290                 295                 300
Pro Tyr Tyr Asn Leu Thr Asp Met His Val Pro Ile Ala Val Trp Asn
305                 310                 315                 320
Gly Gly Asn Asp Leu Leu Ala Asp Pro His Asp Val Asp Leu Leu Leu
                325                 330                 335
Ser Lys Leu Pro Asn Leu Ile Tyr His Arg Lys Ile Pro Pro Tyr Asn
            340                 345                 350
His Leu Asp Phe Ile Trp Ala Met Asp Ala Pro Gln Ala Val Tyr Asn
        355                 360                 365
Glu Ile Val Ser Met Met Gly Thr Asp Asn Lys
370                 375
```

Figure 2

```
TTGTTTGGAA AGCTTCATCC CACAAACCCT GAAGTGACCA TGAATATAAG TCAGATGATC    60
ACCTACTGGG GATACCCAGC TGAGGAATAT GAAGTTGTGA CCGAAGACGG TTATATCCTT   120
GGGATCGACA GAATTCCTTA TGGGAGGAAA AATTCAGAGA ATATAGGCCG GAGACCTGTT   180
GCATTTTTGC AACACGGTTT GCTCGCATCA GCCACAAACT GGATCTCCAA CCTGCCCAAC   240
AACAGCCTGG CCTTCATCCT GGCCGACGCC GGGTACGACG TGTGGCTGGG GAACAGCAGG   300
GGCAACACCT GGGCCAGGAG GAATCTGTAC TACTCGCCCG ACTCCGTCGA ATTCTGGGCT   360
TTCAGCTTTG ACGAGATGGC TAAATATGAC CTTCCCGCCA CCATTGACTT CATCTTGAAG   420
AAAACGGGAC AGGACAAGCT ACACTACGTT GGCCATTCCC AGGGCACCAC CATTGGTTTC   480
ATCGCCTTTT CCACCAATCC CAAGCTGGCG AAACGGATCA AAACCTTCTA TGCATTAGCT   540
CCCGTTGCCA CCGTGAAGTA CACCGAAACC CTGTTAAACA AACTCATGCT CGTCCCTTCG   600
TTCCTCTTCA AGCTTATATT TGGAAACAAA ATATTCTACC CACACCACTT CTTTGATCAA   660
TTTCTCGCCA CCGAGGTATG CTCCCGCGAG ACGGTGGATC TCCTCTGCAG CAACGCCCTG   720
TTTATCATTT GTGGATTTGA CACTATGAAC TTGAACATGA GTCGCTTGGA TGTGTATCTG   780
TCACATAATC CAGCAGGAAC ATCGGTTCAG AACGTGCTCC ACTGGTCCCA GGCTGTTAAG   840
TCTGGGAAGT TCCAAGCTTT TGACTGGGGA AGCCCAGTTC AGAACATGAT GCACTATCAT   900
CAGAGCATGC CTCCCTACTA CAACCTGACA GACATGCATG TGCCAATCGC AGTGTGGAAC   960
GGTGGCAACG ACTTGCTGGC CGACCCTCAC GATGTTGACC TTTTGCTTTC CAAGCTCCCC  1020
AATCTCATTT ACCACAGGAA GATTCCTCCT TACAATCACT TGGACTTTAT CTGGGCCATG  1080
GATGCCCCTC AAGCGGTTTA CAATGAAATT GTTTCCATGA TGGGAACAGA TAATAAGTAG  1140
TTCTAGATTT AAGGAATTAT TCTTTTATTG TTCCAAAATA CGTTCTTCTC TCACACGTGG  1200
TTTTCTATCA TGTTTGAGAC ACGGTGATTG TTCCCATGGT TTTGATTTCA GAAATGTGTT  1260
AGCATCAACA ATCTTTCCAT TGGTAATTTT TGAATTTAAA ATGATTTTTA AATTTGGGGC  1320
ATCTGGGTGG CTCAGTTGGC TAAGTCGTCT GCCTTGGCTT AAGTCATGAT CTCGGGGTCC  1380
TAGGATGGAG CCTTGTGTCT GGGCTCCTGC CGGGGCGGGG GTCTGCTTCT CCTCCTGCTG  1440
CTCCCCCCTG CTGCTGTGTG CACACACGCT CTCTCTCTCT CAAATAAATA AATAAATAAA  1500
TACTTAATAA AATAAAAAAA AAAAAAA                                      1528
```

Figure 3

```
AGAGAAACAG AATCCTAACT ATTTCTGAGG AAACTGCAGG TCCAAA ATG TGG CTG              55
CTT TTA ACA ATG GCA AGT TTG ATA TCT GTA CTG GGG ACT ACA CAT GGT            103
TTG TTT GGA AAA TTA CAT CCT GGA AGC CCT GAA GTG ACT ATG AAC ATT            151
AGT CAG ATG ATT ACT TAT TGG GGA TAC CCA AAT GAA GAA TAT GAA GTT            199
GTG ACT GAA GAT GGT TAT ATT CTT GAA GTC AAT AGA ATT CCT TAT GGG            247
AAG AAA AAT TCA GGG AAT ACA GGC CAG AGA CCT GTT GTG TTT TTG CAG            295
CAT GGT TTG CTT GCA TCA GCC ACA AAC TGG ATT TCC AAC CTG CCG AAC            343
AAC AGC CTT GCC TTC ATT CTG GCA GAT GCT GGT TAT GAT GTG TGG CTG            391
GGC AAC AGC AGA GGA AAC ACC TGG GCC AGA AGA AAC TTG TAC TAT TCA            439
CCA GAT TCA GTT GAA TTC TGG GCT TTC AGC TTT GAT GAA ATG GCT AAA            487
TAT GAC CTT CCA GCC ACA ATC GAC TTC ATT GTA AAG AAA ACT GGA CAG            535
AAG CAG CTA CAC TAT GTT GGC CAT TCC CAG GGC ACC ACC ATT GGT TTT            583
ATT GCC TTT TCC ACC AAT CCC AGC CTG GCT AAA AGA ATC AAA ACC TTC            631
TAT GCT CTA GCT CCT GTT GCC ACT GTG AAG TAT ACA AAA AGC CTT ATA            679
AAC AAA CTT AGA TTT GTT CCT CAA TCC CTC TTC AAG TTT ATA TTT GGT            727
GAC AAA ATA TTC TAC CCA CAC AAC TTC TTT GAT CAA TTT CTT GCT ACT            775
GAA GTG TGC TCC CGT GAG ATG CTG AAT CTC CTT TGC AGC AAT GCC TTA            823
TTT ATA ATT TGT GGA TTT GAC AGT AAG AAC TTT AAC ACG AGT CGC TTG            871
GAT GTG TAT CTA TCA CAT AAT CCA GCA GGA ACT TCT GTT CAA AAC ATG            919
TTC CAT TGG ACC CAG GCT GTT AAG TCT GGG AAA TTC CAA GCT TAT GAC            967
TGG GGA AGC CCA GTT CAG AAT AGG ATG CAC TAT GAT CAG TCC CAA CCT           1015
CCC TAC TAC AAT GTG ACA GCC ATG AAT GTA CCA ATT GCA GTG TGG AAC           1063
GGT GGC AAG GAC CTG TTG GCT GAC CCC CAA GAT GTT GGC TTT TGC TT            1111
CCA AAA CTC CCC AAT CTT ATT TAC CAC AAG GAG ATT CCT TTT TAC AAT           1159
CAC TTG GAC TTT ATC TGG GCA ATG GAT GCC CCT CAA GAA GTT TAC AAT           1207
GAC ATT GTT TCT ATG ATA TCA GAA GAT AAA AAG TAGTTCTGGA TTTAAAGAAT         1260
TATCCGTTTG TTTTTCCAAA ATACTTTATT CTCTCATACA TAGTATTTTC ATAATGTTTG         1320
ACATGCAGTG CTTCTTTCTG TAATTTTGAC TTTAGAAATA TATTGGC                      1367
```

Figure 4

| | | | | | | | | | | | | | | |
|---|---|---|---|---|---|---|---|---|---|---|---|---|---|---|
|Met|Trp|Leu|Leu|Leu|Thr|Met|Ala|Ser|Leu|Ile|Ser|Val|Leu|Gly|Thr|
|1| | | |5| | | |10| | | |15| | | |
|Thr|His|Gly|Leu|Phe|Gly|Lys|Leu|His|Pro|Gly|Ser|Pro|Glu|Val|Thr|
| | | |20| | | |25| | | |30| | | | |
|Met|Asn|Ile|Ser|Gln|Met|Ile|Thr|Tyr|Trp|Gly|Tyr|Pro|Asn|Glu|Glu|
| | |35| | | |40| | | |45| | | | | |
|Tyr|Glu|Val|Val|Thr|Glu|Asp|Gly|Tyr|Ile|Leu|Glu|Val|Asn|Arg|Ile|
| |50| | | |55| | | |60| | | | | | |
|Pro|Tyr|Gly|Lys|Lys|Asn|Ser|Gly|Asn|Thr|Gly|Gln|Arg|Pro|Val|Val|
|65| | | |70| | | |75| | | |80| | | |

(Figure 5 – partial amino acid sequence, 395 residues, reproduced in reading order:)

Met Trp Leu Leu Leu Thr Met Ala Ser Leu Ile Ser Val Leu Gly Thr
Thr His Gly Leu Phe Gly Lys Leu His Pro Gly Ser Pro Glu Val Thr
Met Asn Ile Ser Gln Met Ile Thr Tyr Trp Gly Tyr Pro Asn Glu Glu
Tyr Glu Val Val Thr Glu Asp Gly Tyr Ile Leu Glu Val Asn Arg Ile
Pro Tyr Gly Lys Lys Asn Ser Gly Asn Thr Gly Gln Arg Pro Val Val
Phe Leu Gln His Gly Leu Leu Ala Ser Ala Thr Asn Trp Ile Ser Asn
Leu Pro Asn Asn Ser Leu Ala Phe Ile Leu Ala Asp Ala Gly Tyr Asp
Val Trp Leu Gly Asn Ser Arg Gly Asn Thr Trp Ala Arg Arg Asn Leu
Tyr Tyr Ser Pro Asp Ser Val Glu Phe Trp Ala Phe Ser Phe Asp Glu
Met Ala Lys Tyr Asp Leu Pro Ala Thr Ile Asp Phe Ile Val Lys Lys
Thr Gly Gln Lys Gln Leu His Tyr Val Gly His Ser Gln Gly Thr Thr
Ile Gly Phe Ile Ala Phe Ser Thr Asn Pro Ser Leu Ala Lys Arg Ile
Lys Thr Phe Tyr Ala Leu Ala Pro Val Ala Thr Val Lys Tyr Thr Lys
Ser Leu Ile Asn Lys Leu Arg Phe Val Pro Gln Ser Leu Phe Lys Phe
Ile Phe Gly Asp Lys Ile Phe Tyr Pro His Asn Phe Phe Asp Gln Phe
Leu Ala Thr Glu Val Cys Ser Arg Glu Met Leu Asn Leu Leu Cys Ser
Asn Ala Leu Phe Ile Ile Cys Gly Phe Asp Ser Lys Asn Phe Asn Thr
Ser Arg Leu Asp Val Tyr Leu Ser His Asn Pro Ala Gly Thr Ser Val
Gln Asn Met Phe His Trp Thr Gln Ala Val Lys Ser Gly Lys Phe Gln
Ala Tyr Asp Trp Gly Ser Pro Val Gln Asn Arg Met His Tyr Asp Gln
Ser Gln Pro Pro Tyr Tyr Asn Val Thr Ala Met Asn Val Pro Ile Ala
Val Trp Asn Gly Gly Lys Asp Leu Leu Ala Asp Pro Gln Asp Val Gly
Leu Leu Leu Pro Lys Leu Pro Asn Leu Ile Tyr His Lys Glu Ile Pro
Phe Tyr Asn His Leu Asp Phe Ile Trp Ala Met Asp Ala Pro Gln Glu
Val Tyr Asn Asp Ile Val Ser Met Ile Ser Glu Asp Lys Lys

Figure 5

RECOMBINANT PREDUODENAL LIPASES AND POLYPEPTIDES DERIVATIVES PRODUCED BY PLANTS, PROCESSES FOR OBTAINING THEM AND THEIR USES

The present invention is a continuation of U.S. Ser. No. 08/945,321, filed Feb. 12, 1998, now abandoned, which was the national stage of PCT/FR96/00606, filed Apr. 19, 1996, which claims priority to FR9504754, filed Mar. 20, 1995.

The present invention relates to the production, by plants, of recombinant preduodenal lipases, in particular recombinant gastric lipases, and to other polypeptide derivatives of these which have a lipase activity, and to their uses, in particular as functional foods or in pharmaceutical compositions or in enzymatic formulations for agro-alimentary or industrial applications.

Dog gastric lipase (DGL) is a glycoprotein of 379 amino acids (AA) having a molecular weight of about 50 kilodaltons (kDa), which is synthesized in the form of a precursor containing a signal peptide at the amino-terminal ($NH_2$-terminal) end and is secreted by median cells of the mucosa of the fundus of the stomach of the dog (Carrière F. et al., 1991).

Human gastric lipase (HGL) is naturally synthesized in the form of a precursor and is described in the publication by Bodmer et al., 1987. The mature HGL protein is constituted by 379 amino acids. Its signal peptide (HGLSP) is composed of 19 amino acids.

These enzymes belong to a family of lipases called "preduodenal", some members of which have already been purified and in some cases even cloned (Docherty A.J.P. et al., 1985; Bodmer M. W. et al., 1987; Moreau H. et al., 1988; European Patents no. 0 191 061 and no. 0 261 016).

For a long time it has been taken for granted that hydrolysis of food lipids took place in the small intestine by the action of enzymes produced by the pancreas (Bernard C., 1849).

However, findings have suggested that the hydrolysis of triglycerides could have taken place in the stomach by the indirect means of preduodenal enzymes (Volhard, F., 1901; Shonheyder, F., and Volquartz, K., 1945). These enzymes, and in particular dog gastric lipase, have enzymatic and physico-chemical properties which differentiate them from mammalian pancreatic lipases. These differences between gastric and pancreatic lipases essentially relate to the following points: molecular weight, amino acid composition, resistance to pepsin, substrate specificity, optimum pH of action and stability in an acid medium.

Moreover, in vitro, under certain conditions, it is possible to demonstrate a synergistic action between gastric and pancreatic lipases on the hydrolysis of long-chain triglycerides (Gargouri, Y. et al., 1989).

Several pathological situations (cystic fibrosis, exocrine pancreatic insufficiency) where patients are totally or partly lacking in exocrine pancreatic secretion and therefore in enzymes necessary for hydrolysis of foods (amylases, lipases, proteases) are known. Non-absorption of fats in the intestine, and in particular of long-chain triglycerides, manifests itself by a very significant increase in steatorrhoea in these patients and by a very considerable slowing down in weight increase in young patients. To correct this, porcine pancreatic extracts are administered to these subjects at mealtimes. The therapeutic efficacy of these a extracts could be distinctly improved by co-prescription of DGL due to the specificity of its action on long-chain triglycerides.

The article by Carrière et al. (1991) describes the purification and determination of the $NH_2$-terminal sequence of DGL. A process for extraction of this enzyme from dog stomachs is also described in this publication. This process essentially comprises steeping the stomachs of dogs in an acid medium (pH 2.5) in the presence of water-soluble salts which promote the salting out of lipase in the said medium. The DGL can be purified to homogeneity by stages of filtration over a molecular sieve and ion exchange chromatography. The purified DGL obtained by these processes is a glycoprotein having a molecular weight of 49,000 daltons, 6,000 of which correspond to sugars and 43,000 to the protein part.

Obvious reasons of the difficulties of procurement of the stomachs of dogs prevent any development of this process both in the laboratory and industrially. This results in the need to discover a process which allows production of DGL in a large amount, dispensing with the use of the stomachs of dogs.

The nucleotide and peptide sequences of DGL were determined with the aim of industrial production of DGL by a process using genetic engineering. These works have been the subject of the international application no. WO 94/13816, filed on Dec. 16, 1993.

The process for the production of recombinant DGL described in this international application claims *Escherichia coli* (*E. coli*) as the transformed host cell which can produce DGL.

Some difficulties encountered during production of recombinant DGL by *E. coli*, in particular the need to culture large quantities of *E. coli* in a fermenter, with high costs, have led to inventors seeking other processes for the production of this DGL.

Mammalian cells are, a priori, more suitable for expression of mammalian genes. However, their use poses problems of maturation of proteins. The enzymatic equipment which realises post-translational maturation differs from one tissue, one organ or one species to another. For example, it has been reported that post-translational maturation of a plasma protein may be different if it is obtained from human blood or if it is produced by a recombinant cell, such as ovarian cells of the Chinese hamster or in the milk of a transgenic animal. Furthermore, the low expression levels obtained with mammalian cells involve cultures in vitro in very large volumes at high costs. The production of recombinant proteins in the milk of transgenic animals (mice, sheep and cows) allows production costs to be reduced and the problems of the level of expression to be overcome. However, ethical problems and problems of viral and subviral contamination (prions) remain.

For these reasons, transgenesis of mammalian genes into a plant cell could provide a route for production of new recombinant proteins in large quantities, at a reduced production cost and without risk of viral or subviral contamination.

In 1983, several laboratories discovered that it was possible to transfer a heterologous gene into the genome of a plant cell (Bevan et al., 1983; Herrera-Estrella et al., 1983 a and b) and to regenerate transgenic plants from these genetically modified cells. All the cells of the plant thus have the genetically modified characteristic, which is transmitted to the descendants by sexed fertilization.

As a result of these works, various teams concerned themselves with the production of mammalian recombinant proteins in plant cells or in transgenic plants (Barta et al., 1986; Marx, 1982). One of the first truly significant results is in this field was the production of antibodies in transgenic tobacco plants (Hiatt et al., 1989).

To express a heterologous protein in the seed, the protein storage site in plants, Vandekerckhove's team (1989) fused the sequence which codes for leu-enkephalin to the gene which codes for the 2S albumin of *Arabidopsis thaliana*. With this construction, transgenic rape plants which express the leu-enkephalin specifically in the seeds at expression levels of the order of 0.1% of the total proteins were produced. In 1990, Sijmons and colleagues transferred the gene of human serum albumin into cells of tobacco and potato. Whatever the origin of the signal peptides (human or plant), human serum albumin levels of the order of 0.02% of the total proteins were obtained in potato leaves, stems and tubers.

Other mammalian recombinant proteins have also been produced in plants: the surface antigen of hepatitis B (Mason et al., 1992), interferons (De Zoeten et al., 1989; Edelbaum et al., 1992; Truve et al., 1993); a murine anti-Streptococcus mutans antibody, the agent of dental caries (Hiatt and Ma, 1992; Ma et al., 1994), fragments of the scFV anti-cancer cell antibody (Russel D., 1994), an anti-herpes antibody (Russel D., 1994), hirudin (Moloney et al., 1994), the cholera toxin (Hein R., 1994) and human epidermal growth factor (EGF) (Higo et al., 1993).

All of these researches have demonstrated that the production of mammalian recombinant proteins in plant cells is possible and that the mechanisms of synthesis of proteins from DNA sequences are similar in animal cells and plant cells. However, some differences exist between plant and animal cells, in particular in the maturation of polymannoside glycans into complex glycans, or in the cleavage sites of signal peptides, and it thus cannot be ensured that active or sufficiently active mammalian proteins are obtained by transformation of plant cells.

The inventors have demonstrated that the use of plant cells transformed by an appropriate recombinant nucleotide sequence allows recombinant DGL, or recombinant HGL, or polypeptides derived from these having a sufficient enzymatic activity to be capable of being developed in an industrial application to be obtained.

The aim of the present invention is to provide a new process for the production, by plants, of mammalian recombinant preduodenal lipases, and more particularly of recombinant DGL or HGL, or polypeptides derived from these having an enzymatic activity, and more particularly a lipase activity, such that the said recombinant lipases or their derived polypeptides can be used industrially.

Another aim of the present invention is to provide tools for carrying out such a process, in particular new recombinant nucleotide sequences, genetically transformed plant cells, genetically transformed plants or parts of plant (notably leaves, stems, fruits, seeds or grains, roots) and genetically transformed fragments of these plants or parts of plants.

The aim of the invention is also to provide new mammalian recombinant preduodenal lipase(s), or any derived polypeptide, which are enzymatically active and are obtained from genetically transformed plant cells or plants.

The aim of the invention is also to provide new enzymatic compositions which can be used in the context of carrying out enzymatic reactions, in particular on an industrial scale.

The aim of the invention is also to provide new pharmaceutical compositions, in particular in the context of treatment of pathologies associated with a deficit in the production of lipase in the organism, such as cystic fibrosis.

Another aim of the present invention is to provide new fuels, also called biofuels, which have the advantage of being less polluting than fuels derived from petroleum and of being cheaper to produce.

Figure 7:
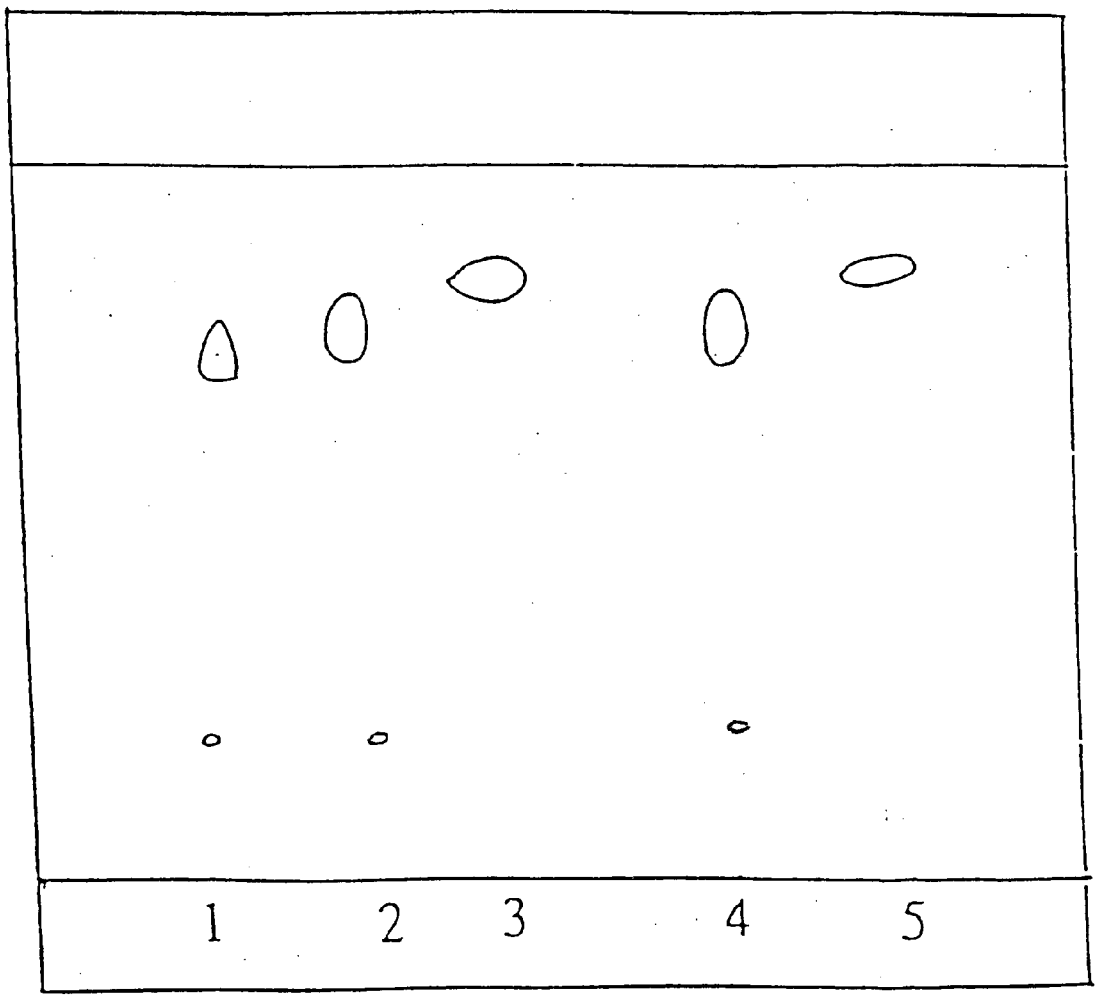
Figure 8:
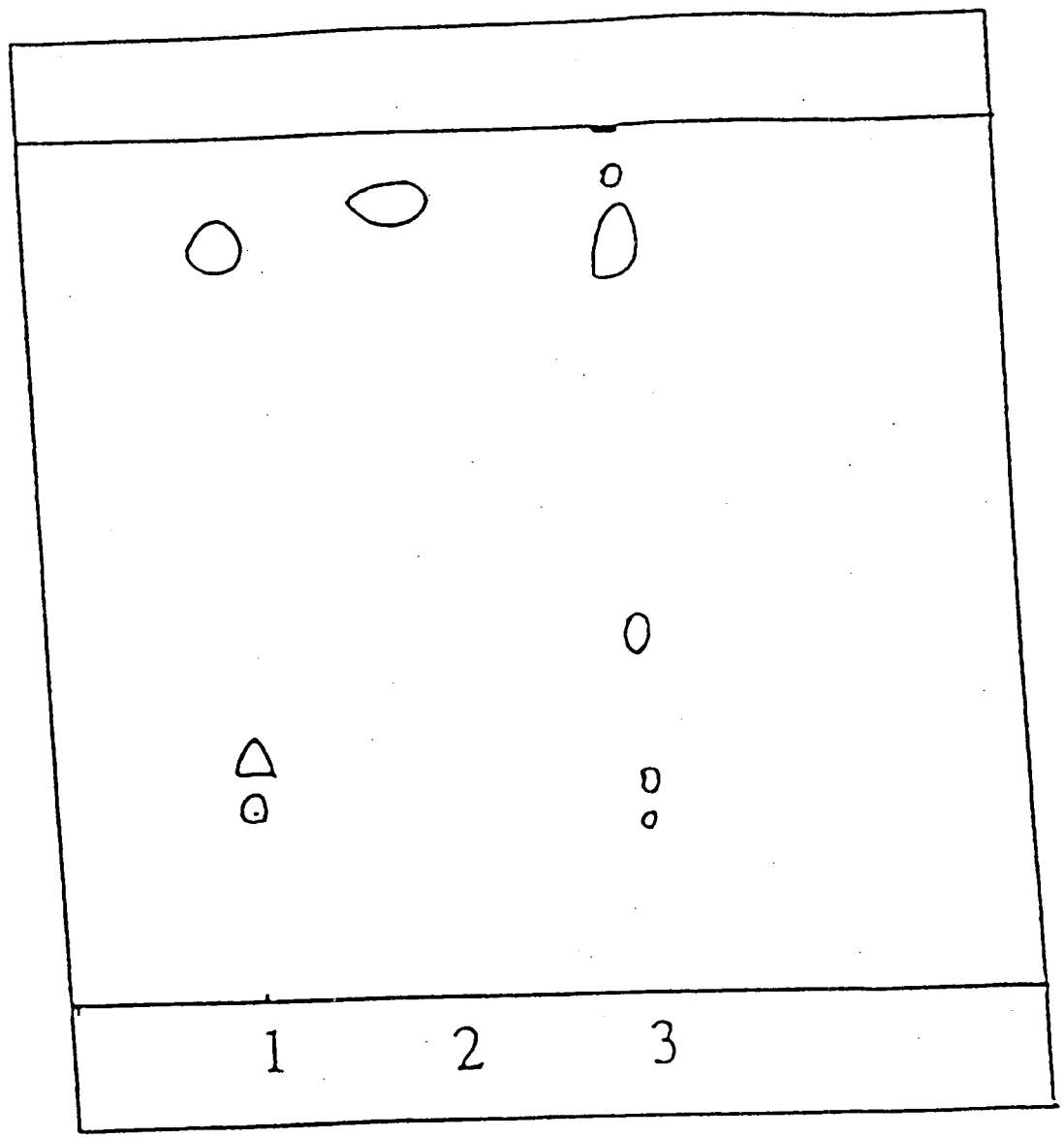

The invention is illustrated below with the aid of the following figures:

FIG. 1 shows the nucleotide sequence of the cDNA (SEQ ID NO: 7) of which the nucleotides situated at positions 1 to 1,137 code for the DGL shown on FIG. 2, and corresponding to SEQ ID NO 2, FIG. 2 shows the amino acid sequence of the DGL, and corresponding to SEQ ID NO 2, FIG. 3 shows a nucleotide sequence derived from the cDNA shown on FIG. 1, and corresponding to SEQ ID NO 1, the nucleotides situated in positions 1 to 1,137 of the said derived sequence coding for the DGL shown on FIG. 2, and corresponding to SEQ ID NO 2, FIG. 4 shows the nucleotide sequence (SEQ ID NO: 8) of the cDNA of which the nucleotides situated in positions 47 to 1240 code for the precursor of the HGL of 398 amino acids, and the nucleotides situated in positions 104 to 1240 code for the mature HGL of 379 amino acids, FIG. 5 shows the amino acid sequence of HGL (SEQ ID NO: 9), the precursor of HGL being delimited by the amino acids situated at positions 1 and 398, the mature HGL being delimited by the amino acids situated at positions and 398, FIGS. 6, 7 and 8 illustrate the various tests carried out in the context of the preparation of methyl oleate from transformed seeds according to the invention.

The present invention relates to the use of a recombinant nucleotide sequence containing, on the one hand, a cDNA which codes for any mammalian preduodenal lipase, namely the lipases whose nucleotide sequences which code for these have a percentage homology of at least about 75%, in particular of about 77% to about 85%, and of which the amino acid sequences have a percentage homology of at least 70%, in particular of about 80% to about 90% and having the property of being acid resistant and of being active at a pH of about 1 to about 5, and more particularly at a pH of about 1.5 to about 2, in particular a cDNA which codes for any mammalian gastric lipase, or a cDNA which codes for any polypeptide derived from the preduodenal lipases mentioned above by the addition and/or suppression and/or substitution of one (or more) amino acid(s), this derived polypeptide having the properties described above for preduodenal lipases and, one the other hand, elements which allow a plant cell to produce the preduodenal lipase coded by said cDNA, or to produce a derived polypeptide as defined above, in particular a transcription promoter and a transcription terminator recognized by the transcription machinery of plant cells, for the transformation of plant cells with a view to obtaining, from these cells, or from plants obtained from these, a mammalian recombinant preduodenal lipase in active enzyme form or one (or more) polypeptide(s) derived from the latter as defined above.

The present invention more particularly relates to the use of a recombinant nucleotide sequence containing, on the one hand, the cDNA shown on FIG. 1, which codes for the dog. gastric lipase (DGL) shown on FIG. 2, or a nucleotide sequence derived from this cDNA, in particular by addition and/or suppression and/or substitution of one (or more) nucleotide(s), the said derived sequence being capable of coding for a polypeptide, the amino acid sequence of which is identical to that of the DGL shown on FIG. 2, or for a polypeptide derived from the DGL by addition and/or suppression and/or substitution of one (or more) amino acid(s), this derived polypeptide having a lipase activity, and, on the other hand, elements which allow a plant cell to produce the polypeptide coded by the said cDNA or by an above mentioned derived sequence, in particular a transcription promoter and a transcription terminator recognized by the transcription machinery of plant cells (and more particularly by the RNA polymerases of the latter), for transformation of plant cells in order to obtain, from these cells or plants obtained from the latter, recombinant DGL in active enzyme form or one (or more) polypeptide(s) derived from the latter as defined above.

The invention also relates to any recombinant nucleotide sequence as described above containing, as the cDNA, that shown on FIG. 1, or a nucleotide sequence derived from the latter as defined above.

In this respect, the invention more particularly relates to any recombinant nucleotide sequence as described above containing the cDNA shown on FIG. 1, which codes for the dog gastric lipase (DGL) shown on FIG. 2.

The invention more particularly also relates to any recombinant nucleotide sequence as described above containing a nucleotide sequence derived from the cDNA shown on FIG. 1, the said derived nucleotide sequence being as defined above and coding for the dog gastric lipase (DGL) shown in FIG. 2. Such a derived sequence is advantageously that shown in FIG. 3, and corresponds to that shown on FIG. 1 in which the nucleotide A in position 12 is replaced by the nucleotide G, the nucleotide T in position 13 is replaced by the nucleotide C, and the nucleotide A in position 15 is replaced by the nucleotide T.

The recombinant nucleotide sequences according to the invention advantageously contain one (or more) sequence(s) coding for a peptide which is responsible for directing the recombinant polypeptides of the invention (that is to say the recombinant DGL or the above mentioned derived polypeptides) into a specific compartment of the plant cell, in particular into the endoplasmic reticulum or into the vacuoles, or even outside the cell, into the pectocellulosic wall or into the extracellular space, also called the apoplasm.

Among the transcription terminators which can be used for transformation of plant cells in the context of the present invention there may be mentioned the terminator polyA 35S of the cauliflower mosaic virus (CaMV) described in the article by Franck et al., 1980 or the polyA NOS terminator, which corresponds to the non-coding region 3' of the gene of nopaline synthase of plasmid Ti of *Agrobacterium tumefaciens* strain with nopaline (Depicker et al., 1982).

In this respect, the invention relates to any recombinant nucleotide sequence as described above containing, downstream of the said cDNA or of its derived sequence, the terminator polyA 35S of CaMV or the terminator polyA NOS of *Agrobacterium tumefaciens*.

Among the transcription promoters which can be used for transformation of plant cells in the context of the present invention there may be mentioned:

the promoter 35S, or advantageously the double-structured promoter 35S (pd35S) of CaMV, these promoters allowing expression of recombinant polypeptides according to the invention in the entire plant obtained from transformed cells according to the invention, and being described in the article by Kay et al., 1987, the promoter pCRU of the gene of cruciferin of the radish, which allows expression of the recombinant polypeptides of the invention solely in the seeds (or grains) of the plant obtained from transformed cells according to the invention and is described in the article by Depigny-This et al., 1992.

the promoters pGEA1 and pGEA6 corresponding to the non-coding region 5' of the genes of the reserve protein of grains, GEA1 and GEA6, respectively, of *Arabidopsis thaliana* (Gaubier et al. 1993), and allowing a specific expression in grains, the chimaeric promoter super-promoter pSP (PCT/US94/12946), constituted by the fusion of three transcriptional activators of the promoter of the gene of octopine synthase of *Agrobacterium tumefaciens,* of a transcriptional activator element of the promoter of the gene of mannopine synthase and of the promoter of mannopine synthase of *Agrobacterium tumefaciens,* the actine promoter of rice followed by the actine intron of rice (pAR-IAR) contained in the plasmid pAct1-F4 described by McElroy et al. (1991), the promoter of the gene of γzeine of corn (pγzeine) contained in the plasmid pγ63 described in Reina et al. (1990), and allows expression in the albumen of corn seeds.

In this respect, the invention relates to any recombinant nucleotide sequence as described above containing, upstream of the said cDNA or of its derived sequence, the double-structured promoter 35S (pd35S) of CaMV or the promoter pCRU of the gene of cruciferin of the radish or the promoters pGEA1 or pGEA6 of *Arabidopsis thaliana,* or the super-promoter pSP of *Agrobacterium tumefaciens,* or the promoter pAR-IAR of rice, or the promoter pγzeine of corn.

The sequences which code for a directing peptide used in the context of the present invention can be of plant, human or animal origin.

Among the sequences which code for a directing peptide of plant origin there may be mentioned:

the nucleotide sequence of 69 nucleotides (indicated in the examples'which follow) which codes for the prepeptide (signal peptide) of 23 amino acids of sporamin A in the sweet potato, this signal peptide allowing entry of recombinant polypeptides of the invention into the secretion system of transformed plant cells according to the invention (that is to say chiefly into the endoplasmic reticulum), the nucleotide sequence of 42 nucleotides (indicated in the examples which follow) which codes for the N-terminal vacuole-directing propeptide of 14 amino acids of sporamin A in the sweet potato, allowing the accumulation of recombinant polypeptides of the invention in the vacuoles of transformed plant cells according to the invention, the nucleotide sequence of 111 nucleotides (indicated in the examples which follow) which codes for the pre-propeptide of 37 amino acids of the sporamin A made up of the N-terminal part to the C-terminal part of 23 amino acids of the above mentioned signal peptide followed by the 14 amino acids of the above mentioned propeptide, this prepropeptide allowing entry of recombinant polypeptides of the invention into the secretion system, and their accumulation in the vacuoles, of transformed plant cells according to the invention, the three above mentioned sequences being described in the articles by Murakami et al., 1986, and Matsuoka and Nakamura, 1991, the carboxy-terminal propeptide of the lectin of barley described, in particular, in the articles by Schroeder- et al., 1993, and Bednarek and Ralkhel, 1991.

Among the sequences which code for a directing peptide of human or animal origin, there may be mentioned those which code for the signal peptide of human gastric lipase (HGL) as described in European Patent no. 0 191 061, or for that of rabbit gastric lipase (RGL) as described in European Patent Application no. 0 542 629, the sequence of which is indicated in the examples which follow, or for that of human pancreatic lipase (HPL), or also for that of dog gastric lipase (DGL).

There can also be mentioned, among the sequences which code for a directing peptide, that which codes for the tetrapeptide KDEL and allows directing in the endoplasmic reticulum.

In this respect, the invention relates to any recombinant nucleotide sequence as described above containing a sequence which codes for all or part of a signal peptide, such as that of sporamin A of the sweet potato or that of HGL or of RGL or of DGL, this sequence which codes for a signal peptide being situated, in the said recombinant nucleotide sequence, upstream of the said cDNA or of its derived sequence and downstream of the promoter used, such that the last C-terminal amino acid of the signal peptide is bonded to the first N-terminal amino acid of the polypeptide coded by the said cDNA or its derived sequence in the protein coded by the said recombinant nucleotide sequence.

The invention also relates to any recombinant nucleotide sequence as described above containing a sequence which codes for all or part of a vacuole-directing peptide, in particular that of sporamin A of the sweet potato, this sequence which codes for a vacuole-directing peptide being situated, in the said recombinant nucleotide sequence, between the sequence which codes for a signal peptide and that which codes for the said cDNA or its derived sequence such that first N-terminal amino acid of the vacuole-directing peptide is bonded to the last C-terminal amino acid of the signal peptide, and that the last C-terminal amino acid of the said directing peptide is bonded to the first N-terminal amino acid of the polypeptide coded by the said cDNA or its derived sequence in the protein coded by the said recombinant nucleotide sequence.

The invention also relates to any recombinant nucleotide sequence as described above containing a sequence which codes for all or part of a vacuole-directing peptide, in particular that of lectin of barley, this sequence which codes for a vacuole-directing peptide being situated, in the said recombinant nucleotide sequence, downstream of the sequence which codes for the said cDNA or its derived sequence such that the first N-terminal amino acid of the vacuole-directing peptide is bonded to the last C-terminal amino acid of the polypeptide coded by the said cDNA or its derived sequence in the protein coded by the said recombinant nucleotide sequence.

The invention more particularly relates to the following recombinant nucleotide sequences:
  that (called pd35S-PS-DGL) containing, in the direction 5'→3', the promoter pd35S of CaMV, the sequence which codes for the signal peptide of sporamin A, the latter being immediately followed by the nucleotide sequence shown on FIG. 3, and then the terminator polyA 35S of CaMV,
  that (called pd35S-PPS-DGL) containing, in the direction 5'→3', the promoter pd35S of CaMV, the sequence which codes for the prepropeptide of sporamin A, the latter being immediately followed by the nucleotide sequence shown on FIG. 3, and then the terminator polyA 35S of CaMV,
  that (called pd35S-RGLSP-DGL) containing, in the direction 5'→3', the promoter pd35S of CaMV, the sequence which codes for part of the signal peptide of RGL (that is to say for a sequence made up of the first 19 amino acids, indicated in the examples which follow below, the 9 nucleotides which code for the last 3 C-terminal amino acids being suppressed), the latter being immediately followed by the cDNA shown on FIG. 1, and then the terminator polyA 35S of CaMV,
  that (called pCRU-PS-DGL) containing, in the direction 5'→3', the promoter pCRU of cruciferin, the sequence which codes for the signal peptide of sporamin A, the latter being immediately followed by the nucleotide sequence shown on FIG. 3, and then the terminator polyA 35S of CaMV,
  that (called pCRU-PPS-DGL) containing, in the direction 5'→3', the promoter pCRU of cruciferin, the sequence which codes for the prepropeptide of sporamin A, the latter being immediately followed by the nucleotide sequence shown on FIG. 3, and then the terminator polyA 35S of CaMV,
  that (called pCRU-RGLSP-DGL) containing, in the direction 5'→3' the promoter pCRU of cruciferin, the sequence which codes for a part of the DGL signal peptide (as described above), the latter being immediately followed by the cDNA as represented in FIG. 1, or in FIG. 3, and the polyA 35S terminator of CaMV,
  that (called pGEA1-RGLSP-DGL) containing, in the direction 5'→3' the promoter pGEA1of *Arabidopsis thaliana,* the sequence which codes for a part of the signal peptide of RGL (as described above), the latter being immediately followed by the cDNA shown on FIG. 1, or on FIG. 3, then the terminator polyA 35S of CaMV,
  that (called pGEA6-RGLSP-DGL) containing, in the direction 5'→3' the promoter pGEA6 of *Arabidopsis thaliana,* the sequence which codes for a part of the signal peptide of RGL (as described above), the latter being immediately followed by the cDNA shown on FIG. 1, or on FIG. 3, then the terminator polyA 35S of CaMV,
  that (called pAR-IAR-RGLSP-DGL) containing, in the direction 5'43 3' the promoter pAR-IAR of rice, the sequence which codes for a part of the signal peptide of RGL (as described above), the latter being immediately followed by the cDNA shown on FIG. 1, or on FIG. 3, then the terminator polyA 35S of CaMV, or the terminator polyA NOS of *Agrobacterium tumefaciens,*
  that (called pγzeine-RGLSP-DGL) containing, in the direction 5'→3' the promoter pγzeine of corn, the sequence which codes for a part of the signal peptide of RGL (as described above), the latter being immediately followed by the cDNA shown on FIG. 1, or on FIG. 3, then the terminator polyA 35S of CaMV,
  that (called pγzeine-RGLSP-DGL-KDEL) containing, in the direction 5'→3' the promoter pγzeine of corn, the sequence which codes for a part of the signal peptide of RGL (as described above), the latter being immediately followed by the cDNA shown on FIG. 1, or on FIG. 3, then the sequence which codes for the tetrapeptide KDEL, then the terminator polyA 35S of CaMV, The recombinant nucleotide sequences of the invention advantageously also contain a nucleotide sequence which can be used as a marker of the said recombinant sequences, in particular for differentiation (and thus selection) of those of the plant cells which are transformed by the said recombinant sequences from those which are not.

Such a nucleotide sequence which can be used as a marker of the said recombinant sequences is preferably chosen from the genes of resistance to antibiotics, in particular the gene of resistance to kanamycin.

The invention also relates to any vector, in particular a plasmid vector, containing a recombinant nucleotide sequence according to the invention inserted at a site which is not essential for its replication.

The invention also relates to any cell host, in particular any bacteria, such as *Agrobacterium tumefaciens,* transformed by a vector as defined above.

The present invention also relates to any process for the preparation of recombinant DGL in active enzyme form and/or of one (or more) polypeptide(s) derived from the latter, in particular by addition and/or suppression and/or substitution of one (or more) amino acid(s), this (or these) derived polypeptide(s) having a lipase activity, characterized in that it comprises:

transformation of plant cells such that one (or more) recombinant nucleotide sequence(s) according to the invention is (or are) integrated into the genome of these cells, where appropriate, production of transformed plants from the abovementioned transformed cells, recovery of the recombinant DGL and/or of the above mentioned derived polypeptide(s) produced in the said cells or above mentioned transformed plants, in particular by extraction, followed, where appropriate, by purification.

According to one embodiment of the above mentioned process of the invention, the transformation of plant cells can be carried out by transfer of the recombinant nucleotide sequence of the invention into the protoplasts, in particular after incubation of the latter in a solution of polyethylene glycol (PEG) in the presence of divalent cations ($Ca^{2+}$) in accordance with the method described in the article by Krens et al., 1982.

The transformation of plant cells can also be carried out by electroporation, in particular in accordance with the method described in the article by Fromm et al., 1986.

The transformation of the plant cells can also be carried out by using a gene gun which allows projection, at very high speed, of metal particles coated with recombinant nucleotide sequences according to the invention, thus delivering genes inside the cell nucleus, in particular in accordance with the technique described in the article by Sanford, 1988.

Another method of transformation of plant cells is that of cytoplasmic or nuclear microinjection as described in the article by De La Penna et al., 1987.

According to a particularly preferred embodiment of the abovementioned process of the invention, the plant cells are transformed by bringing the latter together with a cell host transformed by a vector according to the invention, as described above, the said cell host being capable of infecting the said plant cells and allowing integration, into the genome of the latter, of recombinant nucleotide sequences of the invention initially contained in the genome of the abovementioned vector.

The above mentioned cell host used is advantageously *Agrobacterium tumefaciens*, in particular in accordance with the methods described in the articles by Bevan, 1984 and An et al., 1986, or also *Agrobacterium rhizogenes*, in particular in accordance with the method described in the article by Jouanin et al., 1987.

Among the, plant cells which can be transformed in the context of the present invention there may be mentioned those of rape, tobacco, maize, pea, tomato, carrot, wheat, barley, potato, soya, sunflower, lettuce, rice and lucerne.

According to one embodiment of the abovementioned process of the invention, the transformed plant cells according to the invention are cultured in vitro, in particular in bioreactors, in accordance with the method described in the article by Brodelius, 1988, in a liquid medium, or in accordance with the method described in the article by Brodelius et al., 1979, in immobilized form, or also in accordance with the method described in the article by Deno et al., 1987, which is carried out by culture of transformed roots in vitro.

The abovementioned in vitro culture media are then recovered to extract from them, and where appropriate to purify, in particular by chromatography, the recombinant DGL and/or the derived polypeptide(s) defined above produced by the said transformed cells cultured in vitro.

According to a preferred embodiment of the abovementioned process for the preparation of recombinant DGL and/or derived polypeptide(s) according to the invention, transformation of the plant cells is followed by a stage of production of transformed plants by culturing the said transformed cells in a suitable medium. The recombinant DGL and/or the derived polypeptide(s) produced in the cells of the whole plants thus obtained are recovered by extraction, carried out on the whole plants or fragments of these plants (in particular on the leaves, the stems or fruits), or on seeds produced by these plants, this extraction being followed, where appropriate, by a stage of purification of the recombinant DGL and/or of the derived polypeptide(s).

The transformed plants used for recovery of the recombinant DGL and/or of the derived polypeptide(s) in the context of the abovementioned process are those of generation T0, that is to say those obtained by culture of transformed cells of the invention on a suitable medium, or advantageously those of the following generations (T1, T2 etc.) which are obtained by autofertilization of plants of the preceding generation and in which the recombinant nucleotide sequences of the invention are reproduced in accordance with the laws of Mendel.

Among the polypeptides derived from the recombinant DGL which can be obtained in the context of carrying out a process according to the invention there may be mentioned:

the polypeptide delimited by the amino acids situated in positions 55 and 379 of FIG. 2, also called polypeptide (Δ54), and represented by SEQ ID NO 4, said polypeptide being encoded by the nucleotide sequence represented by SEQ ID NO 3, the polypeptide delimited by the amino acids situated in positions and 379 in FIG. 2, also called polypeptide (Δ4), and represented by SEQ ID NO 6, said polypeptide being encoded by the nucleotide sequence represented by SEQ ID NO 5.

The invention more particularly relates to any process as described above for the preparation of the recombinant DGL shown on FIG. 2 and, where appropriate, the preparation of one (or more) derived polypeptide(s), in particular the abovementioned polypeptide (Δ54) and/or polypeptide (Δ4), the said process being characterized in that the stage of transformation of plant cells is carried out by integration, into the genome of the latter, of a recombinant sequence as described above containing, on the one hand, the cDNA shown on FIG. 1 and, on the other hand, the sequence which codes for the signal peptide of 22 amino acids of RGL, advantageously that which codes for the first 19 amino acids of the signal peptide of RGL.

The invention more particularly relates to a process for the preparation, as described above, of the recombinant DGL shown on FIG. 2, where appropriate in combination with the polypeptide (Δ54) and/or the polypeptide (Δ4), characterized in that it comprises:

transformation of explant cells of the leaves of a plant by bringing the latter together with a strain of *Agrobacterium tumefaciens* transformed by a plasmid as described above containing the abovementioned recombinant nucleotide sequence pd35S-RGLSP-DGL on a suitable culture medium, selection of the transformed explants on a medium containing kanamycin, production of transformed plants from the abovementioned transformed explants by culture of the latter on suitable media, extraction of the recombinant DGL and, where appropriate, of the polypeptide (Δ54) and/or the polypeptide (Δ4), in particular by grinding the leaves and/or the seeds and/or the fruits of the abovementioned transformed plants in a suitable buffer, centrifugation and recovery of the supernatant constituting the plant extract of enzymatic activity, where appropriate, purification of the recombinant DGL from the extract obtained during the preceding stage, in particular by chromatography carried out on the supernatant, which leads to the preparation of the recombinant DGL in an essentially pure form.

The invention also relates to the use of the abovementioned process for the preparation of the polypeptide (Δ54) or the polypeptide (Δ4) in an essentially pure form by purification of the latter from the extract obtained in the abovementioned process, in particular by chromatography carried out on the supernatant of the extraction.

The invention more particularly relates to the preparation of the abovementioned polypeptide (Δ4), where appropriate in an essentially pure form, by implementation of the abovementioned process in which the cells transformed with the sequence pd35S-RGLSP-DGL, are explant cells of solanaceae, in particular tobacco or tomato.

According to one embodiment of the abovementioned process, the polypeptide (Δ4) can be specifically obtained by extraction from the abovementioned leaves of transformed tobacco plants, in particular by grinding these leaves in an appropriate buffer, centrifuging and recovering the supernatant. The polypeptide (Δ4) can then be purified from the abovementioned leaf extract, containing said polypeptide (Δ4), in particular by chromatography carried out on the abovementioned supernatant.

The invention more particularly relates to any process as described above for the preparation of recombinant DGL and/or of one (or more) polypeptide(s) derived from the latter, as defined above, characterized in that the stage of transformation of the plant cells is carried out by integration, into the genome of the latter, of a sequence containing, on the one hand, the nucleotide sequence shown on FIG. 3 and, on the other hand, the sequence which codes for the signal peptide of the sporamin A described above.

Among the polypeptides derived from the recombinant DGL which can be obtained in the context of carrying out the process described above there may be mentioned the abovementioned polypeptide (Δ54) and/or polypeptide (Δ4).

The invention more particularly relates to a process for the preparation of the abovementioned recombinant DGL and/or polypeptide (Δ54) and/or polypeptide (Δ4), characterized in that it comprises:

transformation of explant cells of a plant (in particular explants of leaves) by bringing the latter together with a strain of *Agrobacterium tumefaciens* transformed by a plasmid as described above containing the recombinant nucleotide sequence pd35S-PS-DGL and/or the sequence pd35S-PPS-DGL, selection of the transformed explants on a medium containing kanamycin, production of transformed plants from the abovementioned transformed explants by culture of the latter on suitable media, extraction of the recombinant DGL and/or the polypeptide (Δ54) and/or the polypeptide (Δ4), in particular by grinding the leaves and/or the seeds and/or the fruits of the abovementioned transformed plants in a suitable buffer, centrifugation and recovery of the supernatant constituting the plant extract of enzymatic activity, where appropriate, purification of the recombinant DGL and/or the polypeptide (Δ54) and/or the polypeptide (Δ4) from the extract obtained during the preceding stage, in particular by chromatography carried out on the supernatant, which leads to the preparation of the recombinant DGL and/or the polypeptide (Δ54) and/or the polypeptide (Δ4) in an essentially pure form.

The invention more particularly relates to a process for the preparation of the abovementioned polypeptide (Δ54) and/or polypeptide (Δ4) by carrying out the process described above, in which the transformed cells are explant cells of the leaves of solanaceae, in particular tobacco or tomato.

According to a particular embodiment of the abovementioned process of the invention, the polypeptide (Δ54) can be obtained specifically by extraction from the abovementioned transformed tobacco seeds, in particular by grinding these seeds in a suitable buffer, centrifuging and recovering the supernatant. The polypeptide (Δ54) can then be purified from the abovementioned seed extract containing the said polypeptide (Δ54), in particular by chromatography carried out on the abovementioned supernatant.

The invention more particularly relates to a process for the preparation of recombinant DGL and/or the polypeptide (Δ54) and/or the polypeptide (Δ4), characterized in that it comprises:

transformation of explant cells of a plant by bringing the latter together with a strain of *Agrobacterium tumefaciens* transformed by a plasmid as described above containing the recombinant nucleotide sequence pCRU-PPS-DGL and/or the sequence pCRU-PS-DGL and/or the sequence pGEA1-RGLSP-DGL and/or the sequence pGEA6-RGLSP-DGL and/or the sequence pAR-IAR-RGLSP-DGL and/or the sequence pγzeine-RGLSP-DGL and/or the sequence pγzeine-RGLSP-DGL-KDEL, selection of the transformed explants on a medium containing kanamycin, production of transformed plants from the abovementioned transformed explants by culture of the latter on suitable media, extraction of the recombinant DGL and/or the polypeptide (Δ54) and/or the polypeptide (Δ4), in particular by grinding seeds produced by the abovementioned transformed plants in a suitable buffer, centrifuging and recovering the supernatant containing the plant extract of enzymatic activity, where appropriate, purification of the recombinant DGL and/or the polypeptide (Δ54) and/or the polypeptide (Δ4) from the extract obtained during the preceding stage, in particular by chromatography carried out on the supernatant, which leads to the preparation of the recombinant DGL and/or the polypeptide (Δ54) and/or the polypeptide (Δ4) in an essentially pure form.

The invention more particularly relates to a process for the preparation of the abovementioned polypeptide (Δ54) by carrying out the process described above, in which the transformed cells are explant cells of rape, and tobacco, and the extraction of the polypeptide (Δ54) is made by grinding the transformed seeds.

The transformed plant cells in the processes described above are advantageously chosen from those of tobacco, rape, maize, pea, tomato, carrot, wheat, barley, potato, soya, sunflower, lettuce, rice and lucerne.

A more particular aim of the invention is a process for the preparation of recombinant DGL and/or of polypeptide (Δ54) and/or polypeptide (Δ4), characterized in that it includes:

the transformation of corn callus, by bombardment of the latter using a particle gun, with plasmids containing the recombinant nucleotide sequence pAR-IAR-RGLSP-DGL and/or the sequence pγzeine-RGLSP-DGL and/or the sequence pγzeine-RGLSP-DGL-KDEL, selection of the transformed calluses on a medium containing a selection agent such as kanamycin, production of transformed corn plants from the abovementioned transformed calluses by culture of the latter on appropriate media, extraction of the recombinant DGL and/or the polypeptide (Δ54) and/or the polypeptide (Δ4) in particular by grinding seeds produced by the abovementioned transformed plants in a suitable buffer, centrifuging and recovering the supernatant containing the plant extract of enzymatic activity, where appropriate, purification of the recombinant DGL and/or the polypeptide (Δ54) and/or the polypeptide (Δ4), from the extract obtained during the preceding stage, in particular by chromatography carried out on the supernatant, which leads to the obtaining of the recombinant DGL and/or the polypeptide (Δ54) and/or the polypeptide (Δ4) in an essentially pure form.

The invention also relates to any genetically transformed plant cell containing one (or more) recombinant nucleotide sequence(s) as described above, according to the invention, integrated into its genome in a stable manner.

The invention also relates to any transgenic plant cell as described above, containing one (or more) recombinant polypeptide(s) according to the invention, such as the recombinant DGL and/or the polypeptide (Δ54) and/or the polypeptide (Δ4) the said plant cell also being called a plant cell of enzymatic activity, and more particularly of lipase activity as defined below.

The invention also relates to genetically transformed seeds containing one (or more) recombinant nucleotide sequence(s) as described above, according to the invention, integrated into their genome in a stable manner.

The invention also relates to the transgenic seeds described above which contain one (or more) recombinant polypeptide(s) according to the invention, such as the recombinant DGL and/or the polypeptide (Δ54) and/or the polypeptide (Δ4), the said seeds also being called seeds of enzymatic activity, and more particularly of lipase activity as defined below.

The transformed seeds according to the invention are those harvested from genetically transformed plants according to the invention, these transformed plants being either those of the abovementioned generation TO and produced by culture of transformed cells according to the invention, or those of the following generations (T1, T2 etc.) obtained by autofertilization or by crossing plants of preceding generations (as indicated above).

The invention also relates to genetically transformed plants or parts of plants (in particular explants, stems, leaves, roots, pollen etc.), characterized in that they contain one (or more) recombinant nucleotide sequence(s) as described above, according to the invention, integrated into their genome in a stable manner.

The invention also relates to the transgenic plants or parts of plants described above containing one (or more) recombinant polypeptide(s) according to the invention, such as the recombinant DGL and/or the polypeptide (Δ54) and/or the polypeptide (Δ4), the said plants or parts of plants also being called plants or plant fragments of enzymatic activity, and more particularly of lipase activity as defined below.

The invention more particularly relates to the abovementioned transformed plants obtained by culture of cells or seeds as described above, according to the invention.

The transformed plants, or parts of plants, according to the invention are advantageously chosen from rape, tobacco, maize, pea, tomato, carrot, wheat, barley, potato, soya, sunflower, rice, lettuce and lucerne, or parts of these plants.

The present invention relates to any plant extract of enzymatic activity, and more particularly of lipase activity defined below, prepared by carrying out one of the processes of the invention described above, and containing, as active enzymes, one (or more) recombinant polypeptide(s) according to the invention, such as the recombinant DGL and/or the polypeptide (Δ54) and/or the polypeptide (Δ4).

The lipase (or lipolytic) activity of the plants or parts of plants and plant extracts of enzymatic activity of the invention, can be measured, in particular, in accordance with the method of Gargouri (Gargouri et al., 1986) using a short-chain triglyceride (such as tributyrin) as the substrate. The enzymatic activity is stated in units U, one unit U corresponding to the amount of enzyme required to liberate one $\mu$mol of free fatty acids per minute at 37° C. under optimum pH conditions.

The plant extracts of enzymatic activity of the invention are advantageously such that the percentage by weight of enzymatically active recombinant polypeptides is about 0.1% to 20%, in particular about 1% to about 15%, with respect to the total weight of proteins present in these extracts, which corresponds to measures of enzymatic activity from about 0.5 U per g of fresh weight (FW) of leaves to about 1,000 U/g of FW of leaves, in particular about U/g of FW to about 300 U/g of FW of leaves, or from about 1 U/g of FW of seeds to about 5,000 U/g of FW, in particular to about 10 U/g of FW of seeds to about 1,000 U/g of FW of seeds.

The invention more particularly relates to the following plant extracts of enzymatic activity:

the extracts of leaves and/or fruits and/or seeds of plants obtained by transformation of explant cells of these plants with the sequence pd35S-RGLSP-DGL or the sequence pd35S-PS-DGL or the sequence pd35S-PPS-DGL, according to one of the processes described above, and containing the recombinant DGL and/or the polypeptide (Δ54) and/or the polypeptide (Δ4), in particular:

the extract of tobacco leaves obtained by transformation of explant cells of tobacco leaves with the sequence pd35S-PS-DGL or the sequence pd35S-PPS-DGL, according to the process described above, and containing the polypeptide (Δ54) in combination with the polypeptide (Δ4), the percentage by weight by the mixture of these two polypeptides with respect to the total weight of proteins present in the said extract being from about 0.1 to about 20%, the enzymatic activity of the said extract being from about 100 U/g of FW to about 300 U/g of FW, the extract of tomato leaves or fruits obtained by transformation of explant cells of tomato leaves with the sequence pd35S-PS-DGL, or the sequence pd35S-PPS-DGL, according to the process described above, and containing the polypeptide (Δ54) in combination with the polypeptide (Δ4), the percentage by weight of this mixture of two polypeptides with respect to the total weight of proteins present in the said extract being from about 0.1% to about 20%, the enzymatic activity of the said extract being from about 100 U/g of FW to about 300 U/g of FW, the extract of tobacco leaves obtained by transformation of explant cells of tobacco leaves with the sequence pd35S-RGLSP-DGL, according to the process described above, and containing the polypeptide (Δ4), the percentage by weight of this polypeptide with respect to the total weight of proteins present in the said extract being from about 0.1% to about 20%, the enzymatic activity of the said extract being from about 100 U/g of FW to about 300 U/g of FW, the extract of tobacco seeds obtained by transformation of explant cells of tobacco leaves with the sequence pd35S-PS-DGL or the sequence pd35S-PPS-DGL, according to the process described above, and containing the polypeptide (Δ54), the percentage by weight of the polypeptide (Δ54) with respect to the total weight of proteins present in the said extract being from about 0.1% to about 1%, the enzymatic activity of the said extract being from about 10 U/g of FW to about 300 U/g of FW, the extracts of plant seeds obtained by transformation of explant cells of these plants with the sequence pCRU-PS-DGL or the sequence pCRU-PPS-DGL, or the sequence pGEA1-RGLSP-DGL, or the sequence pGEA6-RGLSP-DGL, according to one of the processes described above, and containing the recombinant DGL and/or the polypeptide (Δ54) and/or the polypeptide (Δ4), in particular:

the extract of rape seeds obtained by transformation of explant cells of rape leaves with the sequence pCRU-PS-DGL or the sequence pCRU-PPS-DGL, or the sequence pGEA1-RGLSP-DGL, or the sequence pGEA6-RGLSP-DGL, according to the process described above, and containing the polypeptide (Δ54), the percentage by weight of polypeptide (Δ54) with respect to the total weight of proteins present in the said extract being from about 0.1% to about 1%, the enzymatic activity of the said extract being from about 10 U/g of FW to about 1,000 U/g of FW, the extracts of plant seeds obtained by transformation of explant cells of these plants with the sequence pAR-IAR-RGLSP-DGL and/or the sequence pγzeine-RGLSP-DGL, and/or the sequence pγzeine-RGLSP-DGL-KDEL, according to one of the processes described above, and containing the recombinant DGL and/or the polypeptide (Δ54) and/or the polypeptide (Δ4), in particular:

the extract of corn seeds obtained by transformation of explant cells of rape leaves with the sequence pAR-IAR-RGLSP-DGL and/or the sequence pγzeine-RGLSP-DGL, and/or the sequence pγzeine-RGLSP-DGL-KDEL, according to the process described above, and containing the polypeptide (Δ54), the percentage by weight of polypeptide (Δ54) with respect to the total weight of proteins present in the said extract being from about 0.1% to about 1%, the enzymatic activity of the said extract being from about 10 U/g of FW to about 1,000 U/g of FW.

The present invention also relates to any enzymatically active recombinant DGL, the amino acid sequence of which is that shown on FIG. 2, or polypeptides derived from the latter, in particular by addition and/or suppression and/or substitution of one (or more) amino acid(s), these derived polypeptides having a lipase activity, such as are obtained in an essentially pure form by carrying out one of the processes of the invention described above, these processes comprising a stage of purification of the recombinant polypeptides of the invention, in particular by chromatography carried out on the enzymatic extracts described above.

As the polypeptides derived from the abovementioned recombinant DGL, the invention more particularly relates to the polypeptides (Δ54) and (Δ4) mentioned above, the molecular weights of which are, respectively, about 37 kDa and about 49 kDa.

Enzymatically active recombinant DGL or derived polypeptides having a lipase activity, as mentioned above, is understood as meaning any recombinant polypeptide which is capable of having a lipase activity as measured in accordance with the method of Gargouri mentioned above.

By way of illustration, the recombinant polypeptides according to the invention have a lipase activity of from about 10 U/mg of recombinant polypeptides to about 1,000 U/mg, advantageously from about 100 U/mg to about 600 U/mg.

The invention more particularly relates to the recombinant DGL obtained by purification of the enzymatic extract of tobacco leaves or seeds, these leaves or seeds originating from transformed tobacco plants, themselves obtained from tobacco cells transformed with the sequence pd35S-RGLSP-DGL according to the process described above, the said recombinant DGL having a lipase activity as described above.

The invention also relates to the polypeptide (Δ54) and the polypeptide (Δ4) obtained by purification of the enzymatic extract of plant leaves and/or seeds and/or fruits, notably solanaceae, such as transformed tobacco or tomato, themselves obtained from plant cells transformed with the sequence pd35S-PS-DGL or the sequence pd35S-PPS-DGL, or the sequence pd35S-RGLSP-DGL, according to the process described above, the said recombinant polypeptides (Δ54) and (Δ4) having a lipase activity as described above.

The invention also relates to the polypeptide (Δ54) obtained by purification of the enzymatic extract of tobacco seeds, or that of rape seeds, these seeds originating, respectively, from transformed tobacco or rape plants, themselves obtained, respectively, from tobacco or rape cells transformed with the sequence pCRU-PS-DGL or the sequence pCRU-PPS-DGL, according to the processes described above, the recombinant polypeptide (Δ54) having a lipase activity as described above.

The invention also relates to the polypeptide (Δ54) and the polypeptide (Δ4) obtained by purification of the enzymatic extract of rape seeds, these seeds originating from transformed rape plants, themselves obtained from rape cells transformed with the sequence pGEA1-RGLSP-DGL and/or the sequence pGEA6-RGLSP-DGL, according to the processes described above, the said recombinant polypeptides (Δ54) and (Δ4) having a lipase activity as described above.

The invention also relates to the polypeptide (Δ54) and the polypeptide (Δ4) obtained by purification of the enzymatic extract of corn seeds, these seeds originating from transformed corn plants, themselves obtained from corn cells transformed with the sequence pAR-IAR-RGLSP-DGL and/or the sequence pγzeine-RGLSP-DGL, and/or the sequence pγzeine-RGLSP-DGL-KDEL, according to the processes described above, the said recombinant polypeptides (Δ54) and (Δ4) having a lipase activity as described above.

The apparent molecular weights of the polypeptides (Δ54) and (Δ4) according to the invention are, respectively, 37 kDa and 49 kDa, measured by analysis in polyacrylamide gel and by immunodetection after electrotransfer on nitrocellulose (these methods being detailed in the embodiment examples of the invention which follow).

The invention relates to antibodies directed against the recombinant polypeptides of the invention, and more particularly those directed against the recombinant DGL according to the invention and/or against the abovementioned polypeptide (Δ54) and/or against the abovementioned polypeptide (Δ4), which can also recognize HGL.

Such antibodies can be obtained by immunization of an animal with these polypeptides, followed by recovery of the antibodies formed.

It goes without saying that this production is not limited to polyclonal antibodies.

It also applies to any monoclonal antibody produced by any hybridoma which can be formed by conventional methods from animal spleen cells, in particular from the mouse or rat, immunized against one of the purified polypeptides of the invention on the one hand, and cells of a suitable myeloma on the other hand, and which can be selected according to its capacity to produce monoclonal antibodies which recognize the abovementioned polypeptide initially used for immunization of the animals, as well as HGL.

The invention also relates to the use of transformed plants, plant parts, plant cells or seeds according to the invention for the preparation of one (or more) recombinant polypeptide(s) according to the invention, such as recombinant DGL or its derived polypeptides as defined above, in particular by carrying out one of the abovementioned processes of the invention, the said recombinant polypeptides being in an essentially pure form or contained in plant extracts of enzymatic activity as defined above.

The invention also relates to the use, in the field of human or animal foods, plants or parts of plants, of enzymatic activity according to the invention, or of plant extracts of enzymatic activity as defined above or of recombinant polypeptides according to the invention, such as the recombinant DGL or its derived polypeptides as defined above.

The invention more particularly relates to the use of plants or parts of plants, notably leaves, fruits, seeds of enzymatic activity according to the invention as foods.

In this respect, the invention more particularly relates to any food comprising a plant of enzymatic activity as described above or parts of this plant, notably leaves or fruits, or seeds produced by the latter, which can be of an edible character to man or animal.

The invention also relates to any alimentary composition comprising one (or more) plant(s) of enzymatic activity as described above and/or parts of this (these) plant(s) notably leaves and/or seeds and/or fruits of this (these) plants and/or one (or more) plant extract(s) of enzymatic activity as described above and/or one (or more) recombinant polypeptide(s) of the invention, where appropriate in combination with one (or more) other edible compound(s).

The plants or parts of plants contained in the abovementioned alimentary composition are advantageously in the form of ground material.

The foods according to the invention, also called functional foods, or the alimentary compositions according to the invention are more particularly intended to facilitate the absorption of animal or vegetable fats ingested by a healthy individual or an individual suffering from one or more pathologies which may or may not affect the level of production of gastric and/or pancreatic lipase. In this respect, the foods or alimentary compositions of the invention are advantageously used as nutritional supplements.

The invention also relates to the use of plants or parts of plants, notably leaves and/or fruits and/or seeds, or plant cells of enzymatic activity according to the invention, or plant extracts of enzymatic activity as defined above, or recombinant polypeptides according to the invention, such as the recombinant DGL or its derived polypeptides as defined above, for the preparation of medicaments (or pharmaceutical compositions) intended to facilitate the absorption of animal or vegetable fats ingested by a healthy individual or an individual suffering from one or more pathologies which may or may not affect the level of production of gastric and/or pancreatic lipase.

In particular, such pharmaceutical compositions are advantageously used on individuals undergoing medical treatment which changes the mechanism of absorption of fats, or on elderly persons.

The pharmaceutical compositions according to the invention are also more particularly intended for treatment of pathologies associated with lipase (in particular gastric and/or pancreatic lipase) insufficiency in the organism, and more particularly pathologies such as cystic fibrosis and exocrine pancreatic insufficiency.

The invention more particularly relates to any pharmaceutical composition comprising one (or more) plant extract(s) of enzymatic activity described above and/or one (or more) recombinant polypeptide(s) according to the invention, where appropriate in combination with a pharmaceutically acceptable vehicle.

The invention more particularly relates to any abovementioned pharmaceutical composition comprising the recombinant DGL and/or the polypeptide (Δ54) and/or the polypeptide (Δ4) in an essentially pure form or in the form of enzymatic extracts as described above.

The pharmaceutical compositions according to the invention can preferably be administered orally, and are, in particular, in the form of capsules, tablets or powders for dilution.

The daily dosage in humans is advantageously from about 200 mg to about 1,000 mg, preferably distributed over the main mealtimes, if the said pharmaceutical compositions comprise enzymatic extracts as described above, and from about 100 mg to about 500 mg if the said pharmaceutical compositions comprise the recombinant polypeptides according to the invention in an essentially pure form.

The invention also relates to the use of plants or parts of plants, notably leaves and/or fruits and/or seeds, or plant cells of enzymatic activity according to the invention, or plant extracts of enzymatic activity as defined above, or recombinant polypeptides according to the invention, such as the recombinant DGL or its derived polypeptides as defined above, for carrying out enzymatic reactions in the industrial, agro-alimentary or agro-industrial field, in particular in the fats industry, in lipochemistry and in the milk industry.

In this respect, the invention relates to any process, in particular of enzymatic bioconversion or of biocatalysis by carrying out one or more enzymatic reactions, in the industrial, agro-alimentary or agro-industrial field, in particular in the fats industry, in lipochemistry and in the milk industry, these enzymatic reactions being carried out by means of plants or parts of plants, notably leaves and/or fruits and/or seeds, or plant cells of enzymatic activity according to the invention, or plant extracts of enzymatic activity as defined above, or recombinant polypeptides according to the invention, such as the recombinant DGL or its derived polypeptides as defined above.

The invention more particularly relates to enzymatic preparations intended for industrial, agro-alimentary or agro-industrial use which can be used in the context of carrying out a process as described above and comprise one (or more) plant extract(s) of enzymatic activity as defined above, and/or one (or more) recombinant polypeptide(s) according to the invention, in particular the recombinant DGL and/or the polypeptide (Δ54) and/or the polypeptide (Δ4), where appropriate in combination with one (or more) additive(s) or other enzyme(s) which can be used in the context of the abovementioned industrial use.

The invention more particularly relates to the use of plants or parts of plants, notably leaves and/or fruits and/or seeds, or plant cells of enzymatic activity according to the invention, for carrying out, on an industrial scale, enzymatic bioconversion reactions or biocatalysis reactions, such as enzymatic hydrolyses or trans-esterifications.

The plants of enzymatic activity or parts of these plants, notably leaves and/or fruits and/or seeds, or plant cells according to the invention are advantageously used both as the enzymatic source and as the reactive substrate.

The invention also relates to any biocatalysis process which uses plants or parts of plants, notably leaves and/or fruits and/or seeds, or plant cells of enzymatic activity according to the invention, and more particularly plants containing the recombinant DGL and/or the polypeptide (Δ54) and/or the polypeptide (Δ4), the said plants or parts of plants, being used both as the enzymatic source and as the reactive substrate.

The invention more particularly relates to the use of plants of enzymatic activity or parts of these plants according to the invention for the preparation of biofuels.

In this respect, the present invention relates to any process for the preparation of a biofuel by addition of alcohol, in particular methanol or ethanol, to ground material of all or part of transformed plants according to the invention, advantageously ground material of transformed rape, sunflower or soya seeds according to the invention, and recovery of the biofuel, in particular by filtration.

The invention also relates to the esters of plant fatty acids such as are obtained by carrying out the abovementioned process, in particular the methyl ester of oleic acid.

The invention also relates to any biofuel obtained by carrying out a process as described above, and more particularly any abovementioned biofuel comprising esters of plant fatty acids.

The invention more particularly relates to any biofuel obtained by carrying out the abovementioned process on rape seeds and comprising a methyl ester of oleic acid.

The invention also relates to the use of the abovementioned antibodies directed against the recombinant polypeptides of the invention for carrying out a method for detection or assay of DGL or HGL in a biological sample which may contain it.

The invention more particularly relates to the use of these antibodies for carrying out a method for in vitro diagnosis of pathologies associated with excess production or, as the opposite, insufficiency, or even the absence of production, of lipase in the organism.

This method for in vitro diagnosis carried out on a biological sample taken from a patient comprises a stage of bringing this sample together with one or more antibodies according to the invention, followed by a stage of detection of any antibody-HGL complexes formed during the preceding stage.

In this respect, the invention also relates to a kit for carrying out an abovementioned method of in vitro detection or diagnosis comprising:

antibodies as described above, advantageously labelled in a radioactive or enzymatic manner, and reagents for constitution of a medium favourable for carrying out the immunological reaction between these antibodies and the HGL, reagents which allow detection of immunological complexes formed between these antibodies and the HGL.

The present invention more particularly relates to the use of a recombinant nucleotide sequence containing on the one hand, the cDNA shown on FIG. 4 and which codes for the human gastric lipase (HGL) shown on FIG. 5, or a nucleotide sequence derived from this cDNA, in particular by addition and/or suppression and/or substitution of one (or more) nucleotide(s), the said derived sequence being capable of coding for a polypeptide, the amino acid sequence of which is identical to that of the HGL shown on FIG. 5, or for a polypeptide derived from the HGL by addition and/or suppression and/or substitution of one (or more) amino acid(s), this derived polypeptide having a lipase activity, and, on the other hand, elements which allow a plant cell to produce the polypeptide coded by the said cDNA or by an abovementioned derived sequence, in particular a transcription promoter and a transcription terminator recognized by the transcription machinery of plant cells (and more particularly by the RNA polymerases of the latter), for transformation of plant cells in order to obtain, from these cells or plants obtained from the latter, recombinant DGL in active enzyme form or one (or more) polypeptide(s) derived from the latter as defined above.

In this respect, the invention relates to any recombinant nucleotide sequence as described above in the context of the transformation of plants with a view to the preparation of recombinant DGL, in which the nucleotide sequence which codes for the DGL and shown on FIG. 1 or FIG. 3, is replaced by the nucleotide sequence which codes for the HGL and shown on FIG. 4.

The invention more particularly relates to the following recombinant nucleotide sequences:

that (called pSP-HGLSP-HGL) containing, in the direction 5'→3', the promoter pSP of *Agrobacterium tumefaciens*, the sequence which codes for the signal peptide of HGL, the latter being immediately followed by the nucleotide sequence shown on FIG. 4, and then the terminator polyA 35S of CaMV, that (called pSP-HPLSP-HGL) containing, in the direction 5'→3', the promoter pSP of *Agrobacterium tumefaciens*, the sequence which codes for the signal peptide of HPL, the latter being immediately followed by the nucleotide sequence shown on FIG. 4, and then the terminator polyA 35S of CaMV, that (called pSP-RGLSP-HGL) containing, in the direction 5'→3', the promoter pSP of *Agrobacterium tumefaciens*, the sequence which codes for part of the signal peptide of RGL (as described above), the latter being immediately followed by the nucleotide sequence shown on FIG. 4, and then the terminator polyA 35S of CaMV.

The invention also relates to the vectors and cellular hosts transformed by these vectors, as described above, and containing the abovementioned recombinant nucleotide sequences which code for the HGL and/or its derived polypeptides.

The present invention also relates to any process for the preparation of recombinant HGL in active enzyme form and/or of one (or more) polypeptide(s) derived from the latter, in particular by addition and/or suppression and/or substitution of one (or more) amino acid(s), this (or these) derived polypeptide(s) having a lipase activity, characterized in that it comprises:

transformation of plant cells such that one (or more) recombinant nucleotide sequence(s) according to the invention is (or are) integrated into the genome of these cells, where appropriate, production of transformed plants from the abovementioned transformed cells, recovery of the recombinant HGL and/or of the abovementioned derived polypeptide(s) produced in the said cells or abovementioned transformed plants, in particular by extraction, followed, where appropriate, by purification.

The invention more particularly relates to any production process for recombinant HGL by the implementation of a process as described above in the context of the production of recombinant DGL and/or its derived polypeptides using an abovementioned recombinant sequence containing the sequence shown on FIG. 4.

Among the polypeptides derived from the recombinant HGL which can be obtained in the context of carrying out a process according to the invention there may be mentioned:

the polypeptide delimited by the amino acids situated in positions 74 and 398 in FIG. 5, also called polypeptide (Δ54HGL), the polypeptide delimited by the amino acids situated in positions 24 and 398 in FIG. 5, also called polypeptide (Δ4HGL).

The invention more particularly relates to a process for the preparation, as described above, of the recombinant HGL and/or the polypeptide (Δ54HGL) and/or the polypeptide (Δ4HGL), characterized in that it comprises:

transformation of explant cells of the leaves of a plant by bringing the latter together with a strain of *Agrobacterium tumefaciens* transformed by a plasmid as described above containing the abovementioned recombinant nucleotide sequence pSP-HGLSP-HGL and/or pSP-HPLSP-HGL and/or pSP-RGLSP-HGL, on a suitable culture medium, selection of the transformed explants on a medium containing kanamycin, production of transformed plants from the abovementioned transformed explants by culture of the latter on suitable media, extraction of the recombinant HGL and/or the polypeptide (Δ54HGL) and/or the polypeptide (Δ4HGL), in particular by grinding the leaves and/or the seeds and/or the fruits of the abovementioned transformed plants in a suitable buffer, centrifuging and recovery of the supernatant constituting the plant extract of enzymatic activity, where appropriate, purification of the recombinant HGL and/or the polypeptide (Δ54HGL) and/or the polypeptide (Δ4HGL) from the extract obtained during the preceding stage, in particular by chromatography carried out on the supernatant, which leads to the preparation of the recombinant HGL and/or the polypeptide (Δ54HGL) and/or the polypeptide (Δ4HGL) in an essentially pure form.

The invention also relates to any plant or part of this plant, notably leaves and/or fruits and/or seeds, containing one (or more) recombinant nucleotide sequence(s) as described above, according to the invention, integrated into its genome in a stable manner.

The present invention relates to any plant extract of enzymatic activity, and more particularly of lipase activity defined below, prepared by carrying out one of the processes of the invention described above, and containing, as active enzymes, one (or more) recombinant polypeptide(s) according to the invention, such as the recombinant HGL and/or the polypeptide (Δ54HGL) and/or the polypeptide (Δ4HGL).

The invention more particularly relates to extracts of leaves and/or seeds of plants, as obtained by the transformation of explant cells of these plants with the sequence pSP-HGLSP-HGL, or the sequence pSP-HPLSP-HGL, or the sequence pSP-RGLSP-HGL, according to one of the processes described above, and containing the recombinant HGL, and/or the polypeptide (Δ54HGL), and/or the polypeptide (Δ4HGL), in particular:

the extract of tobacco leaves or seeds as obtained by transformation of explant cells of tobacco leaves with the sequence pSP-HGLSP-HGL, or the sequence pSP-HPLSP-HGL, or the sequence pSP-RGLSP-HGL according to the process described above, and containing the polypeptide (Δ54HGL), in combination with the polypeptide (Δ4HGL), the percentage by weight of the mixture of these two polypeptides with respect to the total weight of proteins present in the said extract being from about 0.1% to about 20%, the enzymatic activity of the said extract being from about 100 U/g of FW to about 300 U/g of FW, the extract of tobacco leaves as obtained by transformation of explant cells of tobacco leaves with the sequence pSP-RGLSP-HGL, and containing the polypeptide (Δ4HGL), the percentage by weight of this polypeptide with respect to the total weight of proteins present in the said extract being from about 0.1% to about 20%, the enzymatic activity of the said extract being from about 100 U/g of FW to about 300 U/g of FW.

The present invention also relates to any enzymatically active recombinant HGL, the amino acid sequence of which is that shown on FIG. 5, or polypeptides derived from the latter, in particular by addition and/or suppression and/or substitution of one (or more) amino acid(s), and more particularly the polypeptides (Δ54HGL) and (Δ4HGL), these derived polypeptides having a lipase activity, such as are obtained in an essentially pure form by carrying out one of the processes of the invention described above, these processes comprising a stage of purification of the recombinant polypeptides of the invention, in particular by chromatography carried out on the enzymatic extracts described above.

As has been described previously in the context of the recombinant DGL, the invention also relates to:

the polyclonal or monoclonal antibodies directed against the recombinant HGL or its derived polypeptides according to the invention, and their uses as described above, foods or alimentary compositions or pharmaceutical compositions, or enzymatic preparations for industrial purposes based on plants, or parts of plants, notably leaves and/or fruits and/or seeds, or plant cells or extracts of enzymatic activity as defined above, or also recombinant HGL or its derived polypeptides according to the invention, any enzymatic bioconversion process or biocatalysis, or biofuel preparation as described above, carried out from recombinant HGL or its derived polypeptides according to the invention, or plants, or parts of plants, notably leaves and/or fruits and/or seeds and/or plant extracts of enzymatic activity as defined above.

The invention will be illustrated further in the detailed description which follows for the preparation of recombinant nucleotide sequences as described above and transformed plants which produce the recombinant polypeptides according to the invention, and for a process for the preparation of a biofuel.

1. Construction of Chimaeric Genes which Code for the Recombinant Protein of Dog Gastric Lipase and Allow Expression in the Leaves and Seeds of Solanaceae I-A) Construction of Chimaeric Genes which Code for the Recombinant DGL and Allow Expression in Tobacco Expression in tobacco leaves and seeds of the gene which codes for dog gastric lipase (DGL) requires the following regulator sequences:

1. The double-structured promoter 35S (pd35S) of CaMV (cauliflower mosaic virus).

This corresponds to duplication of the sequences which activate transcription and are situated upstream of the TATA element of the natural promoter 35S (Kay et al., 1987);

2. The terminal transcription sequence, terminator polyA 35S, which corresponds to the non-coding region 3' of the sequence of the cauliflower mosaic virus, of double-stranded circular DNA, which produces the transcript 35S (Franck et al., 1980).

The constructions of the various plasmids via the use of recombinant DNA techniques (Sambrook et al., 1989) are derived from pBIOC4. This binary plasmid is derived from pGA492 (An, 1986), which contains, between the right and left borders, the following sequences originating from the plasmid pTiT37 of *Agrobacterium tumefaciens,* on its transfer DNA:

The structural promoter of the nos gene which codes for nopaline synthase (Depicker et al., 1982), the sequence which codes for the nptII gene which codes for neomycin phosphotransferase II (Berg and Berg, 1983) deleted from the region of the first 8 codons, of which the initiator codon is methionine ATG, and fused to the sequence of the first 14 codons of the sequence which codes for the nos gene (Depicker et al., 1982), the sequence which codes for the nos gene devoid of the region of the first 14 codons, the nos terminator (Depicker et al., 1982), a region containing multiple cloning sites (also called polylinker) (HindIII-XbaI-SacI-HpaI-KpnI-ClaI-BglII) preceding the cat gene which codes for chloramphenicol acetyltransferase (Close and Rodriguez, 1982) and the terminal sequences of the gene 6 of the plasmid pTiA6 of *Agrobacterium tumefaciens* (Liu et al., 1993). To eliminate virtually all the sequence which codes for the cat gene, the plasmid pGA492 was digested twice by SacI (restriction site of the polylinker) and by ScaI (restriction site present in the sequence of the cat gene) and then subjected to the action of the enzyme T4 DNA polymerase (New England Biolabs) in accordance with the manufacturer's instructions. The ligation of the modified plasmid (ng) was carried out in a reaction medium of 10 µl comprising 1 µl of the buffer T4 DNA ligase×10 (Amersham); 2.5 U of the enzyme T4 DNA ligase (Amersham) at 14° C. for 16 hours. The bacteria *Escherichia coli* DH5α, rendered competent beforehand, were transformed (Hanahan, 1983). The plasmid DNA of the clones obtained, selected on 12 µg/ml of tetracycline, was extracted by the alkaline lysis method (Birnboim and Doly, 1979) and analysed by enzymatic digestion by restriction enzymes. The HindIII restriction site of the plasmid DNA of the clone retained was then modified into an EcoRI restriction site with the aid-of an phosphorylated HindIII-EcoRI adaptor (Stratagene Cloning Systems). To carry out this modification, 500 ng of plasmid DNA of the clone retained were digested by HindIII, dephosphorylated by the alkaline phosphatase enzyme of the intestine of the calf (Boehringer Mannheim) in accordance with the manufacturer's instructions and coprecipitated in the presence of 1,500 ng of the HindIII-EcoRI DNA adaptor, 1/10 volume of 3M sodium acetate, pH 4.8, and 2.5 volumes of to absolute ethanol at −80° C. for min. After centrifugation at 12,000 g for min, the DNA precipitated was washed with 70% ethanol, dried, taken up in 8 µl of water, kept at 65° C. for min and then ligated in the presence of 1 µl of the buffer T4 DNA ligase×10 (Amersham) and 2.5 U of the enzyme T4 DNA ligase (Amersham) at 14° C. for 16 hours. After inactivation of the T4 DNA ligase at 65° C. for min, the ligation reaction mixture was digested by EcoRI, purified by electrophoresis over 0.8% agarose gel, electroeluted (Sambrook et al., 1989), precipitated in the presence of 1/10 volume of 3M sodium acetate, pH 4.8, and 2.5 volumes of absolute ethanol at −80° C. for min, centrifuged at 12,000 g for 30 min, washed with 70% ethanol, dried and then ligated as described above. The bacteria *Escherichia coli* DH5α, rendered competent beforehand, were transformed (Hanahan, 1983). The plasmid DNA of the clones obtained, selected on 12 µg/ml of tetracycline, was extracted by the alkaline lysis method (Birnboim and Doly, 1979) and analysed by enzymatic digestion by HindIII and EcoRI in particular. The resulting binary plasmid, which only has the last 9 codons of the sequence which codes for the cat gene and of which the EcoRI site is unique, was called pBIOC4.

The expression cassette made up of the promoter pd35S and the terminator polyA 35S was isolated using the plasmid pJIT163Δ. The plasmid pJIT163Δ is derived from the plasmid pJIT163, which itself is derived from the plasmid pJIT60 (Guerineau and Mullineaux, 1993). The plasmid pJIT163 possesses an ATG codon between the HindIII and SalI sites of the polylinker. To suppress this ATG and to obtain the plasmid pJIT163Δ, the plasmid pJIT163 DNA was digested twice by HindIII and SalI, purified by electrophoresis over 0.8% agarose gel, electroeluted (Sambrook et al., 1989), precipitated in the presence of 1/10 volume of 3M sodium acetate, pH 4.8, and 2.5 volumes of absolute ethanol at −80° C for min, centrifuged at 12,000 g for 30 min, washed with 70% ethanol, dried, subjected to the action of Klenow enzyme (New England Biolabs) in accordance with the manufacturer's instructions, deproteinated by extraction with 1 volume of phenol:chloroform:isoamyl alcohol (25:24:1) and then 1 volume of chloroform:isoamyl alcohol (24:1), precipitated in the presence of 1/10 volume of 3M sodium acetate, pH 4.8, and 2.5 volumes of absolute ethanol at −80° C for 30 min, centrifuged at 12,000 g for 30 min, washed with 70% ethanol, dried and, finally, ligated in the presence of 1 µl of the buffer T4 DNA ligase×10 (Amersham) and 2.5 U of the enzyme T4 DNA ligase (Amersham) at 14° C. for 16 hours. The bacteria *Escherichia coli* DH5α, rendered competent beforehand, were transformed (Hanahan, 1983). The plasmid DNA of the clones obtained, selected on 50 µg/ml of ampicillin, was extracted by the alkaline lysis method (Birnboim and Doly, 1979) and analysed by enzymatic digestion by restriction enzymes. To isolate the expression cassette made up of the promoter pd35S and the terminator polyA 35S (SacI-XhoI fragment), the plasmid DNA of the clone pJIT163Δ retained was digested by SacI and XhoI. The SacI-XhoI fragment, carrying the expression cassette, was purified by electrophoresis over 0.8% agarose gel, electroeluted (Sambrook et al., 1989), precipitated in the presence of 1/10 volume of 3M sodium acetate, pH 4.8, and 2.5 volumes of absolute ethanol at −80° C. for 30 min, centrifuged at 12,000 g for 30 min, washed with 70% ethanol, dried and then subjected to the action of Mung Bean Nuclease enzyme (New England Biolabs) in accordance with the manufacturer's instructions. This purified insert (200 ng) was cloned in the plasmid DNA of pBIOC4 (20 ng), which had been digested by EcoRI, treated with the enzyme Mung Bean Nuclease and dephosphorylated by the alkaline phosphatase enzyme of the intestine of the calf (Boehringer Mannheim) in accordance with the manufacturer's instructions. The ligation reaction was carried out in 20 µl in the presence of 2 µl of the buffer T4 DNA ligase×10 (Amersham), 2 µl of 50% polyethylene glycol 8000 and 5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 12 µl/ml of tetracycline, was extracted by the alkaline lysis method (Birnboim and Doly, 1979) and analysed by enzymatic digestion by restriction enzymes. The resulting plasmid was called pBIOC21.

Dog gastric lipase (DGL) is synthesized naturally in the form of a precursor. The mature DGL protein is made up of 379 amino acids. The complementary DNA of DGL was cloned at the BglII and SalI sites of the expression vector pRU303, leading to the vector pDGL5.303 described in the international application no. WO 94/13816. It was used for construction of the binary plasmids pBIOC25, containing PS-DGL, and pBIOC26, containing PPS-DGL, where the sequence which codes for the mature DGL is preceded by that which codes for a signal peptide (PS) or a prepropeptide (PPS, that is to say a signal peptide followed by N-terminal vacuole-directing sequences) of plant origin respectively. The PS and PPS sequences, made up, respectively, of 23 and 37 amino acids, are those of a reserve protein of the tuberous roots of the sweet potato: sporamin A (Murakami et al., 1986; Matsukoa and Nakamura, 1991).

To simplify fusions between the sequence of mature DGL and that of the directing signals, PS or PPS, the plasmid pDGL5.303 was modified by introduction of a supplementary HindIII restriction site into the fourth and fifth codons of the mature DGL sequence by mutagenesis directed by PCR using 2 oligodeoxynucleotides, 5' caggagatc TTG TTT GGA AAG CTT CAT CCC 3'(SEQ ID NO: 10) (containing the unique BglII site in the plasmid and providing the supplementary HindIII site) and 5' CAT ATT CCT CAG CTG GGT ATC 3'(SEQ ID NO: 11) (containing the unique PvuII site in the plasmid). Amplification of the BglII-PvuII fragment by PCR was carried out in 100 µl of reaction medium comprising 10 µl of the buffer Taq DNA polymerase×10 (500 mM KCl, 100 mM Tris-HCl, pH 9.0, and 1% Triton×100), 6 µl of 25 mM MgCl$_2$, 3 µl of 10 mM dNTP (dATP, dCTP, dGTP and dTTP), 100 pM of each of the 2 oligodeoxynucleotides described above, 5 ng of matrix DNA (expression vector pRU303 including the complementary DNA of DGL), 2.5 U of Taq DNA polymerase (Promega) and 2 drops of vaseline oil. The DNA was denatured at 94° C. for 30 min, subjected to 30 cycles, each of 1 min of denaturation at 94° C., 1 min of hybridization at 50° C. and 1 min of elongation at 72° C., and then elongation at 72° C. was continued for min. This PCR reaction was carried out in the "DNA Thermal Cycler" machine of PERKIN ELMER CETUS. The oil was removed by extraction with chloroform. The DNA fragments contained in the reaction medium were then precipitated in the presence of 1/10 volume of 3M sodium acetate, pH 4.8, and 2.5 volumes of absolute ethanol at −80° C. for 30 min, centrifuged at 12,000 g for 30 min, washed with 70% ethanol, dried and digested by the 2 restriction enzymes BglII and PvuII. The digested DNA fragments originating from the PCR were purified by electrophoresis over 2% agarose gel, electroeluted (Sambrook et al., 1989), precipitated in the presence of 1/10 volume of 3M sodium acetate, pH 4.8, and 2.5 volumes of absolute ethanol at −80° C. for 30 min, centrifuged at 12,000 g for 30 min, washed with 70% ethanol, dried and then ligated to the plasmid DNA of the vector pDGL5.303, which had been digested twice by BglII and PvuII, purified by electrophoresis over 0.8% agarose gel, electroeluted, subjected to precipitation in alcohol, dried and dephosphorylated by the alkaline phosphatase enzyme of the intestine of the calf (Boehringer Mannheim) in accordance with the manufacturer's instructions. The ligation was carried out with 100 ng of the dephosphorylated vector described above and 50 ng of the digested DNA fragments, originating from the amplification by PCR, described above in a reaction medium of 10 µl in the presence of 1 µl of the buffer T4 DNA ligase×10 (Amersham) and 2.5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 50 µg/ml of ampicillin, was extracted by the alkaline lysis method (Birnboim and Doly, 1979) and analysed by enzymatic digestion by restriction enzymes. The plasmid DNA of some of the clones retained was verified by sequencing with the aid of the T7™ sequencing kit, marketed by Pharmacia, by the dideoxynucleotide method (Sanger et al., 1977). Introduction of this HindIII restriction site does not modify the genetic code of the DGL. In fact, the natural DGL sequence AAA TTA (Lys-Leu) becomes AAG CTT (Lys-Leu). The resulting plasmid was called pBIOC22 and includes the sequence of the mature DGL protein corresponding to:

| LEU PHE GLY LYS LEU------THR ASP ASN LYS AMB (SEQ ID NO: 12) | | |
|---|---|---|
| agatc TTG TTT GGA AAGCTT------ACA GAT AAT AAG TAG TTCTAGA (SEQ ID NO: 13) | | |
| BglII<br>unique restriction site | HindIII | XbaI<br>unique restriction site |

LEU: first codon of the mature DGL, AMB: Stop codon.

a. Construction of the Binary Plasmid pBIOC25 Containing PS-DGL

The plasmid pBIOC22 was digested totally by BglII and partly by HindIII in order to suppress the sequence which codes for the polypeptide Leu-Phe-Gly-Lys (first 4 amino acids) of the mature DGL protein. This sequence was replaced by that which codes for the signal peptide PS of 23 amino acids (ATG AAA GCC TTC ACA CTC GCT CTC TTC TTA GCT CTT TCC CTC TAT CTC CTG CCC AAT CCA GCC CAT TCC) (SEQ ID NO: 14) fused to that of the first 4 codons of the sequence which codes for the mature DGL protein ("PS-first 4 codons of mature DGL"). The sequence "PS-first 4 codons for mature DGL" was amplified by PCR using the plasmid pMAT103 (Matsuoka and Nakamura, 1991) with the aid of the 2 following oligodeoxynucleotides 5' caggagatctgATG AAA GCC TTC ACA CTC GC 3'(SEQ ID NO: 15) and 5' ATG AAG CTT TCC AAA CAA GGA ATG GGC TGG ATT GGG CAG G 3'(SEQ ID NO: 16), in accordance with the protocol of PCR amplification described above in paragraph I. After double enzymatic digestion by BGlII and HindIII, the DNA fragments originating from the PCR amplification were purified by electrophoresis over 2% agarose gel, electroeluted (Sambrook et al., 1989), precipitated in the presence of 1/10 volume of 3M sodium acetate, pH 4.8, and 2.5 volumes of absolute ethanol at −80° C. for 30 min, centrifuged at 12,000 g for 30 min, washed with 70% ethanol, dried and then ligated to the plasmid DNA of pBIOC22, which had been doubly digested by BglII and HindIII, purified by electrophoresis over 0.8% agarose gel, electroeluted (Sambrook et al., 1989), subjected to precipitation with alcohol, dried and dephosphorylated by the alkaline phosphatase enzyme of the intestine of the calf (Boehringer Mannheim) in accordance with the manufacturer's instructions. The ligation was carried out with 100 ng of the dephosphorylated vector described above and 50 ng of the digested DNA fragments, originating from the PCR amplification, described above in a reaction medium of 10 µl in the presence of 1 µl of the buffer T4 DNA ligase×10 (Amersham) and 2.5 U of the enzyme T4 DNA ligase (Amersham) at 14° C. for 16 hours. The bacteria *Escherichia coli* DH5α, rendered competent beforehand, were transformed (Hanahan, 1983). The plasmid DNA of the clones obtained, selected on 50 µg/ml of ampicillin, was extracted by the alkaline lysis method (Birnboim and Doly, 1979) and analysed by enzymatic digestion by restriction enzymes. The plasmid DNA of some of the clones retained was verified by sequencing with the aid of the T7™ sequencing kit, marketed by Pharmacia, by the dideoxynucleotide method (Sanger et al., 1977). The sequences of the PS and the mature DGL were cloned, maintaining their open-reading frames. The cleavage sequence between the sequences of the PS and the mature DGL is Ser-Leu. The resulting plasmid was called pBIOC23. Starting from pBIOC23, the BglII-XbaI fragment carrying the sequence of PS-DGL was isolated by double enzymatic digestion by BglII and XbaI, purification by electrophoresis over 0.8% agarose gel, electroelution (Sambrook et al., 1989), precipitation with alcohol and drying. This DNA fragment was then treated with Klenow enzyme in accordance with the manufacturer's instructions and ligated to the plasmid DNA of pBIOC21, which had been digested at the HindIII site, treated with Klenow and dephosphorylated by the alkaline phosphatase enzyme of the intestine of the calf (Boehringer Mannheim) in accordance with the manufacturer's instructions. The ligation was carried out with 20 ng of the dephosphorylated vector described above and 200 ng of DNA fragments, containing the PS-DGL, described above in a reaction medium of 20 µl in the presence of 2 µl of the buffer T4 DNA ligase×10 (Amersham), 2 µl of 50% polyethylene glycol 8000 and 5 U of the enzyme T4 DNA ligase (Amersham) at 14° C. for 16 hours. The bacteria *Escherichia coli* DH5α, rendered competent beforehand, were transformed (Hanahan, 1983). The plasmid DNA of the clones obtained, selected on 12 µg/ml of tetracycline, was extracted by the alkaline lysis method (Birnboim and Doly, 1979) and analysed by enzymatic digestion by restriction enzymes. The resulting clone was called pBIOC25. The nucleotide sequence of the fragment which codes for the recombinant protein PS-DGL was verified by sequencing with the aid of the T7™ sequencing kit, marketed by Pharmacia, by the dideoxynucleotide method (Sanger et al., 1977). The plasmid DNA of the binary vector pBIOC25 was introduced by direct transformation into the strain LBA4404 of *Agrobacterium tumefaciens* in accordance with the process of Holsters et al. (1978). The validity of the clone retained was verified by enzymatic digestion of the plasmid DNA introduced.

b. Containing of the Binary Plasmid pBIOC26 Containing PPS-DGL

The plasmid pBIOC22 was digested totally by BglII and partly by HindIII in order to suppress the sequence which codes for the polypeptide Leu-Phe-Gly-Lys (first 4 amino acids) of the mature DGL protein. This sequence was replaced by that which codes for the signal peptide PS of 23 amino acids (ATG AAA GCC TTC ACA CTC GCT CTC TTC TTA GCT CTT TCC CTC TAT CTC CTG CCC AAT CCA GCC CAT TCC AGG TTC AAT CCC ATC CGC CTC CCC ACC ACA CAC GAA CCC GCC) (SEQ ID NO: 17) fused to that of the first 4 codons of the sequence which codes for the mature DGL protein ("PPS-first 4 codons of mature DGL"). The sequence "PPS-first 4 codons for mature DGL" was amplified by PCR using the plasmid pMAT103 (Matsuoka and Nakamura, 1991) with the aid of the 2 following oligodeoxynucleotides 5' caggagatctgATG AAA GCC TTC ACA CTC GC 3'(SEQ ID NO: 15) and 5' ATG AAG CTT TCC AAA CAA GGA GGG TTC GTG TGT GGT TG 3' (SEQ ID NO: 18), in accordance with the protocol of PCR amplification described above in paragraph I. After double enzymatic digestion by BGlII and HindIII, the DNA fragments originating from the PCR amplification were purified by electrophoresis over 2% agarose gel, electroeluted (Sambrook et al., 1989), precipitated in the presence of 1/10 volume of 3M sodium acetate, pH 4.8, and 2.5 volumes of absolute ethanol at −80° C. for 30 min, centrifuged at 12,000 g for 30 min, washed with 70% ethanol, dried and then ligated to the plasmid DNA of pBIOC22, which had been doubly digested by BglII and HindIII, purified by electrophoresis over 0.8% agarose gel, electroeluted, subjected to precipitation with alcohol, dried and dephosphorylated by the alkaline phosphatase enzyme of the intestine of the calf (Boehringer Mannheim) in accordance with the manufacturer's instructions. The ligation was carried out with 100 ng of the dephosphorylated vector described above and 50 ng of the digested DNA fragments, originating from the PCR amplification, described above in a reaction medium of 10 µl in the presence of 1 µl of the buffer T4 DNA ligase×10 (Amersham) and 2.5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 50 µg/ml of ampicillin, was extracted by the alkaline lysis method (Birnboim and Doly, 1979) and analysed by enzymatic digestion by restriction enzymes.

The plasmid DNA of some of the clones retained was verified by sequencing with the aid of the T7™ sequencing kit, marketed by Pharmacia, by the dideoxynucleotide method (Sanger et al., 1977). The sequences of the PPS and the mature DGL were cloned, maintaining their open-reading frames. The cleavage sequence between the two sequences is Ala-Leu. The resulting plasmid was called pBIOC24. Starting from pBIOC24, the BglII-XbaI fragment carrying the sequence of PPS-DGL was isolated by double enzymatic digestion by BglII and XbaI, purified by electrophoresis over 0.8% agarose gel, electroeluted (Sambrook et al., 1989), precipitated with alcohol and dried. This DNA fragment was then treated with Klenow enzyme in accordance with the manufacturer's instructions and ligated to the plasmid DNA of pBIOC21, which had been digested at the HindIII site, treated with Klenow and dephosphorylated by the alkaline phosphatase enzyme of the intestine of the calf (Boehringer Mannheim) in accordance with the manufacturer's instructions. The ligation was carried out with 20 ng of the dephosphorylated vector described above and 200 ng of DNA fragments, containing the PPS-DGL, described above in a reaction medium of 20 µl in the presence of 2 µl of the buffer T4 DNA ligase×10 (Amersham), 2 µl of 50% polyethylene glycol 8000 and 5 U of the enzyme T4 DNA ligase (Amersham) at 14° C. for 16 hours. The bacteria *Escherichia coli* DH5α, rendered competent beforehand, were transformed (Hanahan, 1983). The plasmid DNA of the clones obtained, selected on 12 μg/ml of tetracycline, was extracted by the alkaline lysis method (Birnboim and Doly, 1979) and analysed by enzymatic digestion by restriction enzymes. The resulting clone was called pBIOC26. The nucleotide sequence of the fragment which codes for the recombinant protein PPS-DGL was verified by sequencing with the aid of the T7™ sequencing kit, marketed by Pharmacia, by the dideoxynucleotide method (Sanger et al., 1977). The plasmid DNA of the binary vector pBIOC26 was introduced by direct transformation into the strain LBA4404 of *Agrobacterium tumefaciens* in accordance with the process of Holsters et al. (1978). The validity of the clone obtained was verified by enzymatic digestion of the plasmid DNA introduced.

c. Containing of the Binary Plasmid pBIOC41 Containing RGLSP-DGL

Rabbit gastric lipase is synthesized in the form of a precursor composed of a signal peptide of 22 amino acids situated at the $NH_2$-terminal end and preceding the polypeptide sequence of the mature lipase. The clone pJO101 containing the complete cDNA which codes for rabbit gastric lipase is described in European Patent Application no. 92 403 055.4 filed on Dec. 11, 1992 by "Institut de Recherche Jouveinal" and entitled "Nucleic acids which code for rabbit gastric lipase and polypeptide derivatives, their use for the production of these polypeptides, and pharmaceutical compositions based on the latter".

Alignment of the polypeptide sequences of dog gastric lipase and of the precursor of rabbit gastric lipase has demonstrated that the sequence LFGK is present in the two proteins. In the polypeptide sequence of the rabbit lipase determined from the purified natural protein (Moreau et al., 1988), the first three residues L, F and G are absent and form part of the signal peptide of 22 amino acids of RGL. As a result, the signal peptide of rabbit gastric lipase devoid of these three common amino acids was fused to the mature protein sequence of dog gastric lipase. Its polypeptide sequence is made up of the following 19 amino acids: MWVLFMVAALLSALGTTHG (SEQ ID NO: 19). The plasmid pBIOC22 was thus digested totally by BhlI and partly by HindIII in order to suppress the sequence which codes for the polypeptide Leu-Phe-Gly-Lys (first 4 amino acids) of the mature DGL protein. This sequence was replaced by that which codes for the signal peptide RGLSP of rabbit gastric lipase of 19 amino acids (ATG TGG GTG CTT TTC ATG GTG GCA GCT TTG CTA TCT GCA CTT GGA ACTACA CAT GGT) (SEQ ID NO: 20) fused to that of the first 4 codons of the mature DGL protein ("RGLSP-first 4 codons of mature DGL"). The sequence "RGLSP-first 4 codons of mature DGL" was amplified by PCR using the plasmid pJO101 with the aid of the 2 following oligodeoxynucleotides 5' aggagatctcaacaATG TGG GTG CTT TTC ATG GTG 3' (SEQ ID NO: 21) and 5' G ATG AAG CTT TCC AAA CAA ACC ATG TGT AGT TCC AAG TG 3' (SEQ ID NO: 22), in accordance with the protocol of PCR amplification described above in paragraph I. After double enzymatic digestion by BGlII and HindIII, the DNA fragments originating from the PCR amplification were purified by electrophoresis over 2% agarose gel, electroeluted (Sambrook et al., 1989), precipitated in the presence of 1/10 volume of 3M sodium acetate, pH 4.8, and 2.5 volumes of absolute ethanol at −80° C. for 30 min, centrifuged at 12,000 g for 30 min, washed with 70% ethanol, dried and then ligated to the plasmid DNA of pBIOC22, which had been doubly digested by BglII and HindIII, purified by electrophoresis over 0.8% agarose gel, electroeluted (Sambrook et al., 1989), subjected to precipitation with alcohol, dried and dephosphorylated by the alkaline phosphatase enzyme of the intestine of the calf (Boehringer Mannheim) in accordance with the manufacturer's instructions. The ligation was carried out with 100 ng of the dephosphorylated vector described above and 50 ng of the digested DNA fragments, originating from the PCR amplification, described above in a reaction medium of 10 μl in the presence of 1 μl of the buffer T4 DNA ligase×10 (Amersham) and 2.5 U of the enzyme T4 DNA ligase (Amersham) at 14° C. for 16 hours. The bacteria *Escherichia coli* DH5α, rendered competent beforehand, were transformed (Hanahan, 1983). The plasmid DNA of the clones obtained, selected on a medium containing 50 μg/ml of ampicillin, was extracted by the alkaline lysis method (Birnboim and Doly, 1979) and analysed by enzymatic digestion by restriction enzymes. The plasmid DNA of some of the clones retained was verified by sequencing with the aid of the $T_7$™ sequencing kit, marketed by Pharmacia, by the dideoxynucleotide method (Sanger et al., 1977). The sequences of the RGLSP and the mature DGL were cloned, maintaining their open reading frames (that is to say such that they constitute a unique open reading frame). The cleavage sequence between the sequences of the RGLSP and the mature DGL is Gly-Leu. The resulting plasmid was called pBIOC40. Starting from pBIOC40, the BglII-XbaI fragment carrying the sequence of RGLSPS-DGL was isolated by double enzymatic digestion by BglII and XbaI, purification by electrophoresis over 0.8% agarose gel, electroelution (Sambrook et al., 1989), precipitation with alcohol and drying. This DNA fragment was then treated with Klenow enzyme in accordance with the manufacturer's instructions and ligated to the plasmid DNA of pBIOC21, which had been digested at the HindIII site, treated with Klenow and dephosphorylated by the alkaline phosphatase enzyme of the intestine of the calf (Boehringer Mannheim) in accordance with the manufacturer's instructions. The ligation was carried out with 20 ng of the dephosphorylated vector described above and 200 ng of DNA fragments, containing the RGLSP-DGL, described above in a reaction medium of 20 μl in the presence of 2 μl of the buffer T4 DNA ligase×10 (Amersham), 2 μl of 50% polyethylene glycol 8000 and 5 U of the enzyme T4 DNA ligase (Amersham) at 14° C. for 16 hours. The bacteria *Escherichia coli* DH5α, rendered competent beforehand, were transformed (Hanahan, 1983). The plasmid DNA of the clones obtained, selected on a medium containing 12 μg/ml of tetracycline, was extracted by the alkaline lysis method (Birnboim and Doly, 1979) and analysed by enzymatic digestion by restriction enzymes. The resulting clone was called pBIOC41. The nucleotide sequence of the fragments which code for the recombinant protein RGLSP-DGL was verified by sequencing with the aid of the T7™ sequencing kit, marketed by Pharmacia, by the dideoxynucleotide method (Sanger et al., 1977). The plasmid DNA of the binary vector pBIOC41 was introduced by direct transformation into the strain LBA4404 of *Agrobacterium tumefaciens* in accordance with the process of Holsters et al. (1978). The validity of the clone retained was verified by enzymatic digestion of the plasmid DNA introduced.

I-B) Construction of Chimaeric Genes which Code for the Recombinant DGL and Allow Expression in the Tomato The constructions used are the same as those used for the genetic transformation of tobacco, namely the plasmids pBIOC25, pBIOC26 and pBIOC41.

II. Construction of Chimaeric Genes which Code for the Recombinant Protein of Dog Gastric Lipase and Allow Expression in Rape Seeds a) Construction of the Binary Plasmid pBIOC28 Containing the Promoter pCRU

Expression of dog gastric lipase (DGL) in rape seeds required the insertion of the cDNA which codes for the DGL between the following regulator sequences:

1. The promoter pCRU which corresponds to the non-coding region 5' of the gene of the reserve protein of the seeds, CRUCIFERIN A of radish (Depigny-This et al., 1992), and allows specific expression in the seeds;
2. The terminal transcription sequence, terminator polyA 35S, which corresponds to the non-coding region 3' of the sequence of the cauliflower mosaic virus, of double-stranded circular DNA, which produces the transcript 35S (Franck et al., 1980).

To obtain a binary plasmid similar to pBIOC21, but in which the promoter pd35S was replaced by the promoter pCRU, the fragment "EcoRI treated with Klenow-BamHI", containing the promoter pCRU, was isolated using the plasmid pBI221-CRURSP derived from pBI221 (marketed by Depigny-This et al., 1992. The plasmid pBI221-CRURSP is derived from pBI221 (marketed by Clontech) by replacement of the promoter 35S by the promoter pCRU.

The fragment "EcoRI treated with Klenow-BamHI" carrying the promoter pCRU was purified by electrophoresis over 0.8% agarose gel, electroeluted (Sambrook et al., 1989), subjected to precipitation with alcohol, dried and ligated to the plasmid DNA of pJIT163 (described in paragraph I.), digested by KpnI, which had been treated with T4 DNA Polymerase (New England Biolabs) in accordance with the manufacturer's instructions and then digested with BamHI, purified by electrophoresis over 0.8% agarose gel, electroeluted (Sambrook et al., 1989), subjected to precipitation with alcohol, dried and dephosphorylated by the alkaline phosphatase enzyme of the intestine of the calf (Boehringer Mannheim) in accordance with the manufacturer's instructions. The ligation was carried out with 20 ng of the dephosphorylated vector described above and 200 ng of DNA fragments of "EcoRI treated with Klenow-BamHI" described above in a reaction medium of 20 µl in the presence of 2 µl of the buffer T4 DNA ligase×10 (Amersham), 2 µl of 50% polyethylene glycol 8000 and 5 U of the enzyme T4 DNA ligase (Amersham) at 14° C. for 16 hours. The bacteria Escherichia coli Dh5α, rendered competent beforehand, were transformed (Hanahan, 1983). The plasmid DNA of the clones obtained, selected on a medium containing 50 µg/ml of ampicillin, was extracted by the alkaline lysis method (Birnboim and Doly, 1979) and analysed by enzymatic digestion by restriction enzymes. The resulting plasmid was called pBIOC27.

The expression cassette made up of the promoter pCRU and the terminator polyA 35S was isolated using pBIOC27 by total digestion with XhoI followed by partial digestion with EcoRI. It was purified by electrophoresis over 0.8% agarose gel, electroeluted (Sambrook et al., 1989), subjected to precipitation with alcohol, dried, treated with Klenow (New England Biolabs) in accordance with the manufacturer's instructions and ligated to the plasmid DNA of pBIOC24 at the EcoRI site treated with Klenow and dephosphorylated by the alkaline phosphatase enzyme of the intestine of the calf (Boehringer Mannheim) in accordance with the manufacturer's instructions. The ligation was carried out with 20 ng of the dephosphorylated vector described above and 200 ng of the DNA fragments XhoI-EcoRI described above in a reaction medium of 20 µl in the presence of 2 µl of the buffer T4 DNA ligase×10 (Amersham), 2 µl of 50% polyethylene glycol 8000 and 5 U of the enzyme T4 DNA ligase (Amersham) at 14° C. for 16 hours. The bacteria Escherichia coli Dh5α, rendered competent beforehand, were transformed (Hanahan, 1983). The plasmid DNA of the clones obtained, selected on a medium containing 12 µg/ml of tetracycline, was extracted by the alkaline lysis method (Birnboim and Doly, 1979) and analysed by enzymatic digestion by restriction enzymes. The resulting plasmid was called pBIOC28.

b. Construction of the Binary Plasmid pBIOC29 Containing PPS-DGL

Isolation of the BglII-XbaI fragment carrying the sequence PPS-DGL using pBIOC24 has already been described in I-A-b. This fragment was ligated to the plasmid DNA of pBIOC28 at the EcoRI site treated with Klenow and dephosphorylated by the alkaline phosphatase enzyme of the intestine of the calf (Boehringer Mannheim) in accordance with the manufacturer's instructions. The ligation was carried out with 20 ng of the dephosphorylated vector described above and 200 ng of the DNA fragments BglII-XbaI containing PPS-DGL in a reaction medium of 20 µl in the presence of the buffer T4 DNA ligase×10 (Amersham), 2 µl of 50% polyethylene glycol 8000 and 5 U of the enzyme T4 DNA ligase (Amersham) at 14° C. for 16 hours. The bacteria Escherichia coli DH5α, rendered competent beforehand, were transformed (Hanahan, 1983). The plasmid DNA of the clones obtained, selected on a medium containing 12 µl/ml of tetracycline, was extracted by the alkaline lysis method (Birnboim and Doly, 1979) and analysed by enzymatic digestion by restriction enzymes. The resulting plasmid was called pBIOC29. The nucleotide sequence of the recombinant protein PPS-DGL was verified by sequencing with the aid of the T7™ sequencing kit, marketed by Pharmacia, by the dideoxynucleotide method (Sanger et al., 1977). The plasmid DNA of the binary vector pBIOC29 was introduced by direct transformation into the strain LBA4404 of Agrobacterium tumefaciens in accordance with the process of Holsters et al. (1978). The validity of the clone retained was verified by enzymatic digestion of the plasmid DNA introduced.

c) Construction of Binary Plasmids pBIOC90 and pBIOC91 Containing the pGEA1D Promoter Expression of the animal gene which codes for dog gastric lipase (DGL) in rape seeds required the following regulator sequences:

1. the promoter pGEA1 corresponding to the non-coding region 5' of the gene of the reserve protein of the seeds, GEA1 of Arabidopsis thaliana (Gaubier et al., 1993), and allows specific expression in the seeds;
2. the terminal transcription sequence, terminator polyA 35S, which corresponds to the non-coding region 3' of the sequence of the cauliflower mosaic virus, of double-stranded circular DNA, which produces the transcript 35S (Franck et al., 1980).

To obtain the binary plasmid pBIOC90 similar to pBIOC21 but in which the promoter pd35S was replaced by the promoter pGEA1D, the fragment HindIII-BamHI treated with Klenow, containing the promoter pGEA1, was isolated using plasmid pGUS2-pGEA1. The clone pGUS-2-pGEA1 deriving from pBI221 by replacement of the promoter p35S by the promoter pGEA1, contains 2 ATG in frame: ATG of the gene GEA1 (Em2) and ATG of the gene gus. The ATG of the gene GEA1 was destroyed. The DNA fragment contained between the SalI site and the sequences upstream from the ATG of the gene GEA1 of the clone pGUS-2-pGEA1 was then amplified by PCR using 2 oligonucleotides: 5' CAAACGTGTACAATAGCCC 3' (SEQ ID NO: 23) and 5' CCCGGGGATCCTTTTTTG 3' (SEQ ID NO: 24). The hybridization temperature was adjusted. The fragment amplified by PCR was digested by SalI and BamHI, purified by electrophoresis over 2% agarose gel, electroeluted (Sambrook et al. 1989), precipitated in the presence of 1/10 volume of 3M sodium acetate pH 4.8 and 2.5 volumes of absolute ethanol at −80° C. for minutes, centrifuged at 12000 g for 30 minutes, washed with 70% ethanol, then ligated to plasmid DNA of pGUS-2-GEA1 double digested by SalI and BamHI, purified by electrophoresis over 0.8% agarose gel, electroeluted (Sambrook et al., 1989), subjected to precipitation with alcohol, dried. Ligation was carried out with 100 ng of vector and 50 ng of digested DNA fragments originating from the PCR amplification described above, in a reaction medium of 10 µl in the presence of 1 µl of the buffer T4 DNA ligase×10 (Amersham) and 2.5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 50 µg/ml ampicillin, was extracted by the alkaline lysis method (Birnboim and Doly, 1979) and analysed by enzymatic digestion by restriction enzymes. Certain retained clones were verified by sequencing with the aid of the T7™ sequencing kit, marketed by Pharmacia, by the dideoxynucleotide method (Sanger et al., 1977). The resulting clone was called pGUS-2-pGEA1D.

The HindIII-BamHI fragment carrying the promoter pGEA1D isolated from pGUS-2-pGEA1D, treated with Klenow in accordance with the manufacturer's instructions (Biolabs), was purified by electrophoresis over 0.8% agarose gel, electroeluted (Sambrook et al., 1989), subjected to precipitation with alcohol, dried and ligated to the plasmid DNA of pBIOC21 at KpnI and HINDIII sites treated with the enzyme T4 DNA polymerase (Biolabs) in accordance with the manufacturer's instructions. The ligation was carried out with 20 ng of dephosphorylated pBIOC21 and 200 ng of the XhoI-EcoRI DNA fragments described above in a reaction medium of 20 µl in the presence of 2 µl of the buffer T4 DNA ligase×10 (Amersham), 2 µl of 50% polyethylene glycol 8000 and 5 U of the enzyme T4 DNA ligase (Amersham) at 14° C. for 16 hours. The bacteria *Escherichia coli* DH5α, rendered competent beforehand, were transformed (Hanahan, 1983). The plasmid DNA of the clones obtained, selected on 12 µg/ml tetracycline was extracted by the alkaline lysis method (Birnboim and Doly, 1979) and analysed by enzymatic digestion by restriction enzymes. The resulting plasmid was called pBIOC90.

To obtain the binary plasmid pBIOC91, the expression cassette "pGEA1D-tNOS", isolated from pBSII-pGEA1D. was introduced into the binary plasmid pSCV1.2 itself obtained by cloning of the HindIII fragment carrying the expression cassette "p35S-nptII-tNOS" described by Fromm et al. (1986) at the HindIII site of pSCV1 constructed by Edwards G. A. in 1990 following the usual cloning procedures.

The plasmid pBSII-pGEA1D was obtained in two stages:
on the one hand, the SacI-EcoRI fragment carrying tNOS (terminator of the gene of nopaline synthase) of *Agrobacterium tumefaciens,* treated with the enzyme T4 DNA polymerase (Biolabs) in accordance with the manufacturer's instructions and purified, was cloned at the EcoRV site of pBSIISK+ marketed by Stratagene, dephosphorylated by the alkaline phosphatase enzyme of the intestine of the calf (Boehringer Mannheim) in accordance with the manufacturer's instructions. The ligation was carried out with 20 ng of the dephosphorylated vector and 200 ng of the DNA fragments containing tNOS described above in a reaction medium of 20 µl in the presence of 2 µl of the buffer T4 DNA ligase×10 (Amersham), 2 µl of 50% polyethylene glycol 8000 and 5 U of the enzyme T4 DNA ligase (Amersham) at 14° C. for 16 hours. The bacteria *Escherichia coli* DH5α, rendered competent beforehand, were transformed (Hanahan, 1983). The plasmid DNA of the clones obtained, selected on 50 µg/ml ampicillin, was extracted by the alkaline lysis method (Birnboim and Doly, 1979) and analysed by enzymatic digestion by restriction enzymes. Certain retained clones were verified by sequencing with the aid of the T7™ sequencing kit, marketed by Pharmacia, by the dideoxynucleotide method (Sanger et al., 1977). The resulting plasmid was called pBSII-tNOS.

on the other hand, the fragment carrying pGEA1D double digested by HindIII treated with the enzyme Klenow and BamHI, purified, was cloned at the "XbaI treated with Klenow and BamHI" sites of the plasmid pBSII-tNOS. The ligation was carried out with 100 ng of the vector described above and 50 ng of the DNA fragments described above in a reaction medium of 10 µl in the presence of 1 µl of the buffer T4 DNA ligase×10 (Amersham) and 2.5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 50 µg/ml ampicillin, was extracted by the alkaline lysis method (Birnboim and Doly, 1979) and analysed by enzymatic digestion by restriction enzymes. The resulting plasmid was called pBSII-pGEA1D.

Then, the expression cassette "pGEA1D-tNOS" carried by the XbaI-HindIII fragment treated with Klenow, was cloned at the SmaI site of pSCV1.2 dephosphorylated by the alkaline phosphatase enzyme of the intestine of the calf (Boehringer Mannheim) in accordance with the manufacturer's instructions. The ligation was carried out with ng of dephosphorylated pSCV1.2 and 200 ng of the fragments carrying the expression cassette "pGEA1D-tNOS", in a reaction medium of 20 µl in the presence of 2 µl of the buffer T4 DNA ligase×10 (Amersham), 2 µl of 50% polyethylene glycol 8000 and 5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 50 µg/ml ampicillin, was extracted by the alkaline lysis method (Birnboim and Doly, 1979) and analysed by enzymatic digestion by restriction enzymes. The resulting plasmid was called pBIOC91.

d) Construction of Binary Plasmid pBIOC92 Containing the pGEA6D Promoter

Expression of the animal gene which codes for dog gastric lipase (DGL) in rape seeds required the following regulator sequences:
1. the promoter pGEA6 corresponding to the non-coding region 5' of the gene of the reserve protein of the seeds, GEA6 of *Arabidopsis thaliana* (Gaubier et al., 1993), and allows specific expression in the seeds;
2. the terminal transcription sequence, terminator polyA 35S, which corresponds to the non-coding region 3' of the sequence of the cauliflower mosaic virus, of double-stranded circular DNA, which produces the transcript 35S (Franck et al., 1980).

To obtain the binary plasmid pBIOC92 similar to pBIOC21 but in which the promoter pd35S was replaced by the promoter pGEA6D, the fragment EcoRI-BamHI treated with Klenow, containing the promoter pGEAG, was isolated using plasmid pGUS2-pGEA6. The clone pGUS-2-pGEA6 deriving from pUC18, contains 2 ATG in phase: ATG of the gene GEA6 (Em6) and ATG of the gene gus. The ATG of the gene GEA6 was destroyed. The DNA fragment contained between the AccI site and the sequences upstream from the ATG of the gene GEA6 of the clone pGUS-2-pGEA6 was then amplified by PCR using 2 oligonucleotides: 5' AAG-TACGGCCACTACCACG 3' (SEQ ID NO: 25) and 5' CCCGGGGATCCTGGCTC 3' (SEQ ID NO: 26). The hybridization temperature was adjusted.

The fragment amplified by PCR was digested by AccI and BamHI, purified by electrophoresis over 2% agarose gel, electroeluted (Sambrook et al. 1989), precipitated in the presence of 1/10 volume of 3M sodium acetate pH 4.8 and 2.5 volumes of absolute ethanol at −80° C. for 30 minutes, centrifuged at 12000 g for 30 minutes, washed with 70% ethanol, dried, then ligated to plasmid DNA of pGUS-2-GEA6 double digested by AccI and BamHI, purified by electrophoresis over 0.8% agarose gel, electroeluted (Sambrook et al., 1989), subjected to precipitation with alcohol, dried. Ligation was carried out with 100 ng of the vector described above and 50 ng of digested DNA fragments originating from the PCR amplification described above, in a reaction medium of 10 μl in the presence of 1 μl of the buffer T4 DNA ligase×10 (Amersham) and 2.5 U of the enzyme T4 DNA ligase (Amersham) at 14° C. for 16 hours. The bacteria Escherichia coli Dh5α, rendered competent beforehand, were transformed (Hanahan, 1983). The plasmid DNA of the clones obtained, selected on 50 μg/ml ampicillin, was extracted by the alkaline lysis method (Birnboim and Doly, 1979) and analysed by enzymatic digestion by restriction enzymes. Certain retained clones were verified by sequencing with the aid of the T7™ sequencing kit, marketed by Pharmacia, by the dideoxy-nucleotide method (Sanger et al., 1977). The resulting clone was called pGUS-2-pGEA6D.

The EcoRI-BamHI fragment carrying the promoter pGEA6D isolated from pGUS-1-pGEA6D, treated with Klenow in accordance with the manufacturer's instructions (Biolabs), was purified by electrophoresis over 0.8% agarose gel, electroluted (Sambrook et al., 1989), subjected to precipitation with alcohol, dried and ligated to the plasmid DNA of modified pBIOC21 at the XhoI site treated with Klenow. The modified plasmid pBIOC21 was obtained by double digestion of pBIOC21 by HindIII treated with Klenow and KpnI to delete the fragment carrying the promoter pd35S and to replace it with the KpnI-EcoRV fragment carrying the compound polylinker of sites KpnI-XhoI-SalI-ClaL-HindIII-BamHI-SmaI-EcoRI-EcoRV of pBSIISK+.

The ligation was carried out with 20 ng of dephosphory-lated modified pBIOC21 and 200 ng of the EcoRI-BamHI DNA fragments described above in a reaction medium of 20 μl in the presence of 2 μl of the buffer T4 DNA ligase×10 (Amersham), 2 μl of 50% polyethylene glycol 8000 and 5 U of the enzyme T4 DNA ligase (Amersham) at 14° C. for 16 hours. The bacteria Escherichia coli DH5α, rendered competent beforehand, were transformed (Hanahan, 1983). The plasmid DNA of the clones obtained, selected on 12 μg/ml tetracyclin, was extracted by the alkaline lysis method (Birnboim and Doly, 1979) and analysed by enzymatic digestion by restriction enzymes. The resulting plasmid was called pBIOC92.

e) Construction of Binary Plasmids pBIOC93, pBIOC94, pBIOC95, pBIOC96 and pBIOC97 Containing RGLSP-DGL The plasmid pBIOC40 is described above. This plasmid contains the fragment BglII-XbaI carrying the sequence RGLSP-DGL.

This fragment was isolated by double enzymatic digestion by BglII and XbaI, purified by electrophoresis over 0.8% agarose gel, electroluted, subjected to precipitation with alcohol, dried, treated with Klenow and ligated to pBIOC28 (described above) digested by EcoRI treated with Klenow and dephosphorylated; to pBIOC90 digested by EcoRI treated with Klenow and dephosphorylated; to pBIOC91 digested by SmaI and dephosphorylated; to pBIOC92 digested by HindIII treated with Klenow and dephosphorylated to produce pBIOC93, pBIOC94, pBIOC95 and pBIOC96 respectively.

The plasmid pBIOC97 results from the cloning of the fragment KpnI-EcoRV carrying the expression cassette "pGEA6D-RGLSP-DGL-t35S", treated by the enzyme T4 DNA polymerase, purified by electrophoresis over 0.8% agarose gel, electroluted, subjected to precipitation with alcohol, dried and ligated to pSCV1.2 digested by SmaI and dephosphorylated. The expression cassette "pGEA6D-RGLSP-DGL-t35S" originates from pBIOC92.

III. Construction of Chimaeric Genes which Code for the Recombinant Protein of Human Gastric Lipase and Allow Constitutive Expression, for Example, in Tobacco Leaves and Seeds a) Construction of the Binary Plasmid pBIOC82 Containing the Chimaeric Promoter SUPER-PROMOTER pSP Expression of the gene which codes for human gastric lipase (HGL) in tobacco leaves required the following regulator sequences:

1. the chimaeric promoter super-promoter (pSP; PCT/US94/12946). It is constituted by the fusion of three transcriptional activator elements of the promoter of the gene of octopine synthase of Agrobacterium tumefaciens, of a transcriptional activator element of the promoter of the gene of mannopine synthase and of the mannopine synthase promoter of Agrobacterium tumefaciens;

2. the terminal transcription sequence, terminator polyA 35S, which corresponds to the non-coding region 3' of the sequence of the cauliflower mosaic virus of double-stranded circular DNA, which produces the transcript 35S (Franck et al., 1980).

To obtain a binary plasmid similar to pBIOC21, but in which the promoter pd35S was replaced by the promoter pSP, the pvuII-SalI fragment, subjected to Klenow, containing the promoter pSP, was isolated using the plasmid pBISNI (PCT/US94/12946), purified by electrophoresis over 1% agarose gel, electroluted (Sambrook et al., 1989), subjected to precipitation with alcohol, dried and ligated to the plasmid DNA of pBIOC81, doubly digested by KpnI and EcoRI, subjected to DNA T4 polymerase and dephosphorylated by the alkaline phosphatase enzyme of the intestine of the calf (Boehringer Mannheim) in accordance with the manufacturer's instructions. The plasmid pBIOC81 corresponds to pBIOC21 the XbaI site of which has been deleted. In order to do this, the plasmid pBIOC21 was digested by XbaI, then subjected to the action of the Klenow enzyme and ligated by the action of T4 DNA ligase.

The ligation was carried out with 20 ng of the dephosphorylated vector described above and 200 ng of DNA fragments carrying pSP described above in a reaction medium of 20 μl in the presence of 2 μl of the buffer T4 DNA ligase×10 (Amersham), 2 μl 50% polyethylene glycol 8000 and 5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 12 μg/ml of tetracyclin, was extracted by the alkaline lysis method (Birnboim and Doly, 1979) and analysed by enzymatic digestion by restriction enzymes. The resulting plasmid was called pBIOC82.

Human gastric lipase (HGL) is synthesized naturally in the form of a precursor described in the publication by Bodmer et al., 1987. The mature HGL protein is constituted by 379 amino acids. Its signal peptide (HGLSP) is composed of 19 amino acids. The restriction site between HGLSP and HGL is Gly-Leu.

The sequence which codes for the precursor of HGL was used for the construction of the binary plasmids pBIOC85 containing HGLSP-HGL, pBIOC87 containing HPLSP-HGL and pBIOC89 containing RGLSP-HGL where the sequence which codes for HGL is preceded by those which code for its natural signal peptide HGLSP, the signal peptide of human pancreatic lipase (HPLSP; Giller et al., 1992) and the signal peptide of rabbit gastric lipase (RGLSP; already described previously; European Patent No. 92.403055.4) respectively.

The sequence which codes for the precursor of HGL was isolated by double digestion with PstI and DraI, purified by electrophoresis over 0.8% agarose gel, electroeluted (Sambrook et al., 1989), precipitated in the presence of 1/10 volume of 3M sodium acetate pH 4.8 and 2.5 volumes of absolute ethanol at minus 80° C. for minutes, centrifuged at 12000 g for 30 minutes, washed with 70% ethanol and dried. Then, it was cloned at the PstI and SpeI sites (subjected to the action of the enzyme T4 DNA polymerase (Biolabs) in accordance with the manufacturer's instructions) of the plasmid pBSIISK+ marketed by Stratagene. The ligation was carried out with 100 ng of the vector and 50 ng of the DNA fragments carrying the sequence which codes for the precursor of HGL described above, in a reaction medium of 10 μl in the presence of 1 μl of the buffer T4 DNA ligase×10 (Amersham) and 2.5 U of the enzyme T4 DNA ligase (Amersham) at 14° C. for 16 hours. The bacteria *Escherichia coli* DH5α, rendered competent beforehand, were transformed (Hanahan, 1983). The plasmid DNA of the clones obtained, selected on 50 μg/ml of ampicillin, was extracted by the alkaline lysis method (Birnboim and Doly, 1979) and analysed by enzymatic digestion by restriction enzymes. The resulting plasmid was called pBIOC83.

The sequence which codes for mature HGL was modified by the introduction of a BamHI site, which did not exist beforehand, in the ninth and tenth codons, by directed mutagenesis by PCR using 2 oligodeoxynucleotides, 5' aaactgcaggctcgag TTG TTT GGA AAA TTA CAT CCT GGA tcc CCT GAA GTG ACT ATG 3' (SEQ ID NO: 27; containing the unique PstI, XhoI and BamHI sites) and 5' AAT GGT GGT GCC CTG GGA ATG GCC AAC ATA GTG TAG CTG C 3' (SEQ ID NO 28; containing the unique MscI site in the plasmid pBIOC83).

The PCR amplification of the fragment PstI-MscI was carried out in 100 μl of reaction medium containing 10 μl of the buffer Taq DNA polymerase×10 (500 mM KCl, 100 mM Tris-HCl, pH 9.0 and 1% Triton×100), 6 μl of mM MgCl$_2$, 3 μl of 10 mM dNTP (dATP, dCTP, dGTP and dTTP), 100 pM of each of the 2 oligodeoxy-nucleotides described above, 5 ng of matrix DNA (vector pBIOC83), 2.5 U of Taq DNA polymerase (Promega) and 2 drops of vaseline oil. The DNA was denatured at 94° C. for 5 minutes, subjected to 30 cycles each constituted by 1 minute of denaturation at 94° C., 1 minute of hybridization at 65° C. and 1 minute of elongation at 72° C., then elongation at 72° C. was continued for 5 minutes. This PCR reaction was carried out in the "DNA Thermal Cycler" machine of PERKIN ELMER CETUS. The oil was removed by extraction with chloroform. The DNA fragments contained in the reaction medium were then precipitated in the presence of 1/10 volume of 3M sodium acetate, pH 4.8, and 2.5 volumes of absolute ethanol at minus 80° C. for 30 min, centrifuged at 12,000 g for 30 min, washed with 70% ethanol, dried and digested by the 2 restriction enzymes PstI and MscI. The digested DNA fragments originating from the PCR amplification were purified by electrophoresis over 2% agarose gel, electroeluted (Sambrook et al., 1989), precipitated in the presence of 1/10 volume of 3M sodium acetate, pH 4.8, and 2.5 volumes of absolute ethanol at −80° C. for 30 min, centrifuged at 12,000 g for min., washed with 70% ethanol, dried and then ligated to the plasmid DNA of pBIOC83, which had been digested twice by PstI and MscI, purified by electrophoresis over 0.8% agarose gel, electroeluted, subjected to precipitation with alcohol, dried. The ligation was carried out with 100 ng of the vector and 50 ng of the digested DNA fragments, originating from the amplification by PCR, described above, in a reaction medium of 10 μl in the presence of 1 μl of the buffer T4 DNA ligase×10 (Amersham) and 2.5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 50 μg/ml of ampicillin, was extracted by the alkaline lysis method (Birnboim and Doly, 1979) and analysed by enzymatic digestion by restriction enzymes. Some of the retained clones were verified by sequencing with the aid of the T7™ sequencing kit, marketed by Pharmacia, by the dideoxynucleotide method (Sanger et al., 1977). Introduction of the BamHI restriction site does not modify the genetic code of the HGL. In fact, the natural HGL sequence GGA AGC (Gly-Ser) becomes GGA TCC (Gly-Ser). The resulting plasmid was called pBIOC84.

b) Construction of the Binary Plasmid pBIOC85 Containing HGLSP-HGL

The fragment PstI-XbaI carrying the sequence of HGLSP-HGL was isolated by double enzymatic digestion by PstI and XbaI from pBIOC83, purified by electrophoresis over 0.8% agarose gel, electroeluted (Sambrook et al., 1989), subjected to precipitation with alcohol and dried. Then, this DNA fragment was treated with the enzyme T4 DNA polymerase (Biolabs) in accordance with the manufacturer's instructions and ligated to the plasmid DNA of pBIOC82 digested at the EcoRI site, treated with Klenow (Biolabs) and dephosphorylated by the alkaline phosphatase enzyme of the intestine of the calf (Boehringer Mannheim) in accordance with the manufacturer's instructions. The ligation was carried out with 20 ng of the dephosphorylated vector described above and 200 ng of DNA fragments containing the HGLSP-HGL described above, in a reaction medium of 20 μl in the presence of 2 μl of the buffer T4 DNA ligase×10 (Amersham), 2 μl of 50% polyethylene glycol 8000 and 5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 12 μg/ml of tetracycline, was extracted by the alkaline lysis method (Birnboim and Doly, 1979) and analysed by enzymatic digestion by restriction enzymes. The resulting clone was called pBIOC85. The nucleic sequence of the fragment which codes for the recombinant protein HGLSP-HGL was verified by sequencing with the aid of the T7™ sequencing kit, marketed by Pharmacia, by the dideoxynucleotide method (Sanger et al., 1977). The restriction sequence between the HGLSP and mature HGL sequences is Gly-Leu. The plasmid DNA of the binary vector pBIOC85 was introduced by direct transformation into the strain LBA4404 of *Agrobacterium tumefaciens* in accordance with the method of Holsters et al. (1978). The validity of the retained clone was verified by enzymatic digestion of the plasmid DNA introduced.

c) Construction of the Binary Plasmid pBIOC86 Containing HPLSP-HGL

The plasmid pBIOC84 was digested twice by PstI and BamHI in order to suppress the sequence which codes for the signal peptide HSLSP and the first 8 amino acids of the mature HGL protein (Leu-Phe-Gly-Lys-Leu-His-Pro-Gly). This sequence was replace by that which codes for the signal peptide HPLSP of 16 amino acids (ATG CTG CCA CTT TGG ACT CTT TCA CTG CTG CTG GGA GCA GTA GCA GGA) (SEQ ID NO: 29) fused to that which codes for the first 8 codons of the mature HGL protein ("HPLSP-first 8 codons of mature HGL"). The sequence "HPLSP-first 8 codons of mature HGL" was amplified by PCR from the matrix 5' aaactgcaggctcgagaacaATG CTG CCA CTT TGG ACT CTT TCA CTG CTG CTG GGA GCA GTA GCA GGA TTG TTT GGA AAA TTA CAT CCT GGA tcc CCT G 3' (SEQ ID NO: 30) using the 2 oligodeoxynucleotides, 5' aaactgcaggctcgagaacaATG C 3' (SEQ ID NO: 31) and 5' C AGG gga TCC AGG ATG TAA TTT TCC 3' (SEQ ID NO: 32), following the PCR amplification protocol described previously (see paragraph I above). The hybridization temperature was adjusted. After double enzymatic digestion by PstI and BamHI, the DNA fragments originating from the PCR amplification were purified by electrophoresis over 2% agarose gel, electroeluted (Sambrook et al. 1989), precipitated in the presence of 1/10 volume of 3M sodium acetate pH 4.8 and 2.5 volumes of absolute ethanol at −80° C. for 30 minutes, centrifuged at 12000 g for 30 minutes, washed with 70% ethanol, dried, then ligated with plasmid DNA of pBIOC84 double digested by PstI and BamHI, purified by electrophoresis over 0.8% agarose gel, electroeluted (Sambrook et al., 1989), subjected to precipitation with alcohol, dried. Ligation was carried out with 100 ng of vector and 50 ng of digested DNA fragments originating from the PCR amplification described above, in a reaction medium of 10 μl in the presence of 1 μl of the buffer T4 DNA ligase×10 (Amersham) and 2.5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 50 μg/ml ampicillin, was extracted by the alkaline lysis method (Birnboim and Doly, 1979) and analysed by enzymatic digestion by restriction enzymes. Certain retained clones were verified by sequencing with the aid of the T7™ sequencing kit, marketed by Pharmacia, by the dideoxynucleotide method (Sanger et al., 1977). The sequences of HPLSP and mature HGL were cloned while maintaining their open reading frames (that is to say, such that they constitute a unique open reading frame). The restriction sequence between the sequences HPLSP and mature HGL is Gly-Leu. The resulting plasmid was called pBIOC86.

The fragment PstI-XbaI carrying the sequence HPLSP-HGL was isolated from BIOC86 by double enzymatic digestion by PstI and XbaI, purified by electrophoresis over 0.8% agarose gel, electroeluted (Sambrook et al., 1989), subjected to precipitation with alcohol and dried. Then, this DNA fragment was treated with the enzyme T4 DNA polymerase (Biolabs) in accordance with the manufacturer's instructions and ligated to the plasmid DNA of pBIOC82 digested at the EcoRI site, treated with Klenow (Biolabs) and dephosphorylated by the alkaline phosphatase enzyme of the intestine of the calf (Boehringer Mannheim) in accordance with the manufacturer's instructions. The ligation was carried out with 20 ng of the dephosphorylated vector described above and 200 ng of DNA fragments containing the HPLSP-HGL described above in a reaction medium of 20 μl in the presence of 2 μl of the buffer T4 DNA ligase×10 (Amersham), 2 μl of 50% polyethylene glycol 8000 and 5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on a medium containing 12 μg/ml of tetracyline, was extracted by the alkaline lysis method (Birnboim and Doly, 1979) and analysed by enzymatic digestion by restriction enzymes. The resulting clone was called pBIOC87. The nucleic sequence of the fragment which codes for the recombinant protein HPLSP-HGL was verified by sequencing with the aid of the T7™ sequencing kit, marketed by Pharmacia, by the dideoxynucleotide method (Sanger et al., 1977). The plasmid DNA of the binary vector pBIOC87 was introduced by direct transformation in the strain LBA4404 of *Agrobacterium tumefaciens* in accordance with the method of Holsters et al. (1978). The validity of the retained clone was verified by enzymatic digestion of the plasmid DNA introduced.

d) Construction of the Binary Plasmid pBIOC89 Containing RGLSP-HGL

The plasmid pBIOC84 was double digested by PstI and BamHI in order to suppress the sequence which codes for the signal peptide HGLSP and the first 8 amino acids of the mature HGL protein (Leu-Phe-Gly-Lys-Leu-His-Pro-Gly). This sequence was replace by that which codes for the signal peptide RGLSP of 19 amino acids (ATG TGG GTG CTT TTC ATG GTG GCA GCT TTG CTA TCT GCA CTT GGA ACT ACA CAT GGT) (SEQ ID NO: 33) fused to that which codes for the first 8 codons of the mature HGL protein ("RGLSP-first 8 codons of mature HGL"). The sequence "RGLSP-first 8 codons of mature HGL" was amplified by PCR from the matrix 5' aaactgcaggctcgagaacaATG CTG CCA CTT TGG ACT CTT TCA CTG CTG CTG GGA GCA GTA GCA GGA TTG TTT GGA AAA TTA CAT CCT GGA tcc CCT G 3' (SEQ ID NO: 34) using the 2 oligodeoxynucleotides, 5' aaactgcaggctcgagaacaATG TGG 3' (SEQ ID NO: 35) and 5' C AGG gga TCC AGG ATG TAA TTT TCC 3' (SEQ ID NO: 32), following the PCR amplification protocol described previously (see paragraph I above). The hybridization temperature was adjusted. After double enzymatic digestion by PstI and BamHI, the DNA fragments originating from the PCR amplification were purified by electrophoresis over 2% agarose gel, electroeluted (Sambrook et al. 1989), precipitated in the presence of 1/10 volume of 3M sodium acetate pH 4.8 and 2.5 volumes of absolute ethanol at −80° C. for minutes, centrifuged at 12000 g for 30 minutes, washed with 70% ethanol, dried, then ligated with plasmid DNA of pBIOC84 double digested by PstI and BamHI, purified by electrophoresis over 0.8% agarose gel, electoeluted (Sambrook et al., 1989), subjected to precipitation with alcohol, dried. Ligation was carried out with 100 ng of vector and 50 ng of digested DNA fragments originating from the PCR amplification described above, in a reaction medium of 10 µl in the presence of 1 µl of the buffer T4 DNA ligase×10 (Amersham) and 2.5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 50 µg/ml ampicillin, was extracted by the alkaline lysis method (Birnboim and Doly, 1979) and analysed by enzymatic digestion by restriction enzymes. Certain retained clones were verified by sequencing with the aid of the T7™ sequencing kit, marketed by Pharmacia, by the dideoxynucleotide method (Sanger et al., 1977). The sequences of RGLSP and mature HGL were cloned while maintaining their open reading frames (that is to say, such that they constitute a unique open reading frame). The restriction sequence between the sequences RGLSP and mature HGL is Gly-Leu. The resulting plasmid was called pBIOC88.

The fragment PstI-XbaI carrying the sequence RGLSP-HGL was isolated from pBIOC88 by double enzymatic digestion by PstI and XbaI, purified by electrophoresis over 0.8% agarose gel, electroeluted (Sambrook et al., 1989), subjected to precipitation with alcohol and dried. Then, this DNA fragment was treated with the enzyme T4 DNA polymerase (Biolabs) in accordance with the manufacturer's instructions and ligated to the plasmid DNA of pBIOC82 digested at the XbaI site, treated with Klenow (Biolabs) and dephosphorylated by the alkaline phosphatase enzyme of the intestine of the calf (Boehringer Mannheim) in accordance with the manufacturer's instructions. The ligation was carried out with 20 ng of the dephosphorylated vector and 200 ng of DNA fragments containing the RGLSP-HGL described above in a reaction medium of 20 µl in the presence of 2 µl of the buffer T4 DNA ligase×10 (Amersham), 2 µl of 50% polyethylene glycol 8000 and 5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on 12 µg/ml of tetracyline, was extracted by the alkaline lysis method (Birnboim and Doly, 1979) and analysed by enzymatic digestion by restriction enzymes. The resulting clone was called pBIOC89. The nucleic sequence of the fragment which codes for the recombinant protein RGLSP-HGL was verified by sequencing with the aid of the T7™ sequencing kit, marketed by Pharmacia, by the dideoxynucleotide method (Sanger et al., 1977). The plasmid DNA of the binary vector pBIOC89 was introduced by direct transformation in the strain LBA4404 of *Agrobacterium tumefaciens* in accordance with the method of Holsters et al. (1978). The validity of the retained clone was verified by enzymatic digestion of the plasmid DNA introduced.

IV. Construction of Chimaeric Genes which Code for the Recombinant Protein of Dog Gastric Lipase and Allow Expression in Corn Seeds a) Construction of Plasmids pBIOC98 and pBIOC99 Containing RGLSP-DGL and Allow Constitutive Expression in Corn Seeds The constitutive expression of the animal gene which codes for dog gastric lipase (DGL) in corn seeds required the following regulator sequences:

1. one of two promoters which allow constitutive expression:
   actine promoter of rice followed by the actine intron of rice (pAR-IAR) contained in the plasmid pAct1-F4 described by McElroy et al. (1991);

double constitutive promoter 35S (pd35S) of CaMV (cauliflower mosaic virus). It corresponds to a duplication of sequences activating the transcription situated upstream from the TATA element of the natural 35S promoter (Kay et al., 1987);

2. one of two terminators:
   the terminal transcription sequence, terminator polyA 35S, which corresponds to the non-coding region 3' of the sequence of the cauliflower mosaic virus, of double-stranded circular DNA, which produces the transcript 35S (Franck et al., 1980);

the terminal transcription sequence, terminator polyA NOS, which corresponds to the non-coding region 3' of the gene of nopaline synthase of plasmid Ti of *Agrobacterium tumefaciens* nopaline strain (Depicker et al., 1982).

The plasmid pBIOC98 where the sequence which codes for RGLSP-DGL is placed under the control of pAR-IAR was obtained by cloning the fragment BglII-XbaI carrying the sequence which codes for RGLSP-DGL at the sites "NcoI and SalI" of pBSII-pAR-IAR-tNOS.

The fragment BglII-XBaI carrying the sequence which codes for RGLSP-DGL was isolated from pBIOC40 (described above) by double enzymatic digestion by BglII and XbaI, purified by electrophoresis over 0.8% agarose gel, electroeluted, subjected to precipitation with alcohol, dried, then treated with Klenow enzyme. The plasmid pBSII-pAR-IAR-tNOS was double digested by SalI and NcoI, purified, treated with Mung Bean Nuclease enzyme (Biolabs) and dephosphorylated by the alkaline phosphatase enzyme of the intestine of the calf (Boehringer Mannheim) in accordance with the manufacturer's instructions. The ligation was carried out with 20 ng of the dephosphorylated vector and 200 ng of DNA fragments containing the sequence which codes for RGLSP-DGL described, above in a reaction medium of 20 µl in the presence of 2 µl of the buffer T4 DNA ligase×10 (Amersham), 2 µl of 50% polyethylene glycol 8000 and 5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on a medium containing 50 µg/ml of ampicillin, was extracted by the alkaline lysis method (Birnboim and Doly, 1979) and analysed by enzymatic digestion by restriction enzymes. The resulting plasmid was called pBIOC98.

The plasmid pBSII-pAR-IAR-tNOS results from the cloning at sites "EcoO1091 treated with Klenow and KpnI" of pBSII-tNOS of the fragment SnaBI-KpnI carrying the sequence corresponding to "pAR-IAR-start of the sequence which codes for the gene gus" isolated from the plasmid pAct1-F4. The ligation was carried out with 100 ng of the vector and 50 ng of DNA fragments described above in a reaction medium of 10 µl in the presence of 1 µl of the buffer T4 DNA ligase×10 (Amersham) and 2.5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on a medium containing 50 µg/ml of ampicillin, was extracted by the alkaline lysis method (Birnboim and Doly, 1979) and analysed by enzymatic digestion by restriction enzymes.

The plasmid pBSII-tNOS was obtained by cloning at the dephosphorylated site EcoRV of pBSIISK+ marketed by Stratagene, of the fragment SacI-EcoRI carrying the sequence tNOS isolated from pBI121 marketed by Clontech by double enzymatic digestion by SacI and EcoRV, subjected to purification by electrophoresis over 2% agarose gel and treated with the enzyme T4 DNA polymerase. The ligation was carried out with ng of the dephosphorylated vector and 200 ng of DNA fragments containing the sequence tNOS described above, in a reaction medium of 20 μl in the presence of 2 μl of the buffer T4 DNA ligase×10 (Amersham), 2 μl of 50% polyethylene glycol 8000 and 5 U of the enzyme T4 DNA ligase (Amersham) at 14° C. for 16 hours. The bacteria *Escherichia coli* DH5α, rendered competent beforehand, were transformed (Hanahan, 1983). The plasmid DNA of the clones obtained, selected on a medium containing 50 μg/ml of ampicillin, was extracted by the alkaline lysis method (Birnboim and Doly, 1979) and analysed by enzymatic digestion by restriction enzymes.

The plasmid pBIOC99 where the sequence which codes for RGLSP-DGL is placed under the control of pd35S was obtained by cloning at sites "KpnI and BamHI" of the plasmid pBSII-t35S, of the fragment KpnI-BamHI carrying the sequence corresponding to "pd35S-RGLSP-DGL" isolated from pBIOC41 described above. The ligation was carried out with 100 ng of the vector and 50 ng of DNA fragments described above in a reaction medium of 10 μl digested in the presence of 1 ml of the buffer T4 DNA ligase×10 (Amersham) and 2.5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on a medium containing 50 μg/ml of ampicillin, was extracted by the alkaline lysis method (Birnboim and Doly, 1979) and analysed by enzymatic digestion by restriction enzymes.

The plasmid pBSII-t35S was obtained by cloning at the dephosphorylated site SpeI treated with Klenow, of plasmid pBSIISK+ marketed by Stratagene, of the fragment SmaI-EcoRV carrying the sequence t35S isolated from pJIT163 (described above) by double enzymatic digestion by SmaI and EcoRV, subjected to purification by electrophoresis over 2% agarose gel. The ligation was carried out with ng of the dephosphorylated vector and 200 ng of DNA fragments containing the sequence t35S described above, in a reaction medium of 20 μl in the presence of 2 μl of the buffer T4 DNA ligase×10 (Amersham), 2 μl of 50% polyethylene glycol 8000 and 5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on a medium containing 50 μg/ml of ampicillin, was extracted by the alkaline lysis method (Birnboim and Doly, 1979) and analysed by enzymatic digestion by restriction enzymes.

b) Construction of plasmids pBIOC100 and pBIOC101 containing RGLSP-DGL and RGLSP-DGL-KDEL respectively and allow expression in the albumen of corn seeds The expression of the animal gene which codes for dog gastric lipase (DGL) in the albumen of corn seeds required the following regulator sequences:

1. the gene promoter of γzeine of corn (pγzeine) contained in the plasmid pγ63 described in Reina et al., 1990. The plasmid pγ63 results from the cloning of pγzeine at the HindIII and XbaI sites of a plasmid pUC18 containing, between its HindIII and EcoRI sites, the expression cassette "p35S-gus-tNOS" of pBI221 marketed by Clontech. It allows expression in the albumen of corn seeds.

2. the terminal transcription sequence, terminator polyA NOS, which corresponds to the non-coding region 3' of the gene of nopaline synthase of the plasmid Ti of *Agrobacterium tumefaciens* nopaline strain (Depicker et al., 1982).

The plasmid pBIOC100 where the sequence which codes for RGLSP-DGL is placed under the control of pγzeine was obtained by cloning at the sites "SacI treated by the enzyme T4 DNA polymerase and BamHI" of the plasmid pγ63, of the fragment "XbaI treated with Klenow-BglII" isolated from pBIOC40 (described above). The ligation was carried out with 100 ng of the vector and 50 ng of DNA fragments described above in a reaction medium of 10 μl in the presence of 1 μl of the buffer T4 DNA ligase×10 (Amersham) and 2.5 U of the enzyme T4 DNA ligase (Amersham) at 14° C. for 16 hours. The bacteria *Escherichia coli* Dh5α, rendered competent beforehand, were transformed (Hanahan, 1983). The plasmid DNA of the clones obtained, selected on a medium containing 50 μg/ml of ampicillin, was extracted by the alkaline lysis method (Birnboim and Doly, 1979) and analysed by enzymatic digestion by restriction enzymes. The resulting clone was called pBIOC100.

The plasmid pBIOC101 results from the substitution of fragment NcoI-AflIII of pBIOC100 by the fragment NcoI-AflII carrying the sequence which codes for the tetrapeptide KDEL (allowing directing in the endoplasmic reticulum) placed before the stop codon obtained by PCR amplification according to the processes described above. The 2 oligodeoxynucleotides used during this reaction were 5' AAT CAC TTG GAC TTT ATC TGG Gcc atg GAT GCC 3' (SEQ ID NO: 36; unique NcoI site) and 5' ATT ctt aag AAA CTT TAT TGC CAA ATG TTT GAA CGA TCG GGG AAA TTC GAC GCG TCT AGA ACT ATA GCT CAT CCT TAT TAT CTG TTC CCA TCA TGG 3' (SEQ ID NO: 37; the sequence which codes for KDEL and a unique AflII site). The hybridization temperature was 70° C. The cloning was carried out as described previously.

V. Example of the Production of Transgenic Rape Plants

Seeds of spring rape (*Brassica napus* cv WESTAR or Limagrain stock) are disinfected for 40 minutes in a 15% solution of Domestos. After rinsing 4 times with sterile water, the seeds are germinated in an amount of 20 seeds per pot of 7 cm diameter and 10 cm height on a mineral medium of Murashige and Skoog (Sigma M 5519) with 30 g/l of sucrose, solidified with 5 g/l of agar gel. These pots are placed in a growing room at 26° C. with a photoperiod of 16 h/8 h under a luminous intensity of the order of 80 μE m$^{-2}$ S-1.

After 5 days of germination, the cotyledons are removed under sterile conditions by cutting each petiole about 1 mm above the cotyledonary node.

In parallel, *Agrobacterium tumefaciens*, strain LBA4404, containing the plasmid pBIOC29 (or pBIOC25), that is to say the plasmid pGAZE into which has been inserted the sequence which codes for dog gastric lipase fused to that which codes for a directing signal PPS (or PS), under control of the promoter pCRU (or pd35S), is precultured in a conical flask of 50 ml for 36 h at 28° C. in 10 ml of bacterial medium 2YT (Sambrook et al., 1989), supplemented with the antibiotics which can be used for selection of the strain used.

This preculture is used to seed, in an amount of 1%, a new bacterial culture prepared under the same conditions. After 14 h, the culture is centrifuged for 15 min at 3,000 g and the bacteria are taken up in an equivalent volume of the liquid germination medium. This suspension is divided among Petri dishes of 5 cm diameter in an amount of 5 ml/dish.

The cut end of the petiole is immersed for a few seconds in the agrobacterial solution thus prepared and the petiole is then pushed a few millimeters into the regeneration medium. This medium has the same base composition as the germination medium, with an addition 4 mg/l of benzyl-aminopurine (BAP), a phytohormone which promotes neoformation of buds. Ten explants (cotyledon with petiole) are grown per Petri dish of 9 cm diameter (Greiner reference 664102).

After 2 days of coculture under the same environmental conditions as the germination, the explants are planted out into Phytatray boxes (Sigma, reference P1552) containing the previous medium supplemented with a selective agent: 45 mg/l of kanamycin sulphate (Sigma, reference K4000) and a bacteriostatic: mixture of 1/6 (by weight) of the potassium salt of clavulanic acid and 5/6 of the sodium salt of amoxicillin (Augmentin, injectable) in an amount of 600 mg/l.

The explants are planted out under sterile conditions on new medium under the same conditions on two subsequent occasions, at an interval of 3 weeks.

The green buds which have appeared at the end of the second or third planting out are separated from the explant and grown individually in transparent pots of 5 cm diameter and 10 cm height containing a medium identical to the previous but devoid of BAP. After growing for 3 weeks, the stem of the transformed bud is cut and the bud is planted out in a pot of fresh medium. At the end of three to four weeks, the roots are sufficiently developed to allow acclimatization of the plantlet in a phytotron. The buds which are not green or have not taken root are removed. These plantlets are then transplanted into bowls with 7 cm sides filled with soil (standard NF U44551: 40% brown peat, 30% sifted heath and 30% sand) saturated with water. After two weeks of acclimatization in the phytotron (temperature 21° C., photoperiod 16 h/8 h and 84% relative humidity), the plantlets are repotted in pots of 12 cm diameter filled with the same soil enriched with slow-acting fertilizer (Osmocote, in an amount of 4 g/l of soil) and then transferred to a greenhouse (class S2) regulated at 18° C. with two daily waterings with water for 2 minutes.

When the flowers appear, these are placed in bags (Crispac, reference SM 570y 300 mm*700 mm) in a manner such that cross-fertilization is prevented.

When the pods have reached maturity, these are harvested, dried and then crushed. The seeds obtained are used for analysis of the biochemical activity. The transgenic descendants are selected by germination on a medium containing kanamycin sulphate in an amount of 100 to 150 mg/l (depending on the genotypes). The working conditions are identical to those described above, except that the germinations are carried out in glass tubes with a single seed per tube. Only the plantlets which develop secondary roots in the first three weeks are acclimatized in the phytotron before being passed to the greenhouse.

VI. Example of the Production of Transgenic Solanaceae Plants a) Production of Transgenic Tobacco Plants The tobacco plants used for the transformation experiments (*Nicotiana tabacum* var. Xanthi NC and PBD6) are cultivated in vitro on the base medium of Murashige and Skoog (1962), to which are added vitamins according to Gamborg et al. (1968, Sigma reference M0404), sucrose in an amount of 20 g/l and agar (Merck) in an amount of 8 g/l. The pH of the medium is adjusted to 5.8 with a solution of potash, before autoclaving at 120° C. for 20 min. The tobacco plantlets are planted out by taking cuttings at the internodes every 30 days on this multiplication medium MS20.

All the in vitro cultures are carried out in a climatically controlled chamber under the conditions defined below:

luminous intensity of 30 $\mu E.m^{-2}.S^{-1}$; photoperiod of 16 h; thermal period of 26° C. during the day, 24° C. at night.

The transformation technique used is derived from that of Horsch et al. (1985).

*Agrobacterium tumefaciens*, strain LBA4404, containing the plasmids pBIOC29 or pBIOC26 or pBIOC25 is precultured for 48 h at 28° C., under agitation, in medium LB (Sambrook et al., 1989), to which adequate antibiotics (rifampicin and tetracycline) have been added. The preculture is then diluted 50-fold in the same medium and cultured under the same conditions. After one night, the culture is centrifuged (10 min, 3,000 g), the bacteria are taken up in an equivalent volume of liquid medium MS (30 g/l of sucrose) and this suspension is diluted 10-fold.

Explants of about 1 $cm^2$ are cut from the leaves of the plantlets described above. They are subsequently brought into contact with the bacterial suspension for 1 h and then dried rapidly on filter paper and placed on a coculture medium (solid MS30).

After 2 days, the explants are transferred to Petri dishes on regeneration medium MS30 containing a selective agent, kanamycin (200 mg/l), a bacteriostatic, Augmentin (400 mg/l), and the hormones necessary for induction of buds (BAP, 1 mg/l, and ANA, 0.1 mg/l). The explants are planted out on the same medium after growing for 2 weeks. After two additional weeks, the buds are planted out in Petri dishes on the development medium, composed of medium MS20 which kanamycin and Augmentin have been added. After 15 days, half the buds are planted out. Rooting takes about 20 days, at the end of which the plantlets can be cloned by cutting at the internodes or put out in a greenhouse.

b) Production of Transgenic Tomato Plants

The tomato seeds cv. UC82B are sterilized with 10% Domestos for 15 minutes and rinsed 3 times with sterile water. The last rinsing is carried out for 10 minutes under agitation.

The seeds thus sterilized are germinated on medium MSSV/2 (base medium of Murashige and Skoog (1962, Sigma reference M6899)/2 to which are added vitamins according to Nitsch (Thomas and Pratt, 1981), saccharose at 30 g/l, agar (Merck) at 8 g/l, pH 5.9, for 7 or 8 days in a climatically-controlled chamber (luminous intensity of 30 $\mu E.m^{-2}$, $S^{-1}$, photoperiod of 16 h/8 h, 26° C.).

The transformation technique used is derived-from that of Fillatti et al. (1987).

*Agrobacterium tumefaciens,* strain LBA4404, containing the plasmids pBIOC25 or pBIOC26 is precultured for 24 hours at 28° C. under agitation in medium LB to which adequate antibiotics (rifampicin and tetracycline) have been added. The preculture is then diluted 50-fold in the same medium and cultured under the same conditions for one night. The OD is measured at 600 nm, the agrobacteria are centrifuged (10 minutes, 3000 g) and taken up in a liquid medium KCMS (described in the publication by Fillatti et al., 1987) so as to obtain an OD of 0.8 at 600 nm.

Technical improvements were used in some stages of the protocol described by Fillatti et al. (1987).

The preculture of the explants and the coculture were carried out as described by Fillatti et al. (1987) except that the medium KCMS was supplemented by acetosyringone (200 mM).

The washing medium 2Z differs by the addition of cefotaxime at 500 mg/l instead of carbenicillin. The development medium used is composed of base medium of Murashige and Skoog (Sigma MS6899) to which are added vitamins according to Nitsch, saccharose at 20 g/l, kanamycin at 50 mg/l, augmentin at 200 mg/l, ANA at 1 mg/l and zeatin at 0.5 mg/l.

VII. Production of Transgenic Corn Plants a) Production and Use of Corn Callus as a Target for Genetic Transformation The genetic transformation of corn, whatever the method employed (electroporation; Agrobacterium, microfibres, particle gun), generally requires the use of rapid division undifferentiated cells which have retained the ability to regenerate entire plants. This type of cell includes the embryogenic friable callus (called type II) of corn.

These calluses are obtained from immature embryos of genotype Hl II or (A188×B73) according to the method and on the media described by Armstrong (Malze Handbook; (1994) M. Freeling, V. Walbot Eds.; pp. 665–671). The calluses obtained in this way are multiplied and maintained by successive plantings every fifteen days on the initiation medium.

Plantlets are then regenerated from these calluses by modifying the hormonal and osmotic balance of the cells according to the method described by Vain et al. (Plant Cell Tissue and Organ Culture (1989), 18:143–151). These plants are then acclimatized in a greenhouse where they can be crossed or self-fertilized.

b) Use of a Particle Gun for the Genetic Transformation off Corn

The preceding paragraph describes the production and the regeneration of cell lines necessary for the transformation; a genetic transformation method is described here which leads to a stable integration of the modified genes in the genome of the plant. This method depends on the use of a particle gun identical to that described by J. Finer (Plant Cell Report (1992) 11:323–328); the target cells are callus fragments described in paragraph 1. These fragments with a surface area of 10 to 20 mm$^2$ were arranged, 4 hours before bombardment, at the rate of 16 fragments per dish in the centre of a Petri dish containing a culture medium identical to the initiation medium, to which is added 0.2 M of mannitol+0.2M of sorbitol. The plasmids carrying the genes to be introduced are purified on a Qiagen® column, following the manufacturer's instructions. They are then precipitated on particles of tungsten (M10) following the protocol described by Klein (Nature (1987) 327:70–73). The particles thus coated are fired towards the target cells using the gun and in accordance with the protocol described by J. Finer (Plant Cell Report(1992) 11:323–328).

The dishes of calluses thus bombarded are then sealed using Scellofrais® then cultured in the dark at 27° C. The first plantings take place 24 hours later, then every fifteen days for 3 months on a medium identical to the initiation medium with a selection agent added to it the type and concentration of which can vary according to the gene used (see paragraph 3). The selection agents which can be used generally consist of the active compounds of certain herbicides (Basta®, Round up®) or certain antibiotics (Hygromycin, Kanamycin . . . ).

After 3 months or sometimes earlier, calluses are obtained whose growth is not inhibited by the selection agent, usually and for the most part is composed of cells resulting from the division of a cell having integrated into its gene pool one or more copies of the selection gene. The frequency with which such calluses are obtained is about 0.8 callus per bombarded dish.

These calluses are identified, individualized, amplified then cultured so as to regenerate the plantlets (cf. paragraph a). In order to avoid any interference with the non-transformed cells all these operations are carried out on culture media containing the selection agent.

The plants thus regenerated are acclimatized then cultivated in a greenhouse where they can be crossed or self-fertilized.

VIII. Analysis of the Expression of Dog Gastric Lipase in Transgenic Tobacco Plants a) Protocol The protocol for extraction of the lipase from tobacco leaves taken from the plants in the greenhouse is as follows: 1 g of leaves (fresh weight) is ground in liquid nitrogen and then at 4° C. in 5 ml of the buffer 25 mM Tris-HCl buffer, pH 7.5, to which 1 mM EDTA and 10 mM mercaptoethanol have been added (buffer A), or 25 mM glycine-HCl buffer, pH 3, to which 1 mM EDTA, 10 mM β-mercaptoethanol, 0.2% Triton X-100 and 250 mM NaCl have been added (buffer B). The total ground material is immediately centrifuged at 4° C. for 15 min at 10,000 g.

For tobacco seeds, the extraction is carried out in buffer B in an amount of 0.1 g of seeds per 4 ml of buffer.

The lipase activity is determined with the aid of a pH-STAT by the titrimetric method of Gargouri et al. (1986), in which the substrate used is tributyrin. The emulsion of tributyrin (4 ml per 30 ml of emulsion) is prepared in a vortex in the presence of bile salts (1.04 g/l), bovine albumin (0.1 g/l) and NaCl (9 g/l). The analysis comprises neutralization of the butyric acid liberated under the action of the lipase by a solution of sodium carbonate at a pH regulated at 5.5 and at 37° C. One unit of lipase corresponds to the amount of enzyme which causes the liberation of one micromole of fatty acids in 1 min at 37° C. under optimum pH conditions (5.5). Natural (purified) dog gastric lipase has a specific activity of 570 units/mg of protein. The lipase activity can be measured on the total ground material, on the sediment or on the centrifugation supernatant.

Analysis of the total soluble proteins on the centrifugation supernatant (buffer A) is carried out by the method of Bradford (1976).

A sandwich ELISA test (Carrière et al., 1993) is also carried out on the centrifugation supernatant with 2 populations of natural anti-DGL polyclonal antibodies. The first population includes the antibodies which react with human gastric lipase and have been purified by affinity using total antiserum on human gastric lipase grafted on a column of Affigel 10 (Aoubala et al., (1993). These antibodies are used to coat the wells of the ELISA plates in a concentration of 1 μg/ml. The 2nd population comprises antibodies which do not recognize human lipase. They are subsequently purified on a column of Sepharose, bound to protein A and then bound to biotin. Fixing of the antibody is detected by the indirect means of a streptavidin/peroxidase conjugate, the enzymatic activity of which is demonstrated by means of the substrate o-phenylenediamine. The results obtained are of qualitative value and are recorded with the aid of the symbols + and −. The extraction yield can be improved by adding to the extraction buffer a detergent of CHAPS type (3-(3-cholamidopropyl)dimethyl-ammonio-1-propane sulphonate) (SIGMA). In fact, in this case, the extraction yields in the supernatant increase by about 100% (cf. Table 1).

TABLE 1

Lipase activity (U/gFW) in the extracts obtained from 4 tobacco plants originating from the genetic transformation with pBIOC25, in the presence of 1% CHAPS.

| Plants | NaCl 0.2 M/EDTA 1 mM pH 3.0 | NaCl 0.2 M/EDTA 1 mM pH 3.0 + 1% CHAPS |
|---|---|---|
| 1 | 80 | 112 |
| 2 | 40 | 104 |
| 3 | 43 | 109 |
| 4 | 54 | 92 | b) Expression with Plant Signal Peptides; Analyses on Tobacco Leaves and Seeds transformed with pBIOC25 and pBIOC26; ELISA Test The results obtained on 98 TO plants of the genotype Xanthi (15 to 20 leaf stage) are shown in Table 2. The analyses were all carried out on the ground mixture of leaves or seeds before centrifugation. For each construct, the activities measured show a wide variability according to the transformants. About 20% of the plants have no activity or an activity which is too weak for detection. The mean activities and the maximum activities are given in Table 2.

The amounts of total proteins are similar for the 3 constructs, with means of 7 and 8 mg/g of FW in the leaves and 34, 31 and 38 mg/g of FW in the seeds.

The mean lipase activity in the transformed leaves with the construct pBIOC26 is 34 U/g of FW, that is to say 0.8% expression with respect to the total proteins. In the seeds, the mean activity is 36 U/g of FW, that is to say 0.2%. The maximum activity obtained on one of the transformants is 146 U/g of FW (leaves; 2.5% expression) and 148 U/g of FW (seeds; 0.7% expression).

The enzymatic activities analyzed on the plants transformed with the construct pBIOC25 are similar. The mean activity in the leaves is 34 U/g of FW (0.8% expression) and the maximum activity is 134 U/g of FW (3% of the total proteins). In the seeds, the mean activity is 42 U/g of FW (0.3%) and the maximum activity is 159 U/g of FW (1%).

For plants transformed with the construct pBIOC29, no activity is detected in the leaves (seed-specific promoter). In the seeds, the mean activity is 12 U/g of FW (0.7% expression) and the maximum activity is 137 U/g of FW (0.7%).

The expression in the leaves and seeds of the same transformation event generally correlates well.

The results of the ELISA tests also agree with those of the analyses of the enzymatic activity, that is to say a plant having a lipase activity gives a positive result in the ELISA test.

Results obtained subsequently on these same plants show that the lipase activity can vary in the course of development of the plant. In fact, a plant of which the expression, with respect to the total proteins, was 3% at the 12–15 leaf stage gave an expression of 6% during a subsequent analysis (older plant having flowered).

TABLE 2

EXPRESSION OF LIPASE IN THE LEAVES AND SEEDS OF XANTHI TOBACCO.

| | | | LIPASE ACTIVITY | |
|---|---|---|---|---|
| CONSTRUCT | ORGAN | TOTAL PROTEINS mg/g of FW min-max (mean) | U/g of FW min-max (mean) | Expression (% of total proteins) min-max (mean) |
| pBIOC26 | Leaves (n = 34) | 3–15 (7) | 0–145.6 (34.4) | 0–2.5 (0.8) |
| | Seeds (n = 34) | 24–43 (34) | 0–147.6 (36.3) | 0–0.7 (0.2) |
| pBIOC25 | Leaves (n = 35) | 3–18 (8) | 0–133.5 (34) | 0–3 (0.8) |
| | Seeds (n = 35) | 17–35 (31) | 0–158.5 (41.9) | 0–1 (0.3) |
| pBIOC29 | Seeds (n = 29) | 29–55 (38) | 0–137.4 (11.8) | 0–0.7 (0.1) |

FW, fresh weight; min, value obtained for the transformation event expressing the least; max, value obtained for the transformation event expressing the most; n, number of transformation events analyzed.

b) Expression with the Signal Peptide of RGL; Analyses of the Lipase Activity on tobacco Leaves The results obtained on 44 TO plants of genotypes Xanthi and PBD6 (15 to 20 leaf stage) are as follows:

The analyses were all carried out on the ground mixture of leaves before centrifugation. The activities analyzed show a wide variability according to the transformants. About 20% of the plants have no activity or an activity which is too weak for detection. The mean lipase activities in the leaves transformed with the construct pBIOC41 is 38 U/g FW for the genotype Xanthi and 48 U/g FW for the genotype PBD6. The maximum activities are 152 and 226 U/g FW respectively.

IX. Analysis of the Expression of Dog Gastric Lipase in Transgenic Tomato Plants a) Protocol d The protocol for the extraction of the lipase from the tomato leaves and fruits is similar to that described for the tobacco leaves, except that 1 g of fresh material is taken up in 4 ml of buffer B. The lipase activity is determined as described for the tobacco leaves.

b) Analysis in Tomato Fruits

The fruits of thirty primary transformants were analyzed.

The lipase activity analyzed in the fruits is variable depending on the fruits for the same transformant. It is an average of 5 U/g FW for ripe fruit and 35 U/g FW for unripe fruit, independent of the construct tested (pBIOC25 or pBIOC26).

It should be noted that during the ripening of fruit the activity reduces. For example, for a given primary transformant, the lipase activity is 132 U/g FW for a green fruit with a diameter of 10 mm, 44 U/g FW for a red-green fruit with a diameter of 33 mm and 36 U/g FW for a red fruit with a diameter of 45 mm.

X. Immunodetection of the "Western" Type of the Recombinant DGL a) DGL Expressed in Transgenic Tobacco and Rape Leaves and Seeds a.1) Expression with Plant Signal Peptides; Immunodetection in Tobacco and Rape Leaves and Seeds Transformed by pBIOC25, pBIOC26 and pBIOC29

Immunodetection experiments of the "western" type ("western blots") (Renart and Sandoval, 1984) on the dog gastric lipase were carried out on the proteins of tobacco leaves and tobacco and rape seeds extracted with buffers A and B (see the extraction protocol above). To carry out these experiments, the proteins extracted (30 µg of total proteins per sample) are first separated over 12.5% of denaturing polyacrylamide gel in accordance with the technique of Laemmli U.K. (1970) and are then transferred on to a nitrocellulose membrane. An anti-dog lipase polyclonal antibody obtained in the guinea-pig is used as the probe and the detection is carried out by means of an anti-IgG antibody of the guinea-pig labelled with alkaline phosphatase.

The control protein is natural dog gastric lipase, which migrates in the form of a single band at an apparent molecular weight of about 50 kDa. The migration of the dog gastric lipase is slightly retarded in the presence of the extract of non-transformed tobacco leaves.

No band is detected in the protein extracts of non-transformed leaves and seeds of tobacco and rape. The lipase produced in the tobacco leaves is in the form of 2 bands. The band which is the largest quantitatively has an apparent molecular weight of about 37 kDa and corresponds to the abovementioned polypeptide (Δ54). The minor band has an apparent molecular weight of about 49 kDa and corresponds to the abovementioned polypeptide (Δ4). In the protein extracts of seeds, only the band of lower molecular weight is visible.

a.2) Expression with the Signal Peptide of RGL; Immunodetection in Tobacco Leaves and Seeds Transformed with pBIOC41

Western blots (Renart and Sandoval, 1984) were carried out on the proteins of tobacco leaves and seeds extracted with buffer B (see the extraction protocol above). The proteins extracted are first separated over denaturing polyacrylamide gel (SDS-PAGE) in accordance with the technique of Laemmli (1970) and are then transferred on to a nitrocellulose membrane. An anti-dog lipase polyclonal antibody obtained in the guinea-pig is used as the probe and the detection is carried out by means of an anti-guinea pig antibody labelled with alkaline phosphatase.

Control protein is dog gastric lipase migrates in the form of a single band at an apparent molecular weight of about 50 kDa. No band is detected in the protein extracts of non-transformed leaves of tobacco. The lipase produced in the leaf extracts is in the form of a major band at an apparent molecular weight of about 48–49 kDa and corresponds to the abovementioned polypeptide.

In tobacco seeds transformed with the construct pBIOC41, the recombinant lipase is in the same form as in the leaves.

b) DGL in a Protein Extract of Transformed Tobacco Leaves: Deglycosylation Experiment The protocol for extraction of the proteins for the deglycosylation experiments is as follows: 0.5 g of leaves (fresh weight) is ground in liquid nitrogen and then at 4° C. in 1 ml of denaturation buffer (100 mM phosphate buffer, pH 7.5, to which 1% β-mercaptoethanol, 25 mM EDTA and 1% SDS have been added). The ground material is centrifuged at 4° C. for 15 min at 10,000 g. The supernatant is incubated for 5 min at 100° C. in order to denature the proteins and then centrifuged for 2 min at 10,000 g. The supernatant is then diluted 10-fold in the deglycosylation buffer (100 mM phosphate buffer, pH 7.5, to which 1% β-mercaptoethanol, 25 mM EDTA, 0.1% SDS and 1% octyl glucoside have been added). The enzyme (N-glycosidase F, PNGase Boehringer) is added in an amount of 1 U per 100 µl of supernatant. A control without enzyme is carried out for each sample. The deglycosylation of the control protein (dog or rabbit gastric lipase) takes place under the same conditions. The various protein samples are incubated at room temperature for 8 hours. The proteins are then separated by electrophoresis over polyacrylamide gel and transferred on a nitrocellulose membrane as described in the preceding paragraph.

According to the "western blots" results, the gastric lipase used as the control has an apparent molecular weight of about 50 kDa. After deglycosylation, its apparent molecular weight is only about 43 kDa.

The lipase produced in the tobacco leaves, after incubation without PNGase under the conditions described above, appears in the form of 3 bands of apparent molecular weights 49 (polypeptide (Δ4)), 37 (polypeptide (Δ54)) and 28 kDa. The band of molecular weight 28 kDa is without doubt the result of a proteolysis which has taken place during the incubation for 8 hours at room temperature. After deglycosylation, the molecular weights of the 3 bands are reduced by about 1 to 2 kDa, which shows that the proteins produced in the tobacco leaves are glycosylated.

c) DGL Expressed in Transgenic Tomato Leaves and Fruits

Immunodetection experiments of the "western" type on the dog gastric lipase were carried out on the proteins of tomato leaves and fruits extracted with buffer B (see the extraction protocol above). To carry out these experiments, the proteins extracted (15 µg and 6 µg of total soluble proteins for the leaves and fruits respectively) are separated over denaturing polyacrylamide gel as described in paragraph X.a).

Control protein natural gastric lipase migrates in the form of a single band at an apparent weight of about 50 kDa.

No band is detected in the protein extracts of non-transformed tomato leaves and fruits.

The lipase produced in the tomato leaves and fruits is in the form of 2 bands, whichever construct is used (pBIOC25 or pBIOC26). The band which is the largest quantitatively has an apparent weight of about 37 kDa and corresponds to the abovementioned polypeptide (Δ54). The minor band has an apparent molecular weight of about 49 kDa and corresponds to the abovementioned polypeptide (Δ4).

XI. Purification of the Dog Gastric Lipase from Plants a) Purification of DGL from Tobacco Leaves The activity of the dog gastric lipase produced in the tobacco leaves is determined by a titrimetric method, the regulated pH being kept at 5.5 and the temperature at 37° C. with the aid of a pH-stat (Mettler-Toledo-DL25), using tributyrin as the substrate: 1 ml of tributyrin is emulsified in 29 ml of an aqueous solution of 0.15 M NaCl in a vortex. The analysis comprises neutralizing the butyric acid liberated under the action of the lipase by addition of 0.02 N sodium carbonate, while the emulsion is maintained by vigorous mechanical agitation. One lipase unit corresponds to 1 micromole of fatty acid liberated per minute under these conditions of pH and temperature.

After the first chromatography stage, the lipase activity is demonstrated with an analytical sample of 0.5 ml on an emulsion of 1 ml of tributyrin in 29 ml of a solution of 0.15 M NaCl, 2 mM sodium taurodeoxycholate and 1.5 µM bovine serum albumin in accordance with the analysis described by Gargouri et al. (1986).

1 gram of lyophilized leaves is ground at 4° C. in 30 ml of 20 mM glycine buffer, pH 2.5, and the mixture is stirred gently for 15 minutes. During the steeping, the pH is kept at 2.5 by addition of iN HCl. The product of the steeping is centrifuged at 15,000 g for 5 minutes. The pH of the supernatant is adjusted to 4 by addition of 1N NaOH. After filtration over MIRACLOTH (Calbiochem), all the supernatant is applied to a cation exchange resin column (S-Sepharose Fast Flow resin—Pharmacia) of 10 ml (diameter 1.6 cm) equilibrated in a buffer of 20 mM sodium acetate, pH 4.0, and 20 mM NaCl at a flow rate of 1 ml per minute. Fractions of 2 ml are collected. After passage of the supernatant, the column is washed with 40 ml of the equilibration buffer. The proteins retained on the column are eluted in accordance with the following protocol:

linear gradient in mM sodium acetate buffer, pH 4.0, of 20 mM to 210 mM NaCl in the course of 30 minutes for elution of a first set of peaks of proteins which do not contain lipase activity, the test being carried out on analytical samples of 1 ml, plateau at 210 mM NaCl for 20 minutes, linear gradient in 20 mM sodium acetate buffer, pH 4.0, of 210 mM to 500 mM NaCl in the course of 30 minutes for elution of a second set of peaks. The lipase activity-measured on analytical samples of 0.5 ml is eluted during this second gradient at an ionic strength of between 300 and 400 mM.

The active fractions are collected and concentrated with the aid of an OMEGACELL concentration cell of molecular weight limit 30 kDa (Filtron Technology Corporation).

The concentrate is dialysed for 12 hours against a buffer of 10 mM Tris-HCl, pH 8, and then applied to an anion exchange resin column (MonoQ HR 5/5 of diameter 0.5 cm and height 5 cm—Pharmacia) equilibrated in 10 mM Tris-HCl buffer, pH 8. The lipase activity is measured on an analytical sample of 0.5 ml. The flow rate is kept at 1 ml per minute, that is to say a pressure of 2.0 mPa. After elution of the fraction which is not retained and washing of the column with 10 ml of 10 mM Tris-HCl buffer, pH 8, a linear gradient of ionic strength from 0 to 400 mM NaCl is applied in the course of 60 minutes. The lipase activity is eluted for an ionic strength between 100 mM and 200 mM.

The active fractions are collected and concentrated with the aid of an OMEGACELL concentration cell of molecular weight limit 30 kDa. The concentrate constitutes the purified form of the dog gastric lipase extracted from tobacco leaves.

The concentration of proteins is determined in accordance with the method of M. Bradford (1976) on the concentration supernatants and in accordance with the method of O. H. Lowry (1951) for the solutions after the first ion exchange chromatography.

The various stages of the purification are analyzed by electrophoresis over denaturing polyacrylamide gel (SDS-PAGE 12.5%) in accordance with the technique of U.K. Laemmli (1970). The proteins separated in this way on the polyacrylamide gel are, on the one hand, detected by staining with Coomassie blue and, on the other hand, transferred on a nitrocellulose membrane by the technique of semi-dry electrotransfer (Transblot SD, BIORAD) in a buffer of 20 mM Tris base, 150 mM glycine and 20% ethanol at 2.3 mA per cm$^2$ of membrane. The recombinant dog gastric lipase transferred on the nitrocellulose membrane is detected by immunodetection in accordance with the following protocol:

labelling of the target protein by an dog gastric anti-lipase polyclonal antibody obtained in the guinea-pig and diluted to 1/5,000 in PBS buffer, to which lipid-free milk powder in an amount of 5% and Tween 20 in an amount of 0.1% have been added, for 1 hour at room temperature, rinsing of the membrane in three successive baths of PBS buffer, to which lipid-free milk powder in an amount of 1% and Tween 20 in an amount of 0.1% have been added, for 10 minutes for each bath, labelling with an anti-guinea-pig antibody bound to peroxidase (Sigma) diluted to 1/2,000 in PBS buffer, to which lipid-free milk powder in an amount of 1% and Tween 20 in an amount of 0.1% have been added, for 1 hour at room temperature, rinsing of the membrane in three successive baths of PBS buffer, to which lipid-free milk powder in an amount of 1% and Tween 20 in an amount of 0.1% have been added, for 10 min for each bath, detection by the action of the peroxidase on 4-chloro-1-naphthol (Sigma) in the presence of $H_2O_2$ to produce a blue coloration which is stable in the course of time.

The lipase produced in the leaves is in the form of two bands of about 49 (polypeptide (Δ4)) kDa and 37 (polypeptide (Δ54)) kDa.

b) Variant for the Purification of DGL from Tobacco Leaves

The activity of the dog gastric lipase produced in the tobacco leaves is determined by the titrimetric methods described by Gargouri et al. (1986) with the aid of a pH-stat (METTLER-TOLEDO-DL25).

The analysis on short-chain triglycerides is carried out using tributyrin as the substrate: 1 ml of tributyrin is emulsified in 29 ml of an aqueous solution of 0.15 M NaCl, 1.5 µM of Bovine Serum Albumin (BSA) and 2 mM of sodium taurodeoxycholate (NaTDC). The regulated pH is kept at 5.0 and the temperature at 37° C.

The analysis comprises neutralizing the butyric acid liberated under the action of the lipase by addition of 0.02 N sodium carbonate, while the emulsion is maintained by vigorous mechanical agitation.

The analysis on long-chain triglycerides is carried out using an aqueous emulsion with 30% purified soya bean oil, 1.2% of purified egg phospholipids, 1.67% of anhydrous glycerol (Intralipid™ 30%—PHARMACIA AB Stockholm, Sweden) as the substrate. Ten ml of this suspension is emulsified in 20 ml of an aqueous solution of 0.15 M NaCl, 30 µM of BSA and 3.5 mM of $CaCl_2$. The regulated pH is kept at 4.0 and the temperature at 37° C.

The analysis consists of neutralizing the fatty acids liberated under the action of the lipase by addition of 0.2 N sodium carbonate, after a jump in the pH from 4 to 9 while the emulsion is maintained by vigorous mechanical agitation.

One lipase unit corresponds to 1 micromole of fatty acid liberated per minute under the defined conditions of pH and temperature for each of the substrates.

2 grams of lyophilized leaves is ground up at 4° C. in 60 ml of 0.2 M NaCl, pH 3, and the mixture is gently agitated for 15 minutes at 4° C. During this steeping, the pH is kept at 3 by the addition of 1N HCl. The product of the steeping (homogenate) is centrifuged at 10,000 g for 10 minutes. After filtration over MIRACLOTH (Calbiochem) and a 0.45μ MILLIPORE filter, all the supernatant is injected into a cation exchange resin column (RESOURCE S 6 ml—Pharmacia—16 mm i.d.×30 mm) equilibrated in a buffer of 20 mM sodium acetate, 0.2 M NaCl pH 3 at a flow rate of 8 ml/minute (240 cm h−1).

After passage of the non-retained fraction, the column is washed with 30 times its volume of the equilibration buffer. The proteins retained on the column are eluted with a linear gradient in 20 mM sodium acetate buffer, pH 3, of 0.2 M NaCl to 0.5 M NaCl in 7 column volumes. Fractions of 4 ml are collected.

The lipase activity measured on analytical samples of 0.5 ml is eluted at an ionic strength of 0.35 M NaCl.

The active fractions are collected and concentrated with the aid of an OMEGACELL concentration cell (Filtron Technology Corporation) with a molecular weight limit of 30 kDa.

Determination of the protein concentration is carried out in accordance with the method of O. H. Lowry (1951).

An example of polyacrylamide gel and the result of the transfer of this gel onto a nitrocellulose membrane and detection from a dog gastric anti-lipase antibody are shown (FIG. 9 and 10), the detection was carried out by the action of peroxydase on Luminol in the presence of activator (ECL western blotting—AMERSHAM LIFE SCIENCE) and recording on a photographic film.

The presence of glycanic residues on the protein was determined according to the following protocol:

immobilization of the protein on a microcellulose membrane treatment with periodate specific reaction with streptavidin coupled with alkaline phosphatase coloured reaction with alkaline phosphate (GLYCOTRACK OXFORD GYLOSYSTEM).

An example of membrane detection of glycanic residues is shown (FIG. 11).

The purity of the fractions is ensured by high performance liquid chromatography.

Chromatograph WATERS 625 LC

Diode array detector WATERS 991

Column VYDAC C4

Elution conditions:

| Time (min) | Flow rate (ml/min) | % A | % B |
|---|---|---|---|
| 0 | 1 | 100 | 0 |
| 35 | 1 | 40 | 60 |
| 40 | 1 | 40 | 60 |
| 45 | 1 | 20 | 80 |
| 50 | 1 | 100 | 0 |

Buffer A: 89.9% H2O 10% Acetonitrile, 0.1% trifluoroacetic acid

Buffer B: 100% Acetonitrile.

Purification table: recombinant DGL

| | Total units* | mg of proteins | Specific activity | Purification factor | Yield |
|---|---|---|---|---|---|
| Homogenate | 3200 | / | / | / | / |
| Supernatant | 2800 | 230 | 13 | 1 | 88% |
| Outlet Resource S | 1600 | 6 | 250 | 20 | 50% |

*Tributyrin units

Comparative Specific Activities of Natural Dog Gastric Lipase (n-DGL) and Recombinant Dog Gastric Lipase (r-DGL)

| | n-DGL* | r-DGL extract from tobacco leaves |
|---|---|---|
| Tributyrin | 570 U/mg | 250 U/mg |
| Intralipid 30% | 1000 U/mg | 950 U/mg |

*ref: Carriere et al (1991) Eur. J. Biochem, 202, 75–83.

c) Purification of DGL from Rape Seeds

The activity of the recombinant DGL produced in rape seeds is determined in the same way as in the case of extraction from leaves.

Ten grams of rape seeds are ground up in liquid nitrogen. The flour obtained is delipidated with hexane by a first steeping at 4° C. under gentle agitation for 12 hours. The whole is decanted, the hexane is eliminated. The flour is rinsed twice with 100 ml of hexane under gentle agitation for ½ hour at 4° C. for each rinsing. The hexane is eliminated by decanting. The flour is dried in a rotary evaporator (HEIDOLPH 94200). The delipidated flour is stored at −20° C.

Extraction of the DGL is carried out from the delipidated flour by steeping at 4° C. in a 0.2 M aqueous solution of NaCl pH3 (1N HCl) for minutes at the rate of 2 ml of aqueous solution per 0.1 g of flour. The resultant material from the steeping is centrifuged at 10,000 g for 10 minutes at 4° C.

The pellet is eliminated. The supernatant constitutes the seed extract.

The seed extract is dialyzed against a buffer of 10 mM of sodium acetate, pH4, 140 mM of NaCl, 3 mM of KCl then applied to an immunoaffinity column constituted by dog gastric anti-lipase polyclonal antibodies obtained from guinea-pigs coupled to a resin (hydrazide Avidgel—BIOPROBE INTERNATIONAL, Inc.).

The resin/seed extract contact is for 30 minutes at 4° C. under gentle agitation. The resin is then rinsed with 10 column volumes of buffer, 10 mM sodium acetate, pH4, 150 mM NaCl, 3 mM KCl. The DGL is eluted with 5 column volumes of buffer, 0.2 M glycine, pH 2.8, 150 mM NaCl. The collected fractions have a volume equal to 1 column volume and contain 1/20th V/V of 1M Tris buffer, pH 9. Analysis by electrophoresis over polyacrylamide gel in denaturing medium shows a protein of molecular weight of about 37 kDa.

XII. Synthesis of Fatty Acid Esters

The tests were carried out with non-transformed rape seeds, the lipase being provided:

either in the form of an immobilized enzymatic preparation (lipozyme (NOVO)) or in the free form (rabbit gastric lipase (JO 4002)), or in the form of tobacco seeds transformed with the gene of dog gastric lipase (tobacco T14-44 0.85% expression).

The esterification reactions are carried out at 37° C. for 16 hours in hermetically stoppered glass bottles placed on an agitation bench (250 rpm). The organic solvent used is hexane, in which the fatty acids are soluble The methanol is added in a stoichiometric amount with respect to the theoretical amount of triacylglycerol contained in the rape seeds.

The major component of the fatty acids of rape is oleic acid, and the reference control chosen is also a methyl ester of oleic acid. The synthesis is monitored by thin layer chromatography (TLC). The migration solvent is a mixture of hexane, diethyl ether and water (70:10:1). Detection on the plates is carried out under hot conditions after spraying with sulphuric acid (5%) in ethanol.

In a first test, 27 µl of methanol (0.66 mmol) and 0.02 g of lipozyme are added to 0.2 g of rape oil (0.22 mmol): no spot appears at the level of the reference methyl oleate (FIG. 6, column 2).

In the second test, the rape oil is replaced by 0.5 g of rape seeds ground in the dry state, and 1 ml of hexane is added: a methyl ester is synthesized (FIG. 6, column 5).

In the following tests, the conditions above are repeated with the following modifications: the amount of lipozyme is reduced to 0.006 g and the lipozyme is replaced by rabbit gastric lipase (0.007 g of JO 4002). Methyl oleate is synthesized in the presence of the lipozyme but not in the presence of JO 4002 (FIG. 7, column 2).

Finally, in the last tests, the lipase is provided by transformed tobacco seeds (1 g of tobacco seeds). A characteristic spot of a methyl ester appears (FIG. 8, column 3).

In conclusion, the results described above demonstrate that if extracts of rape seeds, alcohol and recombinant dog gastric lipase produced by transgenic tobacco are brought together, an esterification reaction which leads to the synthesis of a methyl ester which can be used as a biofuel is obtained.

Legend to the figures:

FIG. 1: Nucleotide sequence of the cDNA which codes for the DGL,

FIG. 2: Amino acid sequence of the DGL,

FIG. 3: Nucleotide sequence derived from the cDNA which codes for the DGL, coding for the DGL shown on FIG. 2, FIG. 4: Nucleotide sequence of the cDNA which codes for HGL and the amino acid sequence of HGL, FIG. 5: Amino acid sequence of HGL, FIG. 6: Detection on a TLC plate; 1: rape oil, no enzyme; 2: rape oil+lipozyme; 3: methyl ester of oleic acid; 4: rape seeds, no enzyme; 5: rape seeds+lipozyme, FIG. 7: Detection of a TLC plate; 1 and 4: rape seeds without enzyme; 2: rape seeds+JO4002; 3: methyl ester of oleic acid; 5: rape seeds+lipozyme, FIG. 8: Detection on a TLC plate; 1: monoolein, diolein, triolein; 2: methyl ester of oleic acid; 3: rape seeds+ transformed tobacco seeds.

BIBLIOGRAPHICAL REFERENCES

An et al. Plant Physiol., 81, 301–305 (1986).
An G., Plant Physiol., 81, 86–91 (1986).
Aoubala M., Daniel C., De Caro A., Ivanova M. G., Hirn M., Sarda L. and Verger R., Eur. J. Biochem. 211, 99–104 (1993).
Barta et al., Plant Mol. Biol., 6, 347–357 (1986).
Bednarek S. Y. and Ralkhel N. V., The Plant Cell, 3, 1195–1206 (1991).
Berg D. E., Berg C. M., Biotechnology, 1, 417–435 (1983).
Bernard C., C. R. Acad. Sci., 28, 249–253 (1849).
Bevan et al., Nature, 304, 184–187 (1983).
Bevan M., Nucleic Acids. Res., 12, 8711–8721 (1984).
Birnboim H. C., Doly J., Nucl. Acids. Res., 7, 1513–1523 (1979).
Bodmer M. W. et al., Biochem Biophys.Acta, 909, 237–244 (1987).
Bradford M., Anal Biochem., 72, 248 (1976).
Brodelius et al., FEBS Letters, 103, 93–97 (1979).
Brodelius, In: Moo-Young M. (Ed), Bioreactor Immobilized Enzymes and Cells: Fundamentals and Applications, Elsevier, Londres (1988).
Carrière et al., Eur. J. Biochem., 202, 75–83 (1991).
Carrière F., Laugier R., Barrowman J. A., Douchet I., Piymenko N. and Verger R., Scand. J. Gastroenterology, 28, 443–454 (1993).
Close J. J., Rodriguez R. L., Gene, 20, 305–316 (1982).
De La Penna et al., Nature, 325, 274–276 (1987).
Deno et al., J. Plant. Physiol., 131, 315–322 (1987).
Depicker et al., J. Mol. Appl. Genet., 1, 561–573 (1982).
Depigny-This et al., Plant. Mol. Biol., 20, 467–479 (1992).
De Zoeten et al., Virology, 172, 213–222 (1989).
Docherty A. J. P. et al., Nucl. Ac. Res., 13, 1891–1903 (1985).
Edelbaum et al., J. of Interferon Research, 12, 449–453 (1992).
Franck et al., Cell, 21, 285–294 (1980).
Fillatti J. J. Kiser J., Rose R. and Comai L., Biotechnologie, 5 726–730 (1987).
Gamborg O. L., Miller R.a. et Ojima K., Exp. Cell. Res., 50, 151–158 (1968).
Gargouri Y., Pieroni G., Rivière C., Saunière J-F., Lowe P. A., Sarda L. and Verger R., Gastroenterology, 91, 919–925 (1986).
Gargouri Y. et al., Biochem. Biophys. Act., 1006, 255–271 (1989).
Gaubier et al., Mol. Gen. Genet., 238, 409–418 (1993)
Giller et al., J. Biol. Chem., 16509–16516 (1992)
Guerineau F., Mullineaux P., Plant Molecular Biology LABFAX, Groy R. R. D. (Ed), Nios. Scientific Publishers, Blackwell Scientific Publishers, Blackwell Scientific Publications, 121–124 (1993).
Hanahan D., J. Mol. Biol., 166, 577–580 (1983).
Hein R., International Meeting of Production of Recombinant Proteins in Plants, Leicester, p. 22 (1994).
Herrera-Estrella et al., Nature, 303, 209–213 (1983a).
Herrera-Estrella et al., EMBO J., 2, 987–995 (1983b).
Hiatt and Ma, FEBS, 307, 71–75 (1992).
Hiatt et al., Nature, 342, 76–79 (1989).
Higo et al., Biosci. Biochem., 57, 1477–1481 (1993).
Holsters et al., Mol. Gen. Genet., 163, 181–187 (1978).
Horsch R. B., Fry J. E., Hoffman N. L., Eichholtz D. and Rogers S. G., Science, 227, 1229–1231 (1985).
Jouanin et al., Plant Sci., 53, 53–63 (1987).
Kay et al., Science, 236, 1299–1302 (1987).
Laemmli U.K., Nature, 227, 680–685 (1970).
Liu et al., Mol. Plant Microb. Interactions, 6, 144–156 (1993).
Lowry O. H., J. Biol. Chem., 173, 265–275 (1951).
Ma et al., International Meeting of Production of Recombinant Proteins in Plants, Leicester, p. 39–40 (1994).

McElroy et al., Mol. Gen. Genet., 231, 150–160 (1991).
Marx, Science, 216, 1305–1307 (1982).
Mason et al., Proc. Natl. Acad. Sci. USA, 89, 11745–11749 (1992).
Matsouka K., Nakamura K., Proc. Natl. Acad. Sci. USA, 88, 834–838 (1991).
Moloney et al., International Meeting of Production of Recombinant Proteins in Plants, Leceister, p. 36–38 (1994).
Moreau H. et al., Biochem. Biophys. Act., 960, 268–293 (1988).
Murakami et al., Plant Mol. Biol., 7, 343–355 (1986).
Murashige T. and Skoog F., Physiol. Plantarum, 15, 473–497 (1962).
Ni et al., Plant J., 7, 661–676 (1995).
Reina et al., Nucleic Acid Research, 18, 6426 (1990).
Renart J. and Sandoval I. V., Meth. Enzymol., 104, 455–460 (1984).
Russel D., International Meeting of Production of Recombinant Proteins in Plants, Leicester, p. 43 (1994).
Sambrook et al., Molecular Cloning Laboratory Manual, 2nd Edition, Cold Spring Harbor Laboratory Press (1989).
Sanford J. C., Trends in Biotechnology, 6, 299–302 (1988).
Sanger et al., Proc. Natl. Acad. Sci., 74, 5463–5467 (1977).
Schroeder M. R., Borkhsenious O. N., Matsouka K., Nakamura K. et Ralkhel N. V., Plant Physiol., 101, 451–458 (1993).
Shonheyder F., and Volquartz K., Acta Physiol. Scand., 9, 57–67 (1945).
Sijmons et al., Biotechnology, 8, 217–221 (1990).
Thomas B. R. and Pratt D., Theor. Appl. Genet., 59, 215–219 (1981).
Truve et al., Biotechnology, 11, 1048–1052 (1993).
Vandekerckhove et al., Biotechnology, 7, 929–932 (1989).
Volhard F., Z. Klin. Med., 42, 414–429 (1901).

What is claimed is:

1. A nucleotide sequence comprising an isolated cDNA which encodes dog gastric lipase (DGL) having a polypeptide sequence comprising SEQ ID No: 2, wherein said nucleotide sequence comprises SEQ ID No. 1 and regulatory elements comprising transcription promoter sequences and transcription terminator sequences which allow a plant cell to produce the polypeptide encoded by said cDNA.

2. A nucleotide sequence according to claim 1, characterized in that it contains:

downstream of said cDNA, a terminator selected from the group consisting of a polyA 35S of the cauliflower mosaic virus (CaMV) or a polyA NOS of *Agrobacterium tumefaciens*; and upstream of said cDNA, a promoter selected from the group consisting of a 35S promoter or a double-structured 35S (pd35S) promoter of CaMV, a promoter pCRU of the gene of cruciferin of the radish, a promoter pGEA1 or pGEA6 of *Arabidopsis thaliana*, a chimaeric promoter pSP of *Agrobacterium tumefaciens*, a promoter pAR-LAP of rice, or a promoter pγzeine of corn.

3. A nucleotide sequence according to claim 2, characterized in that it contains a sequence which codes for a peptide responsible for directing the recombinant DGL into a specific compartment of the plant cell.

4. A nucleotide sequence according to claim 2, selected from the group consisting of a sequence comprising, in the direction 5'→3', the promoter pd35S of CaMV, a sequence which codes for the signal peptide of sporamin A, the latter begin immediately followed by the nucleotide sequence of SEQ ID No:1, and then the terminator poly A 35S of CaMV;

a sequence comprising, in the direction 5'→3', the promoter pd35S of CaMV, the sequence which codes for the prepropeptide of sporamin A, the latter being immediately followed by the nucleotide sequence of SEQ ID No: 1, and then the terminator poly A 35S of CaMV;

a sequence comprising, in the direction 5'→3', the promoter pd35S of CaMV, the sequence which codes for a part of the signal peptide of RGL the latter being immediately followed by the cDNA of SEQ ID No: 1, and then the terminator poly A 35S of CaMV,;

a sequence comprising, in the direction 5'→3', the promoter pCRU of cruciferin, the sequence which codes for the signal peptide of sporamin A, the latter being immediately followed by the nucleotide sequence of SEQ ID No: 1, and then the terminator poly A 35S of CaMV,;

a sequence comprising, in the direction 5'→3', the promoter pCRU of cruciferin, the sequence which codes for the prepropeptide of sporamin A, the latter being immediately followed by the nucleotide sequence of SEQ ID No: 1, and then the terminator poly A 35S of CaMV;

a sequence comprising, in the direction 5'→3', the promoter pCRU of cruciferin, the sequence which codes for a part of the signal peptide of RGL, the latter being immediately followed by the cDNA of SEQ ID No: 1, then the terminator poly A 35S of CaMV;

a sequence comprising, in the direction 5'→3', the promoter pGEA1of *Arabidopsis thaliana*, the sequence which codes for a part of the signal peptide of RGL, the latter being immediately followed by the cDNA of SEQ ID No: 1, then the terminator poly A 35S of CaMV;

a sequence comprising, in the direction 5'→3', the promoter pGEA6 of *Arabidopsis thaliana*, the sequence which codes for a part of the signal peptide of RGL, the latter being immediately followed by the cDNA of SEQ ID No: 1, then the terminator poly A 35S of CaMV;

a sequence comprising, in the direction 5'→3', the promoter pAR-IAR of rice, the sequence which codes for a part of the signal peptide of RGL, the latter being immediately followed by the cDNA of SEQ ID No: 1, then the terminator poly A 35S of CaMV, or the terminator poly A NOS of *Agrobacterium tumefaciens*;

a sequence comprising, in the direction 5'→3', the promoter pγzeine of corn, the sequence which codes for a part of the signal peptide of RGL, the latter being immediately followed by the cDNA of SEQ ID No: 1, then the terminator poly A 35S of CaMV; and a sequence comprising, in the direction 5'→3', the promoter pγzeine of corn, the sequence which codes for a part of the signal peptide of RGL, the latter being immediately followed by the cDNA of SEQ ID No: 1, then the sequence which codes for the tetrapeptide KDEL then the terminator ply A 35S of CaMV.

5. A vector containing a nucleotide sequence according to claim 1 wherein said nucleotide sequence is located in a site of said vector which is not essential for its replication.

6. A host cell transformed by a vector according to claim 4.

7. A host cell according to claim 6, wherein said host cell is *Agrobacterium tumefaciens*.

8. A genetically transformed plant cell characterized in that it contains a recombinant nucleotide sequence according to claim 1, integrated into its genome in a stable manner.

9. A plant cell according to claim 8 wherein said plant cell is chosen from rape, tobacco, corn, pea, tomato, carrot, wheat, barley, potato, soy, sunflower, lettuce, rice, Lucerne and beetroot, or from parts of these plants.

10. A genetically transformed plant or plant part characterized in that it contains a recombinant nucleotide sequence according to claim 1, integrated into its genome in a stable manner, wherein said plant is chosen from rape, tobacco, corn, pea, tomato, carrot, wheat, barley, potato, soy, sunflower, lettuce, rice. Lucerne and beetroot.

11. A genetically transformed plant or plant part according to claim 10, wherein said plant part is chosen among leaves and/or fruits and/or seeds.

* * * * *

SEQUENCE LISTING

```
<160> NUMBER OF SEQ ID NOS: 37

<210> SEQ ID NO 1
<211> LENGTH: 1528
<212> TYPE: DNA
<213> ORGANISM: Canis familiaris
<220> FEATURE:
<221> NAME/KEY: CDS
<222> LOCATION: (1)..(1137)

<400> SEQUENCE: 1 ttg ttt gga aag ctt cat ccc aca aac cct gaa gtg acc atg aat ata      48
Leu Phe Gly Lys Leu His Pro Thr Asn Pro Glu Val Thr Met Asn Ile
1               5                   10                  15 agt cag atg atc acc tac tgg gga tac cca gct gag gaa tat gaa gtt      96
Ser Gln Met Ile Thr Tyr Trp Gly Tyr Pro Ala Glu Glu Tyr Glu Val
            20                  25                  30 gtg acc gaa gac ggt tat atc ctt ggg atc gac aga att cct tat ggg     144
Val Thr Glu Asp Gly Tyr Ile Leu Gly Ile Asp Arg Ile Pro Tyr Gly
        35                  40                  45 agg aaa aat tca gag aat ata ggc cgg aga cct gtt gca ttt ttg caa     192
Arg Lys Asn Ser Glu Asn Ile Gly Arg Arg Pro Val Ala Phe Leu Gln
    50                  55                  60 cac ggt ttg ctc gca tca gcc aca aac tgg atc tcc aac ctg ccc aac     240
His Gly Leu Leu Ala Ser Ala Thr Asn Trp Ile Ser Asn Leu Pro Asn
65                  70                  75                  80 aac agc ctg gcc ttc atc ctg gcc gac gcc ggg tac gac gtg tgg ctg     288
Asn Ser Leu Ala Phe Ile Leu Ala Asp Ala Gly Tyr Asp Val Trp Leu
                85                  90                  95 ggg aac agc agg ggc aac acc tgg gcc agg agg aat ctg tac tac tcg     336
Gly Asn Ser Arg Gly Asn Thr Trp Ala Arg Arg Asn Leu Tyr Tyr Ser
            100                 105                 110 ccc gac tcc gtc gaa ttc tgg gct ttc agc ttt gac gag atg gct aaa     384
Pro Asp Ser Val Glu Phe Trp Ala Phe Ser Phe Asp Glu Met Ala Lys
        115                 120                 125 tat gac ctt ccc gcc acc att gac ttc atc ttg aag aaa acg gga cag     432
Tyr Asp Leu Pro Ala Thr Ile Asp Phe Ile Leu Lys Lys Thr Gly Gln
    130                 135                 140 gac aag cta cac tac gtt ggc cat tcc cag ggc acc acc att ggt ttc     480
Asp Lys Leu His Tyr Val Gly His Ser Gln Gly Thr Thr Ile Gly Phe
145                 150                 155                 160
```

-continued

| | | | | | | | | | | | | | | | |
|---|---|---|---|---|---|---|---|---|---|---|---|---|---|---|---|
| atc | gcc | ttt | tcc | acc | aat | ccc | aag | ctg | gcg | aaa | cgg | atc | aaa | acc | ttc | 528 |
| Ile | Ala | Phe | Ser | Thr | Asn | Pro | Lys | Leu | Ala | Lys | Arg | Ile | Lys | Thr | Phe |
| | | | 165 | | | | 170 | | | | 175 | | | | |

```
atc gcc ttt tcc acc aat ccc aag ctg gcg aaa cgg atc aaa acc ttc      528
Ile Ala Phe Ser Thr Asn Pro Lys Leu Ala Lys Arg Ile Lys Thr Phe
            165                 170                 175 tat gca tta gct ccc gtt gcc acc gtg aag tac acc gaa acc ctg tta      576
Tyr Ala Leu Ala Pro Val Ala Thr Val Lys Tyr Thr Glu Thr Leu Leu
        180                 185                 190 aac aaa ctc atg ctc gtc cct tcg ttc ctc ttc aag ctt ata ttt gga      624
Asn Lys Leu Met Leu Val Pro Ser Phe Leu Phe Lys Leu Ile Phe Gly
    195                 200                 205 aac aaa ata ttc tac cca cac cac ttc ttt gat caa ttt ctc gcc acc      672
Asn Lys Ile Phe Tyr Pro His His Phe Phe Asp Gln Phe Leu Ala Thr
210                 215                 220 gag gta tgc tcc cgc gag acg gtg gat ctc ctc tgc agc aac gcc ctg      720
Glu Val Cys Ser Arg Glu Thr Val Asp Leu Leu Cys Ser Asn Ala Leu
225                 230                 235                 240 ttt atc att tgt gga ttt gac act atg aac ttg aac atg agt cgc ttg      768
Phe Ile Ile Cys Gly Phe Asp Thr Met Asn Leu Asn Met Ser Arg Leu
                245                 250                 255 gat gta tat ctg tca cat aat cca gca gga aca tcg gtt cag aac gtg      816
Asp Val Tyr Leu Ser His Asn Pro Ala Gly Thr Ser Val Gln Asn Val
            260                 265                 270 ctc cac tgg tcc cag gct gtt aag tct ggg aag ttc caa gct ttt gac      864
Leu His Trp Ser Gln Ala Val Lys Ser Gly Lys Phe Gln Ala Phe Asp
        275                 280                 285 tgg gga agc cca gtt cag aac atg atg cac tat cat cag agc atg cct      912
Trp Gly Ser Pro Val Gln Asn Met Met His Tyr His Gln Ser Met Pro
    290                 295                 300 ccc tac tac aac ctg aca gac atg cat gtg cca atc gca gtg tgg aac      960
Pro Tyr Tyr Asn Leu Thr Asp Met His Val Pro Ile Ala Val Trp Asn
305                 310                 315                 320 ggt ggc aac gac ttg ctg gcc gac cct cac gat gtt gac ctt ttg ctt     1008
Gly Gly Asn Asp Leu Leu Ala Asp Pro His Asp Val Asp Leu Leu Leu
                325                 330                 335 tcc aag ctc ccc aat ctc att tac cac agg aag att cct cct tac aat     1056
Ser Lys Leu Pro Asn Leu Ile Tyr His Arg Lys Ile Pro Pro Tyr Asn
            340                 345                 350 cac ttg gac ttt atc tgg gcc atg gat gcc cct caa gcg gtt tac aat     1104
His Leu Asp Phe Ile Trp Ala Met Asp Ala Pro Gln Ala Val Tyr Asn
        355                 360                 365 gaa att gtt tcc atg atg gga aca gat aat aag tagttctaga tttaaggaat   1157
Glu Ile Val Ser Met Met Gly Thr Asp Asn Lys
    370                 375 tattctttta ttgttccaaa atacgttctt ctctcacacg tggttttcta tcatgtttga   1217
gacacggtga ttgttcccat ggttttgatt tcagaaatgt gttagcatca acaatctttc   1277
cattggtaat ttttgaattt aaaatgattt ttaaatttgg ggcatctggg tggctcagtt   1337
ggctaagtcg tctgccttgg cttaagtcat gatctcgggg tcctaggatg gagccttgtg   1397
tctgggctcc tgccggggcg ggggtctgct ttctcctcctg ctgctccccc ctgctgctgt   1457
gtgcacacac gctctctctc tctcaaataa ataaataaat aaatacttaa taaaataaaa   1517
aaaaaaaaaa a                                                         1528
```

<210> SEQ ID NO 2
<211> LENGTH: 379
<212> TYPE: PRT
<213> ORGANISM: Canis familiaris

<400> SEQUENCE: 2

Leu Phe Gly Lys Leu His Pro Thr Asn Pro Glu Val Thr Met Asn Ile

```
1               5                    10                   15
Ser Gln Met Ile Thr Tyr Trp Gly Tyr Pro Ala Glu Tyr Glu Val
                20                   25                  30

Val Thr Glu Asp Gly Tyr Ile Leu Gly Ile Asp Arg Ile Pro Tyr Gly
            35                  40                  45

Arg Lys Asn Ser Glu Asn Ile Gly Arg Arg Pro Val Ala Phe Leu Gln
        50                  55                  60

His Gly Leu Leu Ala Ser Ala Thr Asn Trp Ile Ser Asn Leu Pro Asn
65                  70                  75                  80

Asn Ser Leu Ala Phe Ile Leu Ala Asp Ala Gly Tyr Asp Val Trp Leu
                85                  90                  95

Gly Asn Ser Arg Gly Asn Thr Trp Ala Arg Arg Asn Leu Tyr Tyr Ser
            100                 105                 110

Pro Asp Ser Val Glu Phe Trp Ala Phe Ser Phe Asp Glu Met Ala Lys
        115                 120                 125

Tyr Asp Leu Pro Ala Thr Ile Asp Phe Ile Leu Lys Lys Thr Gly Gln
    130                 135                 140

Asp Lys Leu His Tyr Val Gly His Ser Gln Gly Thr Thr Ile Gly Phe
145                 150                 155                 160

Ile Ala Phe Ser Thr Asn Pro Lys Leu Ala Lys Arg Ile Lys Thr Phe
                165                 170                 175

Tyr Ala Leu Ala Pro Val Ala Thr Val Lys Tyr Thr Glu Thr Leu Leu
            180                 185                 190

Asn Lys Leu Met Leu Val Pro Ser Phe Leu Phe Lys Leu Ile Phe Gly
        195                 200                 205

Asn Lys Ile Phe Tyr Pro His His Phe Asp Gln Phe Leu Ala Thr
    210                 215                 220

Glu Val Cys Ser Arg Glu Thr Val Asp Leu Leu Cys Ser Asn Ala Leu
225                 230                 235                 240

Phe Ile Ile Cys Gly Phe Asp Thr Met Asn Leu Asn Met Ser Arg Leu
                245                 250                 255

Asp Val Tyr Leu Ser His Asn Pro Ala Gly Thr Ser Val Gln Asn Val
            260                 265                 270

Leu His Trp Ser Gln Ala Val Lys Ser Gly Lys Phe Gln Ala Phe Asp
        275                 280                 285

Trp Gly Ser Pro Val Gln Asn Met Met His Tyr His Gln Ser Met Pro
    290                 295                 300

Pro Tyr Tyr Asn Leu Thr Asp Met His Val Pro Ile Ala Val Trp Asn
305                 310                 315                 320

Gly Gly Asn Asp Leu Leu Ala Asp Pro His Asp Val Asp Leu Leu Leu
                325                 330                 335

Ser Lys Leu Pro Asn Leu Ile Tyr His Arg Lys Ile Pro Pro Tyr Asn
            340                 345                 350

His Leu Asp Phe Ile Trp Ala Met Asp Ala Pro Gln Ala Val Tyr Asn
        355                 360                 365

Glu Ile Val Ser Met Met Gly Thr Asp Asn Lys
    370                 375
```

<210> SEQ ID NO 3
<211> LENGTH: 1048
<212> TYPE: DNA
<213> ORGANISM: Canis familiaris
<220> FEATURE:
<221> NAME/KEY: CDS
<222> LOCATION: (1)..(975)

<400> SEQUENCE: 3

```
ata ggc cgg aga cct gtt gca ttt ttg caa cac ggt ttg ctc gca tca       48
Ile Gly Arg Arg Pro Val Ala Phe Leu Gln His Gly Leu Leu Ala Ser
1               5                  10                  15 gcc aca aac tgg atc tcc aac ctg ccc aac aac agc ctg gcc ttc atc       96
Ala Thr Asn Trp Ile Ser Asn Leu Pro Asn Asn Ser Leu Ala Phe Ile
            20                  25                  30 ctg gcc gac gcc ggg tac gac gtg tgg ctg ggg aac agc agg ggc aac      144
Leu Ala Asp Ala Gly Tyr Asp Val Trp Leu Gly Asn Ser Arg Gly Asn
        35                  40                  45 acc tgg gcc agg agg aat ctg tac tac tcg ccc gac tcc gtc gaa ttc      192
Thr Trp Ala Arg Arg Asn Leu Tyr Tyr Ser Pro Asp Ser Val Glu Phe
    50                  55                  60 tgg gct ttc agc ttt gac gag atg gct aaa tat gac ctt ccc gcc acc      240
Trp Ala Phe Ser Phe Asp Glu Met Ala Lys Tyr Asp Leu Pro Ala Thr
65                  70                  75                  80 att gac ttc atc ttg aag aaa acg gga cag gac aag cta cac tac gtt      288
Ile Asp Phe Ile Leu Lys Lys Thr Gly Gln Asp Lys Leu His Tyr Val
                85                  90                  95 ggc cat tcc cag ggc acc acc att ggt ttc atc gcc ttt tcc acc aat      336
Gly His Ser Gln Gly Thr Thr Ile Gly Phe Ile Ala Phe Ser Thr Asn
            100                 105                 110 ccc aag ctg gcg aaa cgg atc aaa acc ttc tat gca tta gct ccc gtt      384
Pro Lys Leu Ala Lys Arg Ile Lys Thr Phe Tyr Ala Leu Ala Pro Val
        115                 120                 125 gcc acc gtg aag tac acc gaa acc ctg tta aac aaa ctc atg ctc gtc      432
Ala Thr Val Lys Tyr Thr Glu Thr Leu Leu Asn Lys Leu Met Leu Val
    130                 135                 140 cct tcg ttc ctc ttc aag ctt ata ttt gga aac aaa ata ttc tac cca      480
Pro Ser Phe Leu Phe Lys Leu Ile Phe Gly Asn Lys Ile Phe Tyr Pro
145                 150                 155                 160 cac cac ttc ttt gat caa ttt ctc gcc acc gag gta tgc tcc cgc gag      528
His His Phe Phe Asp Gln Phe Leu Ala Thr Glu Val Cys Ser Arg Glu
                165                 170                 175 acg gtg gat ctc ctc tgc agc aac gcc ctg ttt atc att tgt gga ttt      576
Thr Val Asp Leu Leu Cys Ser Asn Ala Leu Phe Ile Ile Cys Gly Phe
            180                 185                 190 gac act atg aac ttg aac atg agt cgc ttg gat gtg tat ctg tca cat      624
Asp Thr Met Asn Leu Asn Met Ser Arg Leu Asp Val Tyr Leu Ser His
        195                 200                 205 aat cca gca gga aca tcg gtt cag aac gtg ctc cac tgg tcc cag gct      672
Asn Pro Ala Gly Thr Ser Val Gln Asn Val Leu His Trp Ser Gln Ala
    210                 215                 220 gtt aag tct ggg aag ttc caa gct ttt gac tgg gga agc cca gtt cag      720
Val Lys Ser Gly Lys Phe Gln Ala Phe Asp Trp Gly Ser Pro Val Gln
225                 230                 235                 240 aac atg atg cac tat cat cag agc atg cct ccc tac tac aac ctg aca      768
Asn Met Met His Tyr His Gln Ser Met Pro Pro Tyr Tyr Asn Leu Thr
                245                 250                 255 gac atg cat gtg cca atc gca gtg tgg aac ggt ggc aac gac ttg ctg      816
Asp Met His Val Pro Ile Ala Val Trp Asn Gly Gly Asn Asp Leu Leu
            260                 265                 270 gcc gac cct cac gat gtt gac ctt ttg ctt tcc aag ctc ccc aat ctc      864
Ala Asp Pro His Asp Val Asp Leu Leu Leu Ser Lys Leu Pro Asn Leu
        275                 280                 285 att tac cac agg aag att cct cct tac aat cac ttg gac ttt atc tgg      912
Ile Tyr His Arg Lys Ile Pro Pro Tyr Asn His Leu Asp Phe Ile Trp
    290                 295                 300
```

```
gcc atg gat gcc cct caa gcg gtt tac aat gaa att gtt tcc atg atg      960
Ala Met Asp Ala Pro Gln Ala Val Tyr Asn Glu Ile Val Ser Met Met
305                 310                 315                 320 gga aca gat aat aag tagttctaga tttaaggaat tattctttta ttgttccaaa     1015
Gly Thr Asp Asn Lys
                325 atacgttctt ctctcacacg tggttttcta tca                                1048
```

<210> SEQ ID NO 4
<211> LENGTH: 325
<212> TYPE: PRT
<213> ORGANISM: Canis familiaris

<400> SEQUENCE: 4

```
Ile Gly Arg Arg Pro Val Ala Phe Leu Gln His Gly Leu Leu Ala Ser
1               5                   10                  15

Ala Thr Asn Trp Ile Ser Asn Leu Pro Asn Asn Ser Leu Ala Phe Ile
            20                  25                  30

Leu Ala Asp Ala Gly Tyr Asp Val Trp Leu Gly Asn Ser Arg Gly Asn
        35                  40                  45

Thr Trp Ala Arg Arg Asn Leu Tyr Tyr Ser Pro Asp Ser Val Glu Phe
    50                  55                  60

Trp Ala Phe Ser Phe Asp Glu Met Ala Lys Tyr Asp Leu Pro Ala Thr
65                  70                  75                  80

Ile Asp Phe Ile Leu Lys Lys Thr Gly Gln Asp Lys Leu His Tyr Val
                85                  90                  95

Gly His Ser Gln Gly Thr Thr Ile Gly Phe Ile Ala Phe Ser Thr Asn
            100                 105                 110

Pro Lys Leu Ala Lys Arg Ile Lys Thr Phe Tyr Ala Leu Ala Pro Val
        115                 120                 125

Ala Thr Val Lys Tyr Thr Glu Thr Leu Leu Asn Lys Leu Met Leu Val
    130                 135                 140

Pro Ser Phe Leu Phe Lys Leu Ile Phe Gly Asn Lys Ile Phe Tyr Pro
145                 150                 155                 160

His His Phe Phe Asp Gln Phe Leu Ala Thr Glu Val Cys Ser Arg Glu
                165                 170                 175

Thr Val Asp Leu Leu Cys Ser Asn Ala Leu Phe Ile Ile Cys Gly Phe
            180                 185                 190

Asp Thr Met Asn Leu Asn Met Ser Arg Leu Asp Val Tyr Leu Ser His
        195                 200                 205

Asn Pro Ala Gly Thr Ser Val Gln Asn Val Leu His Trp Ser Gln Ala
    210                 215                 220

Val Lys Ser Gly Lys Phe Gln Ala Phe Asp Trp Gly Ser Pro Val Gln
225                 230                 235                 240

Asn Met Met His Tyr His Gln Ser Met Pro Pro Tyr Tyr Asn Leu Thr
                245                 250                 255

Asp Met His Val Pro Ile Ala Val Trp Asn Gly Gly Asn Asp Leu Leu
            260                 265                 270

Ala Asp Pro His Asp Val Asp Leu Leu Leu Ser Lys Leu Pro Asn Leu
        275                 280                 285

Ile Tyr His Arg Lys Ile Pro Pro Tyr Asn His Leu Asp Phe Ile Trp
    290                 295                 300

Ala Met Asp Ala Pro Gln Ala Val Tyr Asn Glu Ile Val Ser Met Met
305                 310                 315                 320

Gly Thr Asp Asn Lys
                325
```

-continued

325

<210> SEQ ID NO 5
<211> LENGTH: 1198
<212> TYPE: DNA
<213> ORGANISM: Canis familiaris
<220> FEATURE:
<221> NAME/KEY: CDS
<222> LOCATION: (1)..(1125)

<400> SEQUENCE: 5

| ctt | cat | ccc | aca | aac | cct | gaa | gtg | acc | atg | aat | ata | agt | cag | atg | atc | 48 |
|-----|-----|-----|-----|-----|-----|-----|-----|-----|-----|-----|-----|-----|-----|-----|-----|----|
| Leu | His | Pro | Thr | Asn | Pro | Glu | Val | Thr | Met | Asn | Ile | Ser | Gln | Met | Ile | |
| 1 | | | | 5 | | | | | 10 | | | | | 15 | | |

| acc | tac | tgg | gga | tac | cca | gct | gag | gaa | tat | gaa | gtt | gtg | acc | gaa | gac | 96 |
|-----|-----|-----|-----|-----|-----|-----|-----|-----|-----|-----|-----|-----|-----|-----|-----|----|
| Thr | Tyr | Trp | Gly | Tyr | Pro | Ala | Glu | Glu | Tyr | Glu | Val | Val | Thr | Glu | Asp | |
| | | | 20 | | | | | 25 | | | | | 30 | | | |

| ggt | tat | atc | ctt | ggg | atc | gac | aga | att | cct | tat | ggg | agg | aaa | aat | tca | 144 |
|-----|-----|-----|-----|-----|-----|-----|-----|-----|-----|-----|-----|-----|-----|-----|-----|-----|
| Gly | Tyr | Ile | Leu | Gly | Ile | Asp | Arg | Ile | Pro | Tyr | Gly | Arg | Lys | Asn | Ser | |
| | | | 35 | | | | | 40 | | | | | 45 | | | |

| gag | aat | ata | ggc | cgg | aga | cct | gtt | gca | ttt | ttg | caa | cac | ggt | ttg | ctc | 192 |
|-----|-----|-----|-----|-----|-----|-----|-----|-----|-----|-----|-----|-----|-----|-----|-----|-----|
| Glu | Asn | Ile | Gly | Arg | Arg | Pro | Val | Ala | Phe | Leu | Gln | His | Gly | Leu | Leu | |
| | 50 | | | | | 55 | | | | | 60 | | | | | |

| gca | tca | gcc | aca | aac | tgg | atc | tcc | aac | ctg | ccc | aac | aac | agc | ctg | gcc | 240 |
|-----|-----|-----|-----|-----|-----|-----|-----|-----|-----|-----|-----|-----|-----|-----|-----|-----|
| Ala | Ser | Ala | Thr | Asn | Trp | Ile | Ser | Asn | Leu | Pro | Asn | Asn | Ser | Leu | Ala | |
| 65 | | | | 70 | | | | | 75 | | | | | 80 | | |

| ttc | atc | ctg | gcc | gac | gcc | ggg | tac | gac | gtg | tgg | ctg | ggg | aac | agc | agg | 288 |
|-----|-----|-----|-----|-----|-----|-----|-----|-----|-----|-----|-----|-----|-----|-----|-----|-----|
| Phe | Ile | Leu | Ala | Asp | Ala | Gly | Tyr | Asp | Val | Trp | Leu | Gly | Asn | Ser | Arg | |
| | | | 85 | | | | | 90 | | | | | 95 | | | |

| ggc | aac | acc | tgg | gcc | agg | agg | aat | ctg | tac | tac | tcg | ccc | gac | tcc | gtc | 336 |
|-----|-----|-----|-----|-----|-----|-----|-----|-----|-----|-----|-----|-----|-----|-----|-----|-----|
| Gly | Asn | Thr | Trp | Ala | Arg | Arg | Asn | Leu | Tyr | Tyr | Ser | Pro | Asp | Ser | Val | |
| | | | 100 | | | | | 105 | | | | | 110 | | | |

| gaa | ttc | tgg | gct | ttc | agc | ttt | gac | gag | atg | gct | aaa | tat | gac | ctt | ccc | 384 |
|-----|-----|-----|-----|-----|-----|-----|-----|-----|-----|-----|-----|-----|-----|-----|-----|-----|
| Glu | Phe | Trp | Ala | Phe | Ser | Phe | Asp | Glu | Met | Ala | Lys | Tyr | Asp | Leu | Pro | |
| | | 115 | | | | | 120 | | | | | 125 | | | | |

| gcc | acc | att | gac | ttc | atc | ttg | aag | aaa | acg | gga | cag | gac | aag | cta | cac | 432 |
|-----|-----|-----|-----|-----|-----|-----|-----|-----|-----|-----|-----|-----|-----|-----|-----|-----|
| Ala | Thr | Ile | Asp | Phe | Ile | Leu | Lys | Lys | Thr | Gly | Gln | Asp | Lys | Leu | His | |
| | | 130 | | | | | 135 | | | | | 140 | | | | |

| tac | gtt | ggc | cat | tcc | cag | ggc | acc | acc | att | ggt | ttc | atc | gcc | ttt | tcc | 480 |
|-----|-----|-----|-----|-----|-----|-----|-----|-----|-----|-----|-----|-----|-----|-----|-----|-----|
| Tyr | Val | Gly | His | Ser | Gln | Gly | Thr | Thr | Ile | Gly | Phe | Ile | Ala | Phe | Ser | |
| 145 | | | | 150 | | | | | 155 | | | | | 160 | | |

| acc | aat | ccc | aag | ctg | gcg | aaa | cgg | atc | aaa | acc | ttc | tat | gca | tta | gct | 528 |
|-----|-----|-----|-----|-----|-----|-----|-----|-----|-----|-----|-----|-----|-----|-----|-----|-----|
| Thr | Asn | Pro | Lys | Leu | Ala | Lys | Arg | Ile | Lys | Thr | Phe | Tyr | Ala | Leu | Ala | |
| | | | 165 | | | | | 170 | | | | | 175 | | | |

| ccc | gtt | gcc | acc | gtg | aag | tac | acc | gaa | acc | ctg | tta | aac | aaa | ctc | atg | 576 |
|-----|-----|-----|-----|-----|-----|-----|-----|-----|-----|-----|-----|-----|-----|-----|-----|-----|
| Pro | Val | Ala | Thr | Val | Lys | Tyr | Thr | Glu | Thr | Leu | Leu | Asn | Lys | Leu | Met | |
| | | | 180 | | | | | 185 | | | | | 190 | | | |

| ctc | gtc | cct | tcg | ttc | ctc | ttc | aag | ctt | ata | ttt | gga | aac | aaa | ata | ttc | 624 |
|-----|-----|-----|-----|-----|-----|-----|-----|-----|-----|-----|-----|-----|-----|-----|-----|-----|
| Leu | Val | Pro | Ser | Phe | Leu | Phe | Lys | Leu | Ile | Phe | Gly | Asn | Lys | Ile | Phe | |
| | | 195 | | | | | 200 | | | | | 205 | | | | |

| tac | cca | cac | cac | ttc | ttt | gat | caa | ttt | ctc | gcc | acc | gag | gta | tgc | tcc | 672 |
|-----|-----|-----|-----|-----|-----|-----|-----|-----|-----|-----|-----|-----|-----|-----|-----|-----|
| Tyr | Pro | His | His | Phe | Phe | Asp | Gln | Phe | Leu | Ala | Thr | Glu | Val | Cys | Ser | |
| | | 210 | | | | | 215 | | | | | 220 | | | | |

| cgc | gag | acg | gtg | gat | ctc | ctc | tgc | agc | aac | gcc | ctg | ttt | atc | att | tgt | 720 |
|-----|-----|-----|-----|-----|-----|-----|-----|-----|-----|-----|-----|-----|-----|-----|-----|-----|
| Arg | Glu | Thr | Val | Asp | Leu | Leu | Cys | Ser | Asn | Ala | Leu | Phe | Ile | Ile | Cys | |
| 225 | | | | 230 | | | | | 235 | | | | | 240 | | |

| gga | ttt | gac | act | atg | aac | ttg | aac | atg | agt | cgc | ttg | gat | gtg | tat | ctg | 768 |
|-----|-----|-----|-----|-----|-----|-----|-----|-----|-----|-----|-----|-----|-----|-----|-----|-----|
| Gly | Phe | Asp | Thr | Met | Asn | Leu | Asn | Met | Ser | Arg | Leu | Asp | Val | Tyr | Leu | |
| | | | 245 | | | | | 250 | | | | | 255 | | | |

| tca | cat | aat | cca | gca | gga | aca | tcg | gtt | cag | aac | gtg | ctc | cac | tgg | tcc | 816 |
|-----|-----|-----|-----|-----|-----|-----|-----|-----|-----|-----|-----|-----|-----|-----|-----|-----|
| Ser | His | Asn | Pro | Ala | Gly | Thr | Ser | Val | Gln | Asn | Val | Leu | His | Trp | Ser | |

-continued

```
                260                 265                 270
cag gct gtt aag tct ggg aag ttc caa gct ttt gac tgg gga agc cca          864
Gln Ala Val Lys Ser Gly Lys Phe Gln Ala Phe Asp Trp Gly Ser Pro
        275                 280                 285 gtt cag aac atg atg cac tat cat cag agc atg cct ccc tac tac aac          912
Val Gln Asn Met Met His Tyr His Gln Ser Met Pro Pro Tyr Tyr Asn
        290                 295                 300 ctg aca gac atg cat gtg cca atc gca gtg tgg aac ggt ggc aac gac          960
Leu Thr Asp Met His Val Pro Ile Ala Val Trp Asn Gly Gly Asn Asp
305                 310                 315                 320 ttg ctg gcc gac cct cac gat gtt gac ctt ttg ctt tcc aag ctc ccc         1008
Leu Leu Ala Asp Pro His Asp Val Asp Leu Leu Leu Ser Lys Leu Pro
                325                 330                 335 aat ctc att tac cac agg aag att cct cct tac aat cac ttg gac ttt         1056
Asn Leu Ile Tyr His Arg Lys Ile Pro Pro Tyr Asn His Leu Asp Phe
        340                 345                 350 atc tgg gcc atg gat gcc cct caa gcg gtt tac aat gaa att gtt tcc         1104
Ile Trp Ala Met Asp Ala Pro Gln Ala Val Tyr Asn Glu Ile Val Ser
        355                 360                 365 atg atg gga aca gat aat aag tagttctaga tttaaggaat tattctttta            1155
Met Met Gly Thr Asp Asn Lys
        370                 375 ttgttccaaa atacgttctt ctctcacacg tggttttcta tca                         1198
```

<210> SEQ ID NO 6
<211> LENGTH: 375
<212> TYPE: PRT
<213> ORGANISM: Canis familiaris

<400> SEQUENCE: 6

```
Leu His Pro Thr Asn Pro Glu Val Thr Met Asn Ile Ser Gln Met Ile
1               5                  10                  15

Thr Tyr Trp Gly Tyr Pro Ala Glu Glu Tyr Val Val Thr Glu Asp
                20                  25                  30

Gly Tyr Ile Leu Gly Ile Asp Arg Ile Pro Tyr Gly Arg Lys Asn Ser
            35                  40                  45

Glu Asn Ile Gly Arg Arg Pro Val Ala Phe Leu Gln His Gly Leu Leu
        50                  55                  60

Ala Ser Ala Thr Asn Trp Ile Ser Asn Leu Pro Asn Asn Ser Leu Ala
65                  70                  75                  80

Phe Ile Leu Ala Asp Ala Gly Tyr Asp Val Trp Leu Gly Asn Ser Arg
                85                  90                  95

Gly Asn Thr Trp Ala Arg Arg Asn Leu Tyr Tyr Ser Pro Asp Ser Val
            100                 105                 110

Glu Phe Trp Ala Phe Ser Phe Asp Glu Met Ala Lys Tyr Asp Leu Pro
        115                 120                 125

Ala Thr Ile Asp Phe Ile Leu Lys Lys Thr Gly Gln Asp Lys Leu His
    130                 135                 140

Tyr Val Gly His Ser Gln Gly Thr Thr Ile Gly Phe Ile Ala Phe Ser
145                 150                 155                 160

Thr Asn Pro Lys Leu Ala Lys Arg Ile Lys Thr Phe Tyr Ala Leu Ala
                165                 170                 175

Pro Val Ala Thr Val Lys Tyr Thr Glu Thr Leu Leu Asn Lys Leu Met
            180                 185                 190

Leu Val Pro Ser Phe Leu Phe Lys Leu Ile Phe Gly Asn Lys Ile Phe
        195                 200                 205
```

-continued

```
Tyr Pro His His Phe Phe Asp Gln Phe Leu Ala Thr Glu Val Cys Ser
    210                 215                 220

Arg Glu Thr Val Asp Leu Leu Cys Ser Asn Ala Leu Phe Ile Ile Cys
225                 230                 235                 240

Gly Phe Asp Thr Met Asn Leu Asn Met Ser Arg Leu Asp Val Tyr Leu
                245                 250                 255

Ser His Asn Pro Ala Gly Thr Ser Val Gln Asn Val Leu His Trp Ser
            260                 265                 270

Gln Ala Val Lys Ser Gly Lys Phe Gln Ala Phe Asp Trp Gly Ser Pro
        275                 280                 285

Val Gln Asn Met Met His Tyr His Gln Ser Met Pro Pro Tyr Tyr Asn
    290                 295                 300

Leu Thr Asp Met His Val Pro Ile Ala Val Trp Asn Gly Gly Asn Asp
305                 310                 315                 320

Leu Leu Ala Asp Pro His Asp Val Asp Leu Leu Ser Lys Leu Pro
                325                 330                 335

Asn Leu Ile Tyr His Arg Lys Ile Pro Pro Tyr Asn His Leu Asp Phe
                340                 345                 350

Ile Trp Ala Met Asp Ala Pro Gln Ala Val Tyr Asn Glu Ile Val Ser
            355                 360                 365

Met Met Gly Thr Asp Asn Lys
    370                 375

<210> SEQ ID NO 7
<211> LENGTH: 1528
<212> TYPE: DNA
<213> ORGANISM: Canis familiaris

<400> SEQUENCE: 7
ttgtttggaa aattacatcc cacaaaccct gaagtgacca tgaatataag tcagatgatc        60
acctactggg gatacccagc tgaggaatat gaagttgtga ccgaagacgg ttatatcctt      120
gggatcgaca gaattcctta tgggaggaaa aattcagaga atataggccg gagacctgtt      180 gcattttgc aacacggttt gctcgcatca gccacaaact ggatctccaa cctgcccaac       240
aacagcctgg ccttcatcct ggccgacgcc gggtacgacg tgtggctggg aacagcagg       300 ggcaacacct gggccaggag gaatctgtac tactcgcccg actccgtcga attctgggct      360
ttcagctttg acgagatggc taaatatgac cttcccgcca ccattgactt catcttgaag      420
aaaacgggac aggacaagct acactacgtt ggccattccc agggcaccac cattggtttc      480
atcgcctttt ccaccaatcc caagctggcg aaacggatca aaaccttcta tgcattagct      540
cccgttgcca ccgtgaagta caccgaaacc ctgttaaaca aactcatgct cgtcccttcg      600
ttcctcttca gcttatatt tggaaacaaa atattctacc cacaccactt ctttgatcaa      660
tttctcgcca ccgaggtatg ctcccgcgag acggtggatc tcctctgcag caacgccctg      720
tttatcattt gtggatttga cactatgaac ttgaacatga gtcgcttgga tgtgtatctg      780
tcacataatc cagcaggaac atcggttcag aacgtgctcc actggtccca ggctgttaag      840
tctgggaagt tccaagcttt tgactgggga agcccagttc agaacatgat gcactatcat      900
cagagcatgc ctccctacta caacctgaca gacatgcatg tgccaatcgc agtgtggaac      960
ggtggcaacg acttgctggc cgaccctcac gatgttgacc ttttgctttc caagctcccc     1020
aatctcattt accacaggaa gattcctcct tacaatcact ggactttat ctgggccatg      1080 gatgcccctc aagcggttta caatgaaatt gtttccatga tgggaacaga taataagtag     1140
```

-continued

```
ttctagattt aaggaattat tcttttattg ttccaaaata cgttcttctc tcacacgtgg    1200
ttttctatca tgtttgagac acggtgattg ttcccatggt tttgatttca gaaatgtgtt    1260
agcatcaaca atctttccat tggtaatttt tgaatttaaa atgattttta aatttggggc    1320
atctgggtgg ctcagttggc taagtcgtct gccttggctt aagtcatgat ctcggggtcc    1380
taggatggag ccttgtgtct gggctcctgc cggggcgggg gtctgcttct cctcctgctg    1440
ctcccccctg ctgctgtgtg cacacacgct ctctctctct caaataaata aataaataaa    1500
tacttaataa aataaaaaaa aaaaaaaa                                       1528

<210> SEQ ID NO 8
<211> LENGTH: 1367
<212> TYPE: DNA
<213> ORGANISM: Homo sapiens
<220> FEATURE:
<221> NAME/KEY: CDS
<222> LOCATION: (47)..(1240)

<400> SEQUENCE: 8
agagaaacag aatcctaact atttctgagg aaactgcagg tccaaa atg tgg ctg           55
                                                   Met Trp Leu
                                                    1 ctt tta aca atg gca agt ttg ata tct gta ctg ggg act aca cat ggt        103
Leu Leu Thr Met Ala Ser Leu Ile Ser Val Leu Gly Thr Thr His Gly
     5                  10                  15 ttg ttt gga aaa tta cat cct gga agc cct gaa gtg act atg aac att        151
Leu Phe Gly Lys Leu His Pro Gly Ser Pro Glu Val Thr Met Asn Ile
 20                  25                  30                  35 agt cag atg att act tat tgg gga tac cca aat gaa gaa tat gaa gtt        199
Ser Gln Met Ile Thr Tyr Trp Gly Tyr Pro Asn Glu Glu Tyr Glu Val
                 40                  45                  50 gtg act gaa gat ggt tat att ctt gaa gtc aat aga att cct tat ggg        247
Val Thr Glu Asp Gly Tyr Ile Leu Glu Val Asn Arg Ile Pro Tyr Gly
             55                  60                  65 aag aaa aat tca ggg aat aca ggc cag aga cct gtt gtg ttt ttg cag        295
Lys Lys Asn Ser Gly Asn Thr Gly Gln Arg Pro Val Val Phe Leu Gln
         70                  75                  80 cat ggt ttg ctt gca tca gcc aca aac tgg att tcc aac ctg ccg aac        343
His Gly Leu Leu Ala Ser Ala Thr Asn Trp Ile Ser Asn Leu Pro Asn
 85                  90                  95 aac agc ctt gcc ttc att ctg gca gat gct ggt tat gat gtg tgg ctg        391
Asn Ser Leu Ala Phe Ile Leu Ala Asp Ala Gly Tyr Asp Val Trp Leu
100                 105                 110                 115 ggc aac agc aga gga aac acc tgg gcc aga aga aac ttg tac tat tca        439
Gly Asn Ser Arg Gly Asn Thr Trp Ala Arg Arg Asn Leu Tyr Tyr Ser
                120                 125                 130 cca gat tca gtt gaa ttc tgg gct ttc agc ttt gat gaa atg gct aaa        487
Pro Asp Ser Val Glu Phe Trp Ala Phe Ser Phe Asp Glu Met Ala Lys
            135                 140                 145 tat gac ctt cca gcc aca atc gac ttc att gta aag aaa act gga cag        535
Tyr Asp Leu Pro Ala Thr Ile Asp Phe Ile Val Lys Lys Thr Gly Gln
        150                 155                 160 aag cag cta cac tat gtt ggc cat tcc cag ggc acc acc att ggt ttt        583
Lys Gln Leu His Tyr Val Gly His Ser Gln Gly Thr Thr Ile Gly Phe
    165                 170                 175 att gcc ttt tcc acc aat ccc agc ctg gct aaa aga atc aaa acc ttc        631
Ile Ala Phe Ser Thr Asn Pro Ser Leu Ala Lys Arg Ile Lys Thr Phe
180                 185                 190                 195 tat gct cta gct cct gtt gcc act gtg aag tat aca aaa agc ctt ata        679
Tyr Ala Leu Ala Pro Val Ala Thr Val Lys Tyr Thr Lys Ser Leu Ile
```

```
aac aaa ctt aga ttt gtt cct caa tcc ctc ttc aag ttt ata ttt ggt      727
Asn Lys Leu Arg Phe Val Pro Gln Ser Leu Phe Lys Phe Ile Phe Gly
            215                 220                 225 gac aaa ata ttc tac cca cac aac ttc ttt gat caa ttt ctt gct act      775
Asp Lys Ile Phe Tyr Pro His Asn Phe Phe Asp Gln Phe Leu Ala Thr
            230                 235                 240 gaa gtg tgc tcc cgt gag atg ctg aat ctc ctt tgc agc aat gcc tta      823
Glu Val Cys Ser Arg Glu Met Leu Asn Leu Leu Cys Ser Asn Ala Leu
245                 250                 255 ttt ata att tgt gga ttt gac agt aag aac ttt aac acg agt cgc ttg      871
Phe Ile Ile Cys Gly Phe Asp Ser Lys Asn Phe Asn Thr Ser Arg Leu
260                 265                 270                 275 gat gtg tat cta tca cat aat cca gca gga act tct gtt caa aac atg      919
Asp Val Tyr Leu Ser His Asn Pro Ala Gly Thr Ser Val Gln Asn Met
                280                 285                 290 ttc cat tgg acc cag gct gtt aag tct ggg aaa ttc caa gct tat gac      967
Phe His Trp Thr Gln Ala Val Lys Ser Gly Lys Phe Gln Ala Tyr Asp
            295                 300                 305 tgg gga agc cca gtt cag aat agg atg cac tat gat cag tcc caa cct     1015
Trp Gly Ser Pro Val Gln Asn Arg Met His Tyr Asp Gln Ser Gln Pro
            310                 315                 320 ccc tac tac aat gtg aca gcc atg aat gta cca att gca gtg tgg aac     1063
Pro Tyr Tyr Asn Val Thr Ala Met Asn Val Pro Ile Ala Val Trp Asn
325                 330                 335 ggt ggc aag gac ctg ttg gct gac ccc caa gat gtt ggc ctt ttg ctt     1111
Gly Gly Lys Asp Leu Leu Ala Asp Pro Gln Asp Val Gly Leu Leu Leu
340                 345                 350                 355 cca aaa ctc ccc aat ctt att tac cac aag gag att cct ttt tac aat     1159
Pro Lys Leu Pro Asn Leu Ile Tyr His Lys Glu Ile Pro Phe Tyr Asn
                360                 365                 370 cac ttg gac ttt atc tgg gca atg gat gcc cct caa gaa gtt tac aat     1207
His Leu Asp Phe Ile Trp Ala Met Asp Ala Pro Gln Glu Val Tyr Asn
            375                 380                 385 gac att gtt tct atg ata tca gaa gat aaa aag tagttctgga tttaaagaat   1260
Asp Ile Val Ser Met Ile Ser Glu Asp Lys Lys
            390                 395 tatccgtttg tttttccaaa atactttatt ctctcataca tagtatttc ataatgttg    1320 acatgcagtg cttctttctg taattttgac tttagaaata tattggc                 1367

<210> SEQ ID NO 9
<211> LENGTH: 398
<212> TYPE: PRT
<213> ORGANISM: Homo sapiens

<400> SEQUENCE: 9

Met Trp Leu Leu Leu Thr Met Ala Ser Leu Ile Ser Val Leu Gly Thr
1               5                   10                  15

Thr His Gly Leu Phe Gly Lys Leu His Pro Gly Ser Pro Glu Val Thr
            20                  25                  30

Met Asn Ile Ser Gln Met Ile Thr Tyr Trp Gly Tyr Pro Asn Glu Glu
        35                  40                  45

Tyr Glu Val Val Thr Glu Asp Gly Tyr Ile Leu Glu Val Asn Arg Ile
    50                  55                  60

Pro Tyr Gly Lys Lys Asn Ser Gly Asn Thr Gly Gln Arg Pro Val Val
65                  70                  75                  80

Phe Leu Gln His Gly Leu Leu Ala Ser Ala Thr Asn Trp Ile Ser Asn
                85                  90                  95
```

```
Leu Pro Asn Asn Ser Leu Ala Phe Ile Leu Ala Asp Ala Gly Tyr Asp
            100                 105                 110

Val Trp Leu Gly Asn Ser Arg Gly Asn Thr Trp Ala Arg Arg Asn Leu
        115                 120                 125

Tyr Tyr Ser Pro Asp Ser Val Glu Phe Trp Ala Phe Ser Phe Asp Glu
        130                 135                 140

Met Ala Lys Tyr Asp Leu Pro Ala Thr Ile Asp Phe Ile Val Lys Lys
145                 150                 155                 160

Thr Gly Gln Lys Gln Leu His Tyr Val Gly His Ser Gln Gly Thr Thr
                165                 170                 175

Ile Gly Phe Ile Ala Phe Ser Thr Asn Pro Ser Leu Ala Lys Arg Ile
                180                 185                 190

Lys Thr Phe Tyr Ala Leu Ala Pro Val Ala Thr Val Lys Tyr Thr Lys
                195                 200                 205

Ser Leu Ile Asn Lys Leu Arg Phe Val Pro Gln Ser Leu Phe Lys Phe
            210                 215                 220

Ile Phe Gly Asp Lys Ile Phe Tyr Pro His Asn Phe Phe Asp Gln Phe
225                 230                 235                 240

Leu Ala Thr Glu Val Cys Ser Arg Glu Met Leu Asn Leu Leu Cys Ser
                245                 250                 255

Asn Ala Leu Phe Ile Ile Cys Gly Phe Asp Ser Lys Asn Phe Asn Thr
                260                 265                 270

Ser Arg Leu Asp Val Tyr Leu Ser His Asn Pro Ala Gly Thr Ser Val
                275                 280                 285

Gln Asn Met Phe His Trp Thr Gln Ala Val Lys Ser Gly Lys Phe Gln
            290                 295                 300

Ala Tyr Asp Trp Gly Ser Pro Val Gln Asn Arg Met His Tyr Asp Gln
305                 310                 315                 320

Ser Gln Pro Pro Tyr Tyr Asn Val Thr Ala Met Asn Val Pro Ile Ala
                325                 330                 335

Val Trp Asn Gly Gly Lys Asp Leu Leu Ala Asp Pro Gln Asp Val Gly
                340                 345                 350

Leu Leu Leu Pro Lys Leu Pro Asn Leu Ile Tyr His Lys Glu Ile Pro
                355                 360                 365

Phe Tyr Asn His Leu Asp Phe Ile Trp Ala Met Asp Ala Pro Gln Glu
            370                 375                 380

Val Tyr Asn Asp Ile Val Ser Met Ile Ser Glu Asp Lys Lys
385                 390                 395

<210> SEQ ID NO 10
<211> LENGTH: 29
<212> TYPE: DNA
<213> ORGANISM: Unknown
<220> FEATURE:
<223> OTHER INFORMATION: PCR mutagenesis primer

<400> SEQUENCE: 10
caggagatct tgttggaaag cttcatccc                                    29

<210> SEQ ID NO 11
<211> LENGTH: 21
<212> TYPE: DNA
<213> ORGANISM: Unknown
<220> FEATURE:
<223> OTHER INFORMATION: PCR mutagenesis primer

<400> SEQUENCE: 11
```

```
catattcctc agctgggtat c                                              21

<210> SEQ ID NO 12
<211> LENGTH: 9
<212> TYPE: PRT
<213> ORGANISM: Canis familiaris

<400> SEQUENCE: 12

Leu Phe Gly Lys Leu Thr Asp Asn Lys
1               5

<210> SEQ ID NO 13
<211> LENGTH: 42
<212> TYPE: DNA
<213> ORGANISM: Canis familiaris

<400> SEQUENCE: 13
agatcttgtt tggaaagctt acagataata agtagttcta ga                       42

<210> SEQ ID NO 14
<211> LENGTH: 69
<212> TYPE: DNA
<213> ORGANISM: Unknown
<220> FEATURE:
<223> OTHER INFORMATION: Sequence encoding signal peptide of sporamin A

<400> SEQUENCE: 14
atgaaagcct tcacactcgc tctcttctta gctctttccc tctatctcct gcccaatcca    60
gcccattcc                                                            69

<210> SEQ ID NO 15
<211> LENGTH: 31
<212> TYPE: DNA
<213> ORGANISM: Unknown
<220> FEATURE:
<223> OTHER INFORMATION: PCR primer

<400> SEQUENCE: 15
caggagatct gatgaaagcc ttcacactcg c                                   31

<210> SEQ ID NO 16
<211> LENGTH: 40
<212> TYPE: DNA
<213> ORGANISM: Unknown
<220> FEATURE:
<223> OTHER INFORMATION: PCR primer

<400> SEQUENCE: 16
atgaagcttt ccaaacaagg aatgggctgg attgggcagg                          40

<210> SEQ ID NO 17
<211> LENGTH: 111
<212> TYPE: DNA
<213> ORGANISM: Unknown
<220> FEATURE:
<223> OTHER INFORMATION: Sequence encoding signal prepropeptide of
      sporamin A

<400> SEQUENCE: 17
atgaaagcct tcacactcgc tctcttctta gctctttccc tctatctcct gcccaatcca    60
gcccattcca ggttcaatcc catccgcctc cccaccacac acgaacccgc c            111

<210> SEQ ID NO 18
```

```
<211> LENGTH: 38
<212> TYPE: DNA
<213> ORGANISM: Unknown
<220> FEATURE:
<223> OTHER INFORMATION: PCR primer

<400> SEQUENCE: 18
atgaagcttt ccaaacaagg cgggttcgtg tgtggttg                         38

<210> SEQ ID NO 19
<211> LENGTH: 19
<212> TYPE: PRT
<213> ORGANISM: Rabbit

<400> SEQUENCE: 19

Met Trp Val Leu Phe Met Val Ala Ala Leu Leu Ser Ala Leu Gly Thr
1               5                   10                  15

Thr His Gly

<210> SEQ ID NO 20
<211> LENGTH: 57
<212> TYPE: DNA
<213> ORGANISM: Rabbit

<400> SEQUENCE: 20
atgtgggtgc ttttcatggt ggcagctttg ctatctgcac ttggaactac acatggt    57

<210> SEQ ID NO 21
<211> LENGTH: 35
<212> TYPE: DNA
<213> ORGANISM: Unknown
<220> FEATURE:
<223> OTHER INFORMATION: PCR primer

<400> SEQUENCE: 21
aggagatctc aacaatgtgg gtgcttttca tggtg                            35

<210> SEQ ID NO 22
<211> LENGTH: 38
<212> TYPE: DNA
<213> ORGANISM: Unknown
<220> FEATURE:
<223> OTHER INFORMATION: PCR primer

<400> SEQUENCE: 22
atgaagcttt ccaaacaaac catgtgtagt tccaagtg                         38

<210> SEQ ID NO 23
<211> LENGTH: 19
<212> TYPE: DNA
<213> ORGANISM: Unknown
<220> FEATURE:
<223> OTHER INFORMATION: PCR primer

<400> SEQUENCE: 23
caaacgtgta caatagccc                                              19

<210> SEQ ID NO 24
<211> LENGTH: 18
<212> TYPE: DNA
<213> ORGANISM: Unknown
<220> FEATURE:
<223> OTHER INFORMATION: PCR primer

<400> SEQUENCE: 24
```
cccggggatc cttttttg                                                    18

<210> SEQ ID NO 25
<211> LENGTH: 19
<212> TYPE: DNA
<213> ORGANISM: Unknown
<220> FEATURE:
<223> OTHER INFORMATION: PCR primer

<400> SEQUENCE: 25
aagtacggcc actaccacg                                                   19

<210> SEQ ID NO 26
<211> LENGTH: 17
<212> TYPE: DNA
<213> ORGANISM: Unknown
<220> FEATURE:
<223> OTHER INFORMATION: PCR primer

<400> SEQUENCE: 26
cccggggatc ctggctc                                                     17

<210> SEQ ID NO 27
<211> LENGTH: 42
<212> TYPE: DNA
<213> ORGANISM: Unknown
<220> FEATURE:
<223> OTHER INFORMATION: PCR primer

<400> SEQUENCE: 27
ttgtttggaa aattacatcc tggatcccct gaagtgacta tg                         42

<210> SEQ ID NO 28
<211> LENGTH: 40
<212> TYPE: DNA
<213> ORGANISM: Unknown
<220> FEATURE:
<223> OTHER INFORMATION: PCR primer

<400> SEQUENCE: 28
aatggtggtg ccctgggaat ggccaacata gtgtagctgc                            40

<210> SEQ ID NO 29
<211> LENGTH: 48
<212> TYPE: DNA
<213> ORGANISM: Homo sapiens

<400> SEQUENCE: 29
atgctgccac tttggactct ttcactgctg ctgggagcag tagcagga                   48

<210> SEQ ID NO 30
<211> LENGTH: 99
<212> TYPE: DNA
<213> ORGANISM: Homo sapiens

<400> SEQUENCE: 30
aaactgcagg ctcgagaaca atgctgccac tttggactct ttcactgctg ctgggagcag      60
tagcaggatt gtttggaaaa ttacatcctg gatcccctg                             99

<210> SEQ ID NO 31
<211> LENGTH: 24
<212> TYPE: DNA
<213> ORGANISM: Unknown
<220> FEATURE:
<223> OTHER INFORMATION: PCR primer

```
<400> SEQUENCE: 31
aaactgcagg ctcgagaaca atgc                                          24

<210> SEQ ID NO 32
<211> LENGTH: 24
<212> TYPE: DNA
<213> ORGANISM: Unknown
<220> FEATURE:
<223> OTHER INFORMATION: PCR primer

<400> SEQUENCE: 32
aggggatcca ggatgtaatt ttcc                                          24

<210> SEQ ID NO 33
<211> LENGTH: 57
<212> TYPE: DNA
<213> ORGANISM: Rabbit

<400> SEQUENCE: 33
atgtgggtgc ttttcatggt ggcagctttg ctatctgcac ttggaactac acatggt      57

<210> SEQ ID NO 34
<211> LENGTH: 108
<212> TYPE: DNA
<213> ORGANISM: Unknown
<220> FEATURE:
<223> OTHER INFORMATION: PCR template

<400> SEQUENCE: 34
aaactgcagg ctcgagaaca atgtgggtgc ttttcatggt ggcagctttg ctatctgcac   60
ttggaactac acatggtttg tttggaaaat tacatcctgg atcccctg                108

<210> SEQ ID NO 35
<211> LENGTH: 26
<212> TYPE: DNA
<213> ORGANISM: Unknown
<220> FEATURE:
<223> OTHER INFORMATION: PCR primer

<400> SEQUENCE: 35
aaactgcagg ctcgagaaca atgtgg                                        26

<210> SEQ ID NO 36
<211> LENGTH: 33
<212> TYPE: DNA
<213> ORGANISM: Unknown
<220> FEATURE:
<223> OTHER INFORMATION: PCR primer

<400> SEQUENCE: 36
aatcacttgg actttatctg ggccatggat gcc                                33

<210> SEQ ID NO 37
<211> LENGTH: 97
<212> TYPE: DNA
<213> ORGANISM: Unknown
<220> FEATURE:
<223> OTHER INFORMATION: PCR primer

<400> SEQUENCE: 37
attcttaaga aactttattg ccaaatgttt gaacgatcgg ggaaattcga ctgcgtctag   60
aactatagct catccttatt atctgttccc atcatgg                            97
```